United States Patent
Prüß et al.

(10) Patent No.: US 11,452,292 B2
(45) Date of Patent: Sep. 27, 2022

(54) BIOFILM INHIBITOR AND METHOD OF INHIBITING BIOFILM

(71) Applicant: NDSU Research Foundation, Fargo, ND (US)

(72) Inventors: Birgit M. Prüß, Fargo, ND (US); Meredith Schroeder, Fargo, ND (US); Shelley M. Horne, Fargo, ND (US); Shane J. Stafslien, Fargo, ND (US)

(73) Assignee: NDSU RESEARCH FOUNDATION, Fargo, ND (US)

( * ) Notice: Subject to any disclaimer, the term of this patent is extended or adjusted under 35 U.S.C. 154(b) by 0 days.

(21) Appl. No.: 16/138,630

(22) Filed: Sep. 21, 2018

(65) Prior Publication Data

US 2019/0082688 A1 Mar. 21, 2019

Related U.S. Application Data

(60) Provisional application No. 62/561,353, filed on Sep. 21, 2017.

(51) Int. Cl.
*A01N 37/42* (2006.01)
*A01N 25/10* (2006.01)
(Continued)

(52) U.S. Cl.
CPC ............ *A01N 37/42* (2013.01); *A01N 25/02* (2013.01); *A01N 25/10* (2013.01); *A61L 29/085* (2013.01);
(Continued)

(58) Field of Classification Search
CPC ........ A01N 37/42; A01N 25/10; A01N 25/02; A61M 25/0009; A61M 25/0045;
(Continued)

(56) References Cited

U.S. PATENT DOCUMENTS

| | | | |
|---|---|---|---|
| 7,578,970 B2* | 8/2009 | Bowker | A01N 59/00 422/28 |
| 2003/0012857 A1* | 1/2003 | Alam | A23B 4/20 426/332 |
| 2014/0135297 A1* | 5/2014 | Narayanan | A01N 25/04 514/159 |

OTHER PUBLICATIONS

Leonard et al., "Bioactivities of selected essential oil and some components on Listeria monocytogenes biofilms", South African Journal of Botany, 76 (2010),676-680. (Year: 2010).*

(Continued)

*Primary Examiner* — Jianfeng Song
(74) *Attorney, Agent, or Firm* — Stites & Harbison, PLLC; Mandy Wilson Decker; Gary N. Stewart

(57) ABSTRACT

Provided herein are a biofilm inhibiting composition, a biofilm inhibiting article, and a method of reducing planktonic growth or biofilm formation. The biofilm inhibiting composition includes a fluid and at least one biofilm inhibiting compound selected from the group consisting of acetoacetate (AAA) and ethyl acetoacetate (EAA). The biofilm inhibiting article includes a substrate and at least one biofilm inhibiting compound selected from the group consisting of acetoacetate (AAA) and ethyl acetoacetate (EAA). The method of reducing biofilm formation includes providing a biofilm inhibiting compound selected from the group consisting of acetoacetate (AAA) and ethyl acetoacetate (EAA), and contacting an article with the biofilm inhibiting compound.

8 Claims, 20 Drawing Sheets

Specification includes a Sequence Listing.

(51) Int. Cl.
  *A61L 29/08* (2006.01)
  *A61L 29/16* (2006.01)
  *A01N 25/02* (2006.01)
  *A61M 25/00* (2006.01)

(52) U.S. Cl.
  CPC ............ *A61L 29/16* (2013.01); *A61L 2300/21* (2013.01); *A61L 2300/404* (2013.01); *A61M 25/0009* (2013.01); *A61M 25/0045* (2013.01); *A61M 2205/0205* (2013.01)

(58) Field of Classification Search
  CPC .............. A61L 2300/404; A61L 29/085; A61L 2300/21; A61L 29/16
  See application file for complete search history.

(56) References Cited

OTHER PUBLICATIONS

Skandamis et al., "The effect of oregano essential oil on Survival / death of *Salmonella typhimurium* in meat stored at 5° C. under aerobic, VP/MAP conditions", Food Microbiology, 2002, 19, 97-103. (Year: 2002).*
Albarracin H et al., "Application of essential oils as a preservative to improve the shelf life of Nile tilapia", Vitae, vol. 19, No. 1 Medellin, 2012, 34-40. (Year: 2012).*
Al-Nabulsi, A.A., Osaili, T.M., Elabedeen, N.A., Jaradat, Z.W., Shaker, R.R., Kheirallah, K.A., Tarazi, Y.H. and Holley, R.A. (2011) Impact of environmental stress desiccation, acidity, alkalinity, heat or cold on antibiotic susceptibility of Cronobacter sakazakii. Int J Food Microbiol 146, 137-143.
Badger, J.L., Young, B.M., Darwin, A.J. and Miller, V.L. (2000) Yersinia enterocolitica ClpB affects levels of invasin and motility. J Bacteriol 182, 5563-5571.
Bleves, S., Marenne, M.N., Detry, G. and Cornelis, G.R. (2002) Up-regulation of the Yersinia enterocolitica yop regulon by deletion of the flagellum master operon flhDC. J Bacteriol 184, 3214-3223.
Bradford, W.D., Noce, P.S. and Gutman, L.T. (1974) Pathologic features of enteric infection with Yersinia enterocolitica. Arch Pathol 98, 17-22.
Breeuwer, P., Lardeau, A., Peterz, M. and Joosten, H.M. (2003) Desiccation and heat tolerance of Enterobacter sakazakii. J Appl Microbiol 95, 967-973.
Brzostek, K., Skorek, K. and Raczkowska, A. (2012) OmpR, a central integrator of several cellular responses in Yersinia enterocolitica. Adv Exp Med Biol 954, 325-334.
Butler, J.F., Garcia-Maruniak, A., Meek, F. and Maruniak, J.E. (2010) Wild Florida house flies (*Musca domestica*) as carriers of pathogenic bacteria. Florida Entomologist 93, 218-223.
Carniel, E., Mazigh, D. and Mollaret, H.H. (1987) Expression of iron-regulated proteins in *Yersinia* species and their relation to virulence. Infect Immun 55, 277-280.
Carter, P.B. (1975) Pathogenecity of Yersinia enterocolitica for mice. Infect Immun 11, 164-170.
Chen, C.Y., Hogarth, L.A. and Shanley, M.S. (1991) Regulatory sequences controlling short chain fatty acid metabolism in *Escherichia coli*. SAAS bulletin, biochemistry and biotechnology 4, 22-26.
Chuang, S.E., Daniels, D.L. and Blattner, F.R. (1993) Global regulation of gene expression in *Escherichia coli*. J Bacteriol 175, 2026-2036.
Cornelis, G.R. (2002) The Yersinia Ysc-Yop virulence apparatus. Int J Med Microbiol 291, 455-462.
Cornelis, G.R., Sluiters, C., Delor, I., Geib, D., Kaniga, K., Lambert De Rouvroit, C., Sory, M.P., Vanooteghem, J.C. and Michiels, T. (1991) ymoA, a Yersinia enterocolitica chromosomal gene modulating the expression of virulence functions. Mol Microbiol 5, 1023-1034.

Dhar, M.S. and Virdi, J.S. (2014) Strategies used by Yersinia enterocolitica to evade killing by the host: thinking beyond Yops. Microbes and infection 16, 87-95.
Farmer, J.J., 3rd (2015) My 40-year history with Cronobacter/Enterobacter sakazakii—lessons learned, myths debunked, and recommendations. Frontiers in pediatrics 3, 84.
Friedemann, M. (2007) Enterobacter sakazakii in food and beverages (other than infant formula and milk powder). Int J Food Microbiol 116, 1-10.
Gottschalk, P.G. and Dunn, J.R. (2005) The five-parameter logistic: a characterization and comparison with the four-parameter logistic. Anal Biochem 343, 54-65.
Gupta, V., Gulati, P., Bhagat, N., Dhar, M.S. and Virdi, J.S. (2015) Detection of Yersinia enterocolitica in food: an overview. European journal of clinical microbiology & infectious diseases : official publication of the European Society of Clinical Microbiology 34, 641-650.
Ham, Y. and Kim, T.J. (2016) Inhibitory activity of monoacylglycerols on biofilm formation in Aeromonas hydrophila, *Streptococcus mutans*, Xanthomonas oryzae, and Yersinia enterocolitica. SpringerPlus 5, 1526.
Himelright, I. (2002) Enterobacteri sakazakii infections associated with the use of powdered infant formula—Tennessee 2001. Morb Mortal Wkly Rep 51, 298-300.
Hinchliffe, S.J., Howard, S.L., Huang, Y.H., Clarke, D.J. and Wren, B.W. (2008) The importance of the Rcs phosphorelay in the survival and pathogenesis of the enteropathogenic Yersiniae. Microbiology 154, 1117-1131.
Horne, S.M. and Prüß, B.M. (2006) Global gene regulation in Yersinia enterocolitica: effect of FliA on the expression levels of flagellar and plasmid-encoded virulence genes. Arch Microbiol 185, 115-126.
Hurrell, E., Kucerova, E., Loughlin, M., Caubilla-Barron, J., Hilton, A., Armstrong, R., Smith, C., Grant, J., Shoo, S. and Forsythe, S. (2009) Neonatal enteral feeding tubes as loci for colonisation by members of the Enterobacteriaceae. BMC infectious diseases 9, 146.
Ioannidis, A., Kyratsa, A., Ioannidou, V., Bersimis, S. and Chatzipanagiotou, S. (2014) Detection of biofilm production of *Yersinia enterocolitica* strains isolated from infected children and comparative antimicrobial susceptibility of biofilm versus planktonic forms. Molecular diagnosis & therapy 18, 309-314.
Iversen, C., Lane, M. and Forsythe, S.J. (2004) The growth profile, thermotolerance and biofilm formation of Enterobacter sakazakii grown in infant formula milk. Lett Appl Microbiol 38, 378-382.
Kalyantanda, G., Shumyak, L. and Archibald, L.K. (2015) Cronobacter species contamination of powdered infant formula and the implications for neonatal health. Frontiers in pediatrics 3, 56.
Kandhai, M.C., Reij, M.W., Gorris, L.G., Guillaume-Gentil, O. and Van Schothorst, M. (2004) Occurrence of Enterobacter sakazakii in food production environments and households. Lancet 363, 39-40.
Kapatral, V., Campbell, J.W., Minnich, S.A., Thomson, N.R., Matsumura, P. and Prüß, B.M. (2004) Gene array analysis of Yersinia enterocolitica FlhD and FlhC: regulation of enzymes affecting synthesis and degradation of carbamoylphosphate. Microbiology 150, 2289-2300.
Lambert De Rouvroit, C., Sluiters, C. and Cornelis, G.R. (1992) Role of the transcriptional activator, VirF, and temperature in the expression of the pYV plasmid genes of Yersinia enterocolitica. Mol Microbiol 6, 395-409.
Larson, E.L., Cimiotti, J.P., Haas, J., Nesin, M., Allen, A., Della-Latta, P. and Saiman, L. (2005) Gram-negative bacilli associated with catheter-associated and non-catheter-associated bloodstream infections and hand carriage by healthcare workers in neonatal intensive care units. Pediatric critical care medicine : a journal of the Society of Critical Care Medicine and the World Federation of Pediatric Intensive and Critical Care Societies 6, 457-461.
Lynnes, T., Horne, S.M. and Prüß, B.M. (2014) β-Phenylethylamine as a novel nutrient treatment to reduce bacterial contamination due to *Escherichia coli* O157:H7 on beef meat. Meat Sci 96, 165-171.

(56) References Cited

OTHER PUBLICATIONS

Mahlen, S.D. (2011) Serratia infections: from military experiments to current practice. Clinical microbiology reviews 24, 755-791.

Mcnally, A., La Ragione, R.M., Best, A., Manning, G. and Newell, D.G. (2007) An aflagellate mutant Yersinia enterocolitica biotype 1A strain displays altered invasion of epithelial cells, persistence in macrophages, and cytokine secretion profiles in vitro. Microbiology 153, 1339-1349.

Mcnally, A., Thomson, N.R., Reuter, S. and Wren, B.W. (2016) 'Add, stir and reduce': Yersinia spp. as model bacteria for pathogen evolution. Nat Rev Microbiol 14, 177-190.

Molla, A., Kagimoto, T. and Maeda, H. (1988) Cleavage of immunoglobulin G (IgG) and IgA around the hinge region by proteases from Serratia marcescens. Infect Immun 56, 916-920.

O'Toole, G.A., Pratt, L.A., Watnick, P.I., Newman, D.K., Weaver, V.B. and Kolter, R. (1999) Genetic approaches to study of biofilms. Methods Enzymol 310, 91-109.

Pepe, J.C. and Miller, V.L. (1993) Yersinia enterocolitica invasin: a primary role in the initiation of infection. Proc Natl Acad Sci U S A 90, 6473-6477.

Pepe, J.C., Wachtel, M.R., Wagar, E. and Miller, V.L. (1995) Pathogenesis of defined invasion mutants of Yersinia enterocolitica in a BALB/c mouse model of infection. Infect Immun 63, 4837-4848.

Pfaffl, M.W. (2001) A new mathematical model for relative quantification in real-time RT-PCR. Nucleic Acids Res 29, e45.

Portnoy, D.A. and Falkow, S. (1981) Virulence-associated plasmids from Yersinia enterocolitica and Yersinia pestis. J Bacteriol 148, 877-883.

Portnoy, D.A., Moseley, S.L. and Falkow, S. (1981) Characterization of plasmids and plasmid-associated determinants of Yersinia enterocolitica pathogenesis. Infect Immun 31, 775-782.

Potezny, N., Atkinson, E.R., Rofe, A.M. and Conyers, R.A. (1981) The inhibition of bacterial cell growth by ketone bodies. The Australian journal of experimental biology and medical science 59, 639-649.

Rana, K., Thaper, D. and Prabha, V. (2017) Is there a role for Serratia marcescens in male infertility: An experimental study? Microbial pathogenesis 105, 13-18.

Ray, C., Shenoy, A.T., Orihuela, C.J. and Gonzalez-Juarbe, N. (2017) Killing of Serratia marcescens biofilms with chloramphenicol. Annals of clinical microbiology and antimicrobials 16, 19.

Ruckdeschel, K., Deuretzbacher, A. and Haase, R. (2008) Crosstalk of signalling processes of innate immunity with Yersinia Yop effector functions. Immunobiology 213, 261-269.

Sauer, K., Camper, A.K., Ehrlich, G.D., Costerton, J.W. and Davies, D.G. (2002) Pseudomonas aeruginosa displays multiple phenotypes during development as a biofilm. J Bacteriol 184, 1140-1154.

Schmid, M., Iversen, C., Gontia, I., Stephan, R., Hofmann, A., Hartmann, A., Jha, B., Eberl, L., Riedel, K. and Lehner, A. (2009) Evidence for a plant-associated natural habitat for Cronobacter spp. Res Microbiol 160, 608-614.

Schneider, D.A. and Gourse, R.L. (2004) Relationship between growth rate and ATP concentration in Escherichia coli: a bioassay for available cellular ATP. J Biol Chem 279, 8262-8268.

Skurnik, M. and Toivanen, P. (1992) LcrF is the temperature-regulated activator of the yadA gene of Yersinia enterocolitica and Yersinia pseudotuberculosis. J Bacteriol 174, 2047-2051.

Theodorou, M.C., Theodorou, E.C. and Kyriakidis, D.A. (2012) Involvement of AtoSC two-component system in Escherichia coli flagellar regulon. Amino Acids 43, 833-844.

Mühling M, Bradford A, Readman JW, Somerfield PJ, Handy RD: An investigation into the effects of silver nanoparticles on antibiotic resistance of naturally occurring bacteria in an estuarine sediment. Marine Environmental Research 2009, 68(5):278-283.

Silver S, Phung, L.T. and Silver, G.: Silver as biocides in burn and wound dressings and bacterial resistance to silver compounds. Journal of Industrial Microbiology & Biotechnology 2006, 33(627).

Jena P. MS, Mallick R., Jacob B., Sonawane A: Toxicity and antibacterial assessment of chitosan-coated silver nanoparticles on human pathogens and macrophage cells. International Journal of Nanomedicine 2012, 7:1805-1818.

Stevens K.N. C-BO, Van Den Bosch E.E., Dias A.A., Knetsch M.L., Aldenhoff Y.B., Van Der Veen F.H., Maessen J.G., Stobberingh E.E., Koole L.H.: The relationship between the antimicrobial effect of catheter coatings containing silver nanoparticles and the coagulation of contacting blood. Biomaterials 2009, 30:3682-3690.

Norris LB, Kablaoui F, Brilhart MK, Bookstaver PB: Systematic review of antimicrobial lock therapy for prevention of central-line-associated bloodstream infections in adult and pediatric cancer patients. International Journal of Antimicrobial Agents 2017, 50(3):308-317.

Manges AR, J. R. Johnson, B. Foxman, T. T. O'Bryan, K. E. Fullerton, and L. W. Riley: Widespread distribution of urinary tract infections caused by a multidrug-resistant Escherichia coli clonal group. New England Journal of Medicine 2001, 345:1007-1013.

Mobley HL, D. M. Green, A. L. Trifillis, D. E. Johnson, G. R. Chippendale, C. V. Lockatell, B. D. Jones, and J. W. Warren: Pyelonephritogenic Escherichia coli and killing of cultured human renal proximal tubular epithelial cells: role of hemolysin in some strains. Infection and Immunity 1990, 58:1281-1289.

Lake JG, Weiner LM, Milstone AM, Saiman L, Magill SS, See I: Pathogen distribution and antimicrobial resistance among pediatric healthcare-associated infections reported to the national healthcare safety network, 2011-2014. Infect Control Hosp Epidemiol 2018, 39(1):1-11.

Corkum KS, Jones RE, Reuter CH, Kociolek LK, Morgan E, Lautz TB: Central venous catheter salvage in children with Staphylococcus aureus central line-associated bloodstream infection. Pediatr Surg Int 2017, 33(11):1201-1207.

Moon HM, Kim S, Yun KW, Kim HY, Jung SE, Choi EH, Lee HJ: Clinical characteristics and risk factors of long-term central venous catheter-associated bloodstream infections in children. Pediatr Infect Dis J 2017.

Looney AT, Redmond EJ, Davey NM, Daly PJ, Troy C, Carey BF, Cullen IM: Methicillin-resistant Staphylococcus aureus as a uropathogen in an Irish setting. Medicine (Baltimore) 2017, 96(14):e4635.

Li X, Yan Z, Xu J: Quantitative variation of biofilms among strains in natural populations of Candida albicans. Microbiology 2003, 149(Pt 2):353-362.

Pruess BM, Verma K, Samanta P, Sule P, Kumar S, Wu J, Christianson D, Horne SM, Stafslien SJ, Wolfe AJ et al: Environmental and genetic factors that contribute to Escherichia coli K-12 biofilm formation. Arch Microbiol 2010, 192(9):715-728.

G. Gosheger et al., Biomaterials 25, 5547 (2004).

K. Ivanova, et al., ACS Appl. Mater. Interfaces. 7, 27066 (2015).

C.Y. Loo, et al., J. Agric. Food Chem. (2015).

M. Moscoso, E. Garcia, R. Lopez, Int. Microbiol. 12, 77 (2009).

T.J. Pritchard, K.J. Flanders, C.W. Donnelly, Int. J. Food Microbiol. 26, 375 (1995).

G. Brightwell, J. Boerema, J. Mills, E. Mowat, D. Pulford, Int. J. Food Microbiol. 109, 47 (2006).

R. Girard et al., J. Hosp. Infect. 90, 240 (2015).

E.C. Murray, A. Marek, P.C. Thomson, J.E. Coia, Nephrol. Dial. Transplant. 30, 1202 (2015).

R. Djeribi, W. Bouchloukh, T. Jouenne, B. Menaa, Am. J Infect Control 40, 854 (2012).

L. Cerqueira, J. A. Oliveira, A. Nicolau, N. F. Azevedo, M. J. Vieira, Biofouling 29, 829 (2013).

H.S. Choe et al., Int. Urol. Nephrol. 45, 743 (2013).

S. Chatterjee, P. Maiti, R. Dey, A. Kundu, R. Dey, Ann. Med. Health Sci. Res. 4, 100 (2014).

R. Zhou et al., Invest Ophthalmol. Vis. Sci 53, 7382 (2012).

A. Pinna, D. Usai, L. A. Sechi, A. Carta, S. Zanetti, Acta Ophthalmol. 89, 382 (2011).

E. Hurrell, E. Kucerova, M. Loughlin, J. Caubilla-Barron, S. J. Forsythe, Int. J Food Microbiol 136, 227 (2009).

U. Hagg, P. Kaveewatcharanont, Y. H. Samaranayake, L. P. Samaranayake, Eur. J. Orthodont. 26, 623(2004).

R. Gundelley, G. W. Youm, Y. M. Kwon, J. Rapid Meth. Automat. Microbiol. 15, 259 (2007).

(56) References Cited

OTHER PUBLICATIONS

L.S. Casarin et al., Int. J. Food Microbiol. 191, 103 (2014).
D.C. De Oliveira et al., Foodborne. Pathog. Dis. 11, 478 (2014).
R.A. Multari, D.A. Cremers, J.A. Dupre, J.E. Gustafson, J. Agric. Food Chem. 61, 8687 (2013).
D.M. Staskel, M.E. Briley, L.H. Field, S.S. Barth, J. Am. Diet. Assoc. 107, 854 (2007).
K.S. Venkitanarayanan, G. O. Ezeike, Y. C. Hung, M. P. Doyle, J. Food Prot. 62, 857 (1999).
N. Marouani-Gadri, G. Augier, B. Carpentier, Int. J. Food Microbiol. 133, 62 (2009).
L. Axelsson et al., J. Food Prot. 76, 1401 (2013).
G.A. Veluz, S. Pitchiah, C. Z. Alvarado, Poult. Sci. 91, 2004 (2012).
M. Rivera-Betancourt et al., J. Food Prot. 67, 295 (2004).
S. Silver, FEMS Microbiol. Rev. 27, 341 (2003).
N. Fong, L. A. Poole-Warren, A. Simmons, J. Biomed. Mater. Res. B Appl. Biomater. 101, 310 (2013).
J. Kwiecinski et al., Appl. Environ. Microbiol. 82, 394 (2015).
S. Kumari et al., J. Bacteriol. 182, 4173 (2000).
M. Kaur, V. Gupta, S. Gombar, J. Chander, T. Sahoo, Indian J. Med. Microbiol. 33, 248 (2015).
S. J. Stafslien et al., J. Comb. Chem. 8, 156 (2006).
S.J. Pamp, C. Sternberg, T. Tolker-Nielsen, Cytometry A 75, 90 (2009).
M. Irsfeld, B. M. Pruss, S. J. Stafslien, J. Basic Microbiol. 54, 1403 (2014).
Bartlett, D., Frantz, B. and Matsumura, P. (1988) Flagellar transcriptional activators FlbB and FlaI: gene sequences and 5'consensus sequences of operons under FlbB and FlaI control. Journal of bacteriology 170, 1575-1581.
Prüß, B.M., Campbell, J.W., Van Dyk, T.K., Zhu, C., Kogan, Y. and Matsumura, P. (2003) FlhD/FlhC is a regulator of anaerobic respiration and the Entner-Doudoroff pathway through induction of the methyl-accepting chemotaxis protein Aer. J Bacteriol 185, 534-543.
Viboud, G.I. and Bliska, J.B. (2005) Yersinia outer proteins: role in modulation of host cell signaling responses and pathogenesis. Annu Rev Microbiol 59, 69-89.
Young, G.M., Badger, J.L. and Miller, V.L. (2000) Motility is required to initiate host cell invasion by Yersinia enterocolitica. Infect Immun 68, 4323-4326.
Young, G.M., Smith, M.J., Minnich, S.A. and Miller, V.L. (1999) The Yersinia enterocolitica motility master regulatory operon, flhDC, is required for flagellin production, swimming motility, and swarming motility. J Bacteriol 181, 2823-2833.
Zhou, K., Zhou, L., Lim, Q., Zou, R., Stephanopoulos, G. and Too, H.P. (2011) Novel reference genes for quantifying transcriptional responses of *Escherichia coli* to protein overexpression by quantitative PCR. BMC Mol Biol 12, 18.
Amrutha, B., Sundar, K., and Shetty, P. H. (2017). Effect of organic acids on biofilm formation and quorum signaling of pathogens from fresh fruits and vegetables. Microb Pathog, 111, 156-162.
Brashears, M. M., and Chaves, B. D. (2017). The diversity of beef safety: A global reason to strengthen our current systems. Meat Science, 132, 59-71.
Cook, W. M Purchase, R., Ford, G. P., Creasy, D. M., Brantom, P. G., and Gangolli, S. D. (1992). A 28-day feeding study with ethyl acetoacetate in rats. Food Chem Toxicol, 30(7), 567-573.
Gardner, G. A. (1966). A selective medium for the enumeration of Microbacterium thermosphactum in meat and meat products. Journal of Applied Bacteriology, 29(3), 455-460.
Gautheron, P., Giroux, J., Cottin, M., Audegond, L., Morilla, A., Mayordomo-Blanco, L., and Spielmann, H. (1994). Interlaboratory assessment of the bovine corneal opacity and permeability (BCOP) assay. Toxicol In Vitro, 8(3), 381-392.
Gill, A., and Huszczynski, G. (2016). Enumeration of *Escherichia coli* O157:H7 in outbreak-associated beef patties. J Food Prot, 79(7), 1266-1268. doi:10.4315/0362-028X.JFP-15-521.
Gill, C. O. (1976). Substrate limitation of bacterial growth at meat surfaces. Journal of Applied Bacteriology, 41(3), 401-410.
Holzapfel, W. H. (1998). The Gram-positive bacteria associated with meat and meat products. In R. G. D. Board, A. R. (Ed.), The microbiology of meat and poultry. London, United Kingdom: Blackie Academic and Professional.
Horne, S. M., Schroeder, M., Murphy, J., and Prüß, B. M. (2018). Acetoacetate and ethyl acetoacetate as novel inhibitors of bacterial biofilm. Lett. Appl. Microbiol., 66, 329-339.
Hoyle Parks, A. R., Brashears, M. M., Woerner, W. D., Martin, J. N., Thompson, L. D., and Brooks, J. C. (2012). Spoilage characteristics of traditionally packaged ground beef with added lactic acid bacteria displayed at abusive temperatures. Journal Animal Sciences, 90, 642-648.
Ishidate, M., Jr., Sofuni, T., Yoshikawa, K., Hayashi, M., Nohmi, T., Sawada, M., and Matsuoka, A. (1984). Primary mutagenicity screening of food additives currently used in Japan. Food Chem Toxicol, 22(8), 623-636.
Jackson, L. S. (2009). Chemical food safety issues in the United States: past, present, and future. Journal Agricultural and Food Chemistry, 57(18), 8161-8170.
Koutsoumanis, K., Stamatiou, A., Skandamis, P., and Nychas, G. J. (2006). Development of a microbial model for the combined effect of temperature and pH on spoilage of ground meat, and validation of the model under dynamic temperature conditions. Applied and Environmental Microbiology, 72(1), 124-134.
Li, Q., and Logue, C. M. (2005). The growth and survival of *Escherichia coli* O157:H7 on minced bison and pieces of bison meat stored at 5 and 10oC. Food Microbiology, 22, 415-421.
Marques, L. R., Moore, M. A., Wells, J. G., Wachsmuth, I. K., and O'Brien, A. D. (1986). Production of shiga-like toxin by *Escherichia coli*. J. Infect Dis., 154(2), 338-341.
Mead, G. C., and Adams, B. W. (1977). A selective medium for the rapid isolation of pseudomonads associated with poultry meat spoilage. British Poultry Science, 18(6), 661-670.
Mossel, D. A., Mengerink, W. H., and Scholts, H. H. (1962). Use of a modified MacConkey agar medium for the selective growth and enumeration of Enterobacteriaceae. Journal of Bacteriology, 84, 381.
Nychas, G. J., Dillon, V. M., and Board, R. G. (1988). Glucose, the key substrate in the microbiological changes occurring in meat and certain meat products. Biotechnology and Applied Biochemistry, 10(3), 203-231.
Parks, A. R., Brashears, M. M., Woerner, W. D., Martin, J. N., Thompson, L. D., and Brooks, J. C. (2012). Spoilage characteristics of ground beef with added lactic acid bacteria and rosemary oleoresin packaged in a modified-atmosphere package and displayed at abusive temperatures. Journal of Animal Sciences, 90(6), 2054-2060.
Radha Krishnan, K., Babuskin, S., Azhagu Saravana Babu, P., Sasikala, M., Sabina, K., Archana, G., and Sukumar, M. (2014). Antimicrobial and antioxidant effects of spice extracts on the shelf life extension of raw chicken meat. Int J Food Microbiol, 171, 32-40. doi:10.1016/j.ijfoodmicro.2013.11.011.
Reid, R., Fanning, S., Whyte, P., Kerry, J., and Bolton, D. (2017). Comparison of hot versus cold boning of beef carcasses on bacterial growth and the risk of blown pack spoilage. Meat Sci, 125, 46-52. doi:10.1016/j.meatsci.2016.11.012.
Remenant, B., Jaffres, E., Dousset, X., Pilet, M. F., and Zagorec, M. (2015). Bacterial spoilers of food: behavior, fitness and functional properties. Food Microbiology, 45, 45-53.
Rogers, H. B., Brooks, J. C., Martin, J. N., Tittor, A., Miller, M. F., and Brashears, M. M. (2014). The impact of packaging system and temperature abuse on the shelf life characteristics of ground beef. Meat Sci, 97(1), 1-10.
Seys, S. A., Sampedro, F., and Hedberg, C. W. (2016). Factors associated with recovery of meat products following recalls due to Shiga toxin-producing *Escherichia coli*. Epidemiol Infect, 144(14), 2940-2947. doi:10.1017/S0950268816001266.
Stanbridge, L. H. D., A.R. (1998). The microbiology of chill-stored meat. In R. G. D. Board, A.R. (Ed.), The microbiology of meat and poultry. London, United Kingdom: Blackie Academic and Professional.

(56) References Cited

OTHER PUBLICATIONS

Sule, P., Horne, S. M., Logue, C. M., and Prüß, B. M. (2011). Regulation of cell division, biofilm formation, and virulence by FlhC in *Escherichia coli* O157:H7 grown on meat. Applied and Environmental Microbiology, 77(11), 3653-3662.

Tamminen, L. M., Fransson, H., Traven, M., Aspan, A., Alenius, S., Emanuelson, U., and Eriksson, E. (2018). Effect of on-farm interventions in the aftermath of an outbreak of hypervirulent verocytotoxin-producing *Escherichia coli* O157:H7 in Sweden. Vet Rec, 182(18), 516. doi:10.1136/vr.104223.

Taormina, P. J., and Beuchat, L. R. (1999). Comparison of chemical treatments to eliminate enterohemorrhagic *Escherichia coli* O157:H7 on alfalfa seeds. Journal of Food Protection, 62(4), 318-324.

Torso, L. M., Voorhees, R. E., Forest, S. A., Gordon, A. Z., Silvestri, S. A., Kissler, B., and Harrison, L. H. (2015). *Escherichia coli* O157:H7 outbreak associated with restaurant beef grinding. J Food Prot, 78 (7), 1272-1279. doi:10.4315/0362-028X.JFP-14-545.

Vangay, P., Fugett, E. B., Sun, Q., and Wiedmann, M. (2013). Food microbe tracker: a web-based tool for storage and comparison of food-associated microbes. Journal of Food Protection, 76(2), 283-294. doi:10.

Wameadesa, N., Sae-Lim, A., Hayeebilan, F., Rattanachuay, P., and Sukhumungoon, P. (2017). Enteroaggregative *Escherichia coli* O104 from thai and imported Malaysian raw beef. Southeast Asian J Trop Med Public Health, 48(2), 338-350.

White, A., Cronquist, A., Bedrick, E. J., and Scallan, E. (2016). Food source prediction of shiga toxin-producing *Escherichia coli* outbreaks using demographic and outbreak characteristics, United States, 1998-2014. Foodborne Pathog Dis, 13(10), 527-534. doi:10.1089/fpd.2016.2140.

Yoo, Y. S. (1986). Mutagenic and antimutagenic activities of flavoring agents used in foodstuffs. J Osaka City Med Cent, 34, 267-288.

Mermel LA, Allon M, Bouza E, Craven DE, Flynn P, O'Grady NP, Raad, II, Rijnders BJ, Sherertz RJ, Warren DK: Clinical practice guidelines for the diagnosis and management of intravascular catheter-related infection: 2009 Update by the Infectious Diseases Society of America. Clin Infect Dis 2009, 49(1):1-45.

Luppens SB, Reij MW, Van Der Heijden RW, Rombouts FM, Abee T: Development of a standard test to assess the resistance of *Staphylococcus aureus* biofilm cells to disinfectants. Applied and environmental microbiology 2002, 68(9):4194-4200.

Spoering AL, Lewis K: Biofilms and planktonic cells of Pseudomonas aeruginosa have similar resistance to killing by antimicrobials. J Bacteriol 2001, 183(23):6746-6751.

Stewart PS, Rayner J, Roe F, Rees WM: Biofilm penetration and disinfection efficacy of alkaline hypochlorite and chlorosulfamates. J Appl Microbiol 2001, 91(3):525-532.

Lemaster CH, Schuur JD, Pandya D, Pallin DJ, Silvia J, Yokoe D, Agrawal A, Hou PC: Infection and natural history of emergency department-placed central venous catheters. Ann Emerg Med 2010, 56(5):492-497.

Tarai B DP, and Kumar D: Recurrent Challenges for Clinicians: Emergence of Methicillin-Resistant *Staphylococcus aureus*, Vancomycin Resistance, and Current Treatment Options. Journal of Laboratory Physicians 2013, 5(2): 71-78.

Casey AL ML, Nightingale P, Elliott TS: Antimicrobial central venous catheters in adults: a systematic review and meta-analysis. The Lancet Infectious Diseases 2008, 8(12):763-776.

Choi YJ, Lim JK, Park JJ, Huh H, Kim DJ, Gong CH, Yoon SZ: Chlorhexidine and silver sulfadiazine coating on central venous catheters is not sufficient for protection against catheter-related infection: Simulation-based laboratory research with clinical validation. The Journal of international medical research 2017, 45(3):1042-1053.

Chen Y-M, Dai A-P, Shi Y, Liu Z-J, Gong M-F, Yin X-B: Effectiveness of silver-impregnated central venous catheters for preventing catheter-related blood stream infections: a meta-analysis. International Journal of Infectious Diseases 2014, 29:279-286.

Knetsch Mlwak, L.H.: New Strategies in the Development of Antimicrobial Coatings: The Example of Increasing Usage of Silver and Silver Nanoparticles. Polymers 2011, 3(1):340-366.

Palza H: Antimicrobial Polymers with Metal Nanoparticles. International Journal of Molecular Science 2015, 16:2099-2116.

Ballo MK, Rtimi S, Pulgarin C, Hopf N, Berthet A, Kiwi J, Moreillon P, Entenza JM, Bizzini A: In vitro and in vivo effectiveness of an innovative silver-copper nanoparticle coating of catheters to prevent methicillin-resistant *Staphylococcus aureus* Infection. Antimicrob Agents Chemother 2016, 60(9):5349-5356.

Graves JL, Jr., Tajkarimi M, Cunningham Q, Campbell A, Nonga H, Harrison SH, Barrick JE: Rapid evolution of silver nanoparticle resistance in *Escherichia coli*. Front Genet 2015, 6:42.

\* cited by examiner

FIG. 1G  FIG. 1H

SEQUENCE LISTING

```
<160> NUMBER OF SEQ ID NOS: 16

<210> SEQ ID NO 1
<211> LENGTH: 20
<212> TYPE: DNA
<213> ORGANISM: Artificial Sequence
<220> FEATURE:
<223> OTHER INFORMATION: primer

<400> SEQUENCE: 1
catcatctgg tgcatcaagg                                                   20

<210> SEQ ID NO 2
<211> LENGTH: 20
<212> TYPE: DNA
<213> ORGANISM: Artificial Sequence
<220> FEATURE:
<223> OTHER INFORMATION: primer

<400> SEQUENCE: 2
ttacacagca tcacgttagc                                                   20

<210> SEQ ID NO 3
<211> LENGTH: 21
<212> TYPE: DNA
<213> ORGANISM: Artificial Sequence
<220> FEATURE:
<223> OTHER INFORMATION: primer

<400> SEQUENCE: 3
cgcagcagag acaatacagt t                                                 21

<210> SEQ ID NO 4
<211> LENGTH: 22
<212> TYPE: DNA
<213> ORGANISM: Artificial Sequence
```

<220> FEATURE:
<223> OTHER INFORMATION: primer

<400> SEQUENCE: 4
tgaacaatac cgtgaacaac ct                                    22

<210> SEQ ID NO 5
<211> LENGTH: 25
<212> TYPE: DNA
<213> ORGANISM: Artificial Sequence
<220> FEATURE:
<223> OTHER INFORMATION: primer

<400> SEQUENCE: 5
acgaactttc tgacgatgag ctgga                                 25

<210> SEQ ID NO 6
<211> LENGTH: 25
<212> TYPE: DNA
<213> ORGANISM: Artificial Sequence
<220> FEATURE:
<223> OTHER INFORMATION: primer

<400> SEQUENCE: 6
tgtgagttca gctaagcggt ggtct                                 25

<210> SEQ ID NO 7
<211> LENGTH: 20
<212> TYPE: DNA
<213> ORGANISM: Artificial Sequence
<220> FEATURE:
<223> OTHER INFORMATION: primer

<400> SEQUENCE: 7
agttggtgtc aatgtcgctg                                       20

<210> SEQ ID NO 8
<211> LENGTH: 21
<212> TYPE: DNA
<213> ORGANISM: Artificial Sequence
<220> FEATURE:
<223> OTHER INFORMATION: primer

<400> SEQUENCE: 8
actgcgctac tgctcattta c                                     21

<210> SEQ ID NO 9
<211> LENGTH: 22
<212> TYPE: DNA
<213> ORGANISM: Artificial Sequence
<220> FEATURE:
<223> OTHER INFORMATION: primer

<400> SEQUENCE: 9
gccgaatctc ccaatgcctt ac                                    22

<210> SEQ ID NO 10
<211> LENGTH: 21
<212> TYPE: DNA
<213> ORGANISM: Artificial Sequence
<220> FEATURE:
<223> OTHER INFORMATION: primer

<400> SEQUENCE: 10
cggttggtgc tagtgctgaa g                                     21

```
<210> SEQ ID NO 11
<211> LENGTH: 22
<212> TYPE: DNA
<213> ORGANISM: Artificial Sequence
<220> FEATURE:
<223> OTHER INFORMATION: primer

<400> SEQUENCE: 11
cgtcttttaa cgatagctcg tg                                              22

<210> SEQ ID NO 12
<211> LENGTH: 20
<212> TYPE: DNA
<213> ORGANISM: Artificial Sequence
<220> FEATURE:
<223> OTHER INFORMATION: primer

<400> SEQUENCE: 12
aacgatgaga aagcctcagc                                                 20

<210> SEQ ID NO 13
<211> LENGTH: 21
<212> TYPE: DNA
<213> ORGANISM: Artificial Sequence
<220> FEATURE:
<223> OTHER INFORMATION: primer

<400> SEQUENCE: 13
ctacaagggt ggaaactaag c                                               21

<210> SEQ ID NO 14
<211> LENGTH: 22
<212> TYPE: DNA
<213> ORGANISM: Artificial Sequence
<220> FEATURE:
<223> OTHER INFORMATION: primer

<400> SEQUENCE: 14
attggtgagc atagagaata cg                                              22

<210> SEQ ID NO 15
<211> LENGTH: 22
<212> TYPE: DNA
<213> ORGANISM: Artificial Sequence
<220> FEATURE:
<223> OTHER INFORMATION: primer

<400> SEQUENCE: 15
gatcgcggcg aagtagtatt ag                                              22

<210> SEQ ID NO 16
<211> LENGTH: 22
<212> TYPE: DNA
<213> ORGANISM: Artificial Sequence
<220> FEATURE:
<223> OTHER INFORMATION: primer

<400> SEQUENCE: 16
gcttgctgaa tctgctgtaa ac                                              22
```

BIOFILM INHIBITOR AND METHOD OF INHIBITING BIOFILM

RELATED APPLICATIONS

This application claims the benefit of U.S. Provisional Application Ser. No. 62/561,353, filed Sep. 21, 2017, the entire disclosure of which is incorporated herein by this reference.

GOVERNMENT INTEREST

This invention was made with government support under Hatch Act Project Number ND02236 (grant number 1009422), and grant numbers 2009-35201-05010 and 2012-67006-19659, awarded from the United States Department of Agriculture/National Institute of Food and Agriculture (USDA/NIFA). The government has certain rights in the invention.

TECHNICAL FIELD

The present invention relates to biofilm inhibitors and methods of inhibiting biofilms. In particular, the presently-disclosed subject matter relates to ethylacetoacetic acid as a biofilm inhibitor and methods of inhibiting biofilms using ethylacetoacetic acid.

BACKGROUND

Bacterial biofilms are communities of bacteria that form on surfaces. In these communities, the bacteria are embedded in a self-produced 'glue' that keeps them tightly bound to each other and to the surface. This makes the biofilm bound bacteria very hard to remove by physical, chemical, or biological means, which includes antibiotics and the host immune system. Although biofilms are naturally occurring and can be beneficial in certain situations, due to these characteristics, biofilm associated bacteria also contribute to many clinical, industrial, natural, environmental, and food processing problems.

For example, indwelling urinary catheters have an infection rate of up to 30% and infection by bacterial pathogens is the second most common cause of death in renal replacement patients. One of the most significant hospital-acquired infections a patient may face includes catheter-associated bloodstream infections (CABSIs). Not only are these infections dangerous to those who contract them, they pull resources away from other patients and significantly raise the cost of care. More specifically, in addition to the attributable morbidity and mortality these infections may cause, CABSI increases the cost of care per patient by an average of $15,000-$56,000.

CABSIs and other infections that often involve biofilm associated bacteria also present reimbursement issues for healthcare providers. In particular, under new healthcare reform rules, the Center for Medicare and Medicaid Services (CMS) no longer reimburses hospitals for those added costs of infections such as CABSIs if they were acquired after a patient arrives. Additionally, if the hospital's rate of CABSIs is deemed too high, CMS may penalize hospital reimbursement through value-based purchasing penalties and/or the hospital-acquired condition reduction penalties. Furthermore, CMS now uses public reporting of hospital infection rates to incentivize better care. Accordingly, it is imperative for healthcare institutions to reduce the incidence of CABSIs through better processes and care, and to find technological solutions to effectively prevent and treat CABSIs.

Turning to the food processing industry, in another example, bacterial biofilms can facilitate outbreaks of foodborne illness. Microorganisms, including pathogens, can be naturally found in the intestinal tract of livestock, such as cattle, poultry, pigs, and seafood. Such pathogens can be spread to other livestock when they are shed through feces and contaminate the soil and water in their environment. If they are not properly disinfected prior to slaughter, these infected animals can then transmit bacterial pathogens to equipment, surfaces, and containers used in different stages of the process. The transmitted bacteria can further spread to previously uninfected surfaces via biofilm formation, leading to outbreaks of infectious disease. Many bacterial pathogens have been associated with foodborne illnesses, such as *Pseudomonas* spp., *S. marcescens*, *E. coli* spp., and *S. simulans*. These bacteria strains have been identified as bacteria that can attach to the polyurethane and polyvinylchloride surfaces that line the conveyor belts used during different stages in food processing.

Annually it is estimated that 48 million Americans ingest bacteria contaminated food that results in illness and costs $77.7 billion in health care costs, workers compensation, and loss of product. Foodborne outbreaks have resulted in 300,000 hospitalizations and up to 5,000 deaths per year due to illness. The problem of foodborne outbreaks is compounded by the increasing emergence of antibiotic resistant bacteria due to the overuse of antibiotics, which can be added to the animal feed and have even been used in fisheries for prevention and treatment of diseases. More importantly sub therapeutic doses of antibiotics have been shown to enhance growth of the animals, making it an attractive option for farmers. Overall, this has contributed to the increased likelihood for consumers to ingest food contaminated with bacterial pathogens.

In view of these and other problems, much research has been done to prevent the formation of microbial biofilms on surfaces. One strategy to minimize bacterial biofilm is to incorporate silver-based compounds that exhibit anti-microbial activity. However, these materials are accompanied by high production costs, limited lifetimes, and the development of silver resistant bacteria. Another strategy includes coating of implants with a tissue plasminogen activator. Although this coating was effective against *S. aureus*, other pathogens were not tested.

More recently, researchers have advanced from conventional approaches that were aimed at killing the bacteria to modulating bacteria into behaviors that are less harmful to humans. Combinations of these two approaches have been proposed as well. One such example includes the use of quorum sensing inhibitors to prevent dental biofilm. However, despite recent technological advances, biofilm formation still contributes to 60 to 80% of human bacterial infections (NIH and CDC) and cause problems in many natural, environmental, bioindustrial, and food processing settings. Together with the emergence of antibiotic resistant bacterial strains, biofilm continues to make treating these types of infections difficult. As a result of these difficulties, it is estimated that biofilms continue to cost the U.S. billions of dollars annually.

Accordingly, there is a need for substances and methods that inhibit biofilm without increasing the virulence of the bacteria.

SUMMARY

This summary describes several embodiments of the presently-disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this summary or not. To avoid excessive repetition, this summary does not list or suggest all possible combinations of features.

The presently-disclosed subject matter provides, in some embodiments, a biofilm inhibiting composition including a fluid and at least one biofilm inhibiting compound selected from the group consisting of acetoacetate (AAA) and ethyl acetoacetate (EAA). In one embodiment, the biofilm inhibiting compound is EAA. In one embodiment, the biofilm inhibiting compound is dissolved in the fluid. In one embodiment, the biofilm inhibiting compound is dispersed in the fluid.

Also provided herein, in some embodiments, is a biofilm inhibiting article including a substrate and at least one biofilm inhibiting compound selected from the group consisting of AAA and EAA. In one embodiment, the biofilm inhibiting compound is EAA. In one embodiment, the substrate includes polyurethane, silicone hydrogel, polyvinylchloride, acrylic, polyester, nylon, polycarbonate, polypropylene, or silicone. In another embodiment, the substrate is modified with β-phenylethylamine (PEA). In one embodiment, the biofilm inhibiting compound is embedded in the substrate. In one embodiment, the biofilm inhibiting compound is positioned over the substrate. In one embodiment, the article comprises tubing. In another embodiment, the tubing includes a catheter, tubing arranged and disposed to transport a beverage, tubing arranged and disposed for use in plumbing, or tubing arranged and disposed to transport sewage.

Further provided herein, in some embodiments, is a method of reducing planktonic bacterial growth or biofilm formation, the method comprising providing a biofilm inhibiting compound selected from the group consisting of acetoacetate (AAA) and ethyl acetoacetate (EAA) and contacting an article with the biofilm inhibiting compound. In one embodiment, the biofilm inhibiting compound is dissolved or dispersed in a fluid to form a biofilm inhibiting solution. In another embodiment, the article is a food item. In a further embodiment, contacting the article with the biofilm inhibiting compound comprises mixing the food item with the biofilm inhibiting solution. In a further embodiment, the food item comprises raw meat. In another embodiment, the article comprises tubing. In a further embodiment, contacting the article with the biofilm inhibiting compound comprises flushing the tubing with the biofilm inhibiting solution. In a further embodiment, the article comprises a catheter.

BRIEF DESCRIPTION OF THE DRAWINGS

The presently-disclosed subject matter will be better understood, and features, aspects and advantages other than those set forth above will become apparent when consideration is given to the following detailed description thereof. Such detailed description makes reference to the following drawings, wherein:

FIGS. 1A-H show graphs illustrating the effect of AAA on planktonic growth and biofilm amounts of (A-B) *C. sakazakii* (37° C.), (C-D) *S. marcescens* (30° C.), (E-F) *Y. enterocolitica* (25° C.), and (G-H) *Y. enterocolitica* (37° C.). For all graphs, squares indicate planktonic growth, expressed as maximal velocity of $OD_{600}$; triangles represent biofilm amounts as determined by the CV assay, expressed as $OD_{600}$; and diamonds are used for the ATP assays, expressed as RLU. Averages were calculated over six replicates. Errors indicate one standard deviation.

Figure 1A:
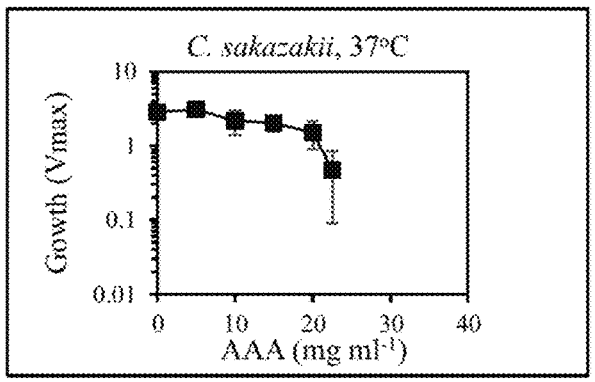

While the disclosure is susceptible to various modifications and alternative forms, specific embodiments thereof have been shown by way of example in the drawings and are herein described below in detail. It should be understood, however, that the description of specific embodiments is not intended to limit the disclosure to cover all modifications, equivalents and alternatives falling within the spirit and scope of the disclosure as defined by the appended claims.

Definitions

Unless defined otherwise, all technical and scientific terms used herein have the same meaning as commonly understood by one of ordinary skill in the art to which the disclosure belongs. In the event that there are a plurality of definitions for terms herein, those in this section prevail. Where reference is made to a URL or other such identifier or address, it understood that such identifiers can change and particular information on the internet can come and go, but equivalent information can be found by searching the internet. Reference thereto evidences the availability and public dissemination of such information.

Following long-standing patent law convention, the terms "a," "an," and "the" refer to "one or more" when used in this application, including the claims. Thus, for example, reference to "a cell" includes a plurality of cells, and so forth.

The terms "comprising," "including," and "having" are intended to be inclusive and mean that there may be additional elements other than the listed elements.

Unless otherwise indicated, all numbers expressing quantities of ingredients, properties such as reaction conditions, and so forth used in the specification and claims are to be understood as being modified in all instances by the term "about." Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration, percentage, or the like is meant to encompass variations of in some embodiments ±50%, in some embodiments ±40%, in some embodiments ±30%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself.

For example, if the value "10" is disclosed, then "about 10" is also disclosed. It is also understood that each unit between two particular units are also disclosed. For example, if 10 and 15 are disclosed, then 11, 12, 13, and 14 are also disclosed.

All combinations of method or process steps as used herein can be performed in any order, unless otherwise specified or clearly implied to the contrary by the context in which the referenced combination is made.

DETAILED DESCRIPTION

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. Therefore, although any methods, devices, and materials similar or equivalent to those described herein can be used in the practice or testing of the presently-disclosed subject matter, representative methods, devices, and materials are now described. In case of conflict, the specification of this document, including definitions, will control.

The presently-disclosed subject matter relates to compositions, devices, and methods for inhibiting biofilm bound bacteria and/or planktonic bacteria (referred to herein as biofilm inhibiting compounds). In some embodiments, the compositions include one or more biofilm inhibiting compounds that reduce or prevent the formation of biofilm while being recognized by bacteria as a nutrient or food. In one embodiment, suitable biofilm inhibiting compounds include acetoacetate (AAA) containing compounds, such as, but not limited to, AAA, ethyl acetoacetate (EAA), or a combination thereof. In another embodiment, the biofilm inhibiting compounds include EAA. In a further embodiment, as compared to AAA, EAA provides increased biofilm inhibition, is an effective biofilm inhibitor at lower concentrations, and/or provides biofilm inhibition at reduced cost.

In some embodiments, the biofilm inhibiting compounds are incorporated in any suitable fluid and/or semisolid. For example, in one embodiment, the biofilm inhibiting compounds are dissolved or dispersed in a liquid, such as, but not limited to, water, bacterial growth media (e.g., tryptic soy broth, brucella broth, or similar), bodily fluids (e.g., tears, saliva, blood, or similar), baby formula, or a combination thereof. In another embodiment, the liquid may be formulated as a spray. In a further embodiment, the biofilm inhibiting compounds are dissolved or dispersed in a gel or cream.

The biofilm inhibiting compounds may be dissolved or dispersed in any suitable concentration for inhibiting or reducing biofilm growth. Suitable concentrations for AAA include, but are not limited to, at least about 1 mg/ml, up to about 100 mg/ml, up to about 50 mg/ml, between about 1 mg/ml and about 40 mg/ml, between about 5 mg/ml and about 40 mg/ml, between about 10 mg/ml and about 40 mg/ml, between about 10 mg/ml and about 35 mg/ml, between about 10 mg/ml and about 30 mg/ml, between about 10 mg/ml and about 20 mg/ml, between about 20 mg/ml and about 30 mg/ml, or any combination, sub-combination, range, or sub-range thereof. Suitable concentrations for EAA include, but are not limited to, at least about 0.01 mg/ml, at least about 0.05 mg/ml, at least about 0.1 mg/ml, up to about 100 mg/ml, up to about 50 mg/ml, up to about 25 mg/ml, between about 0.01 mg/ml and about 20 mg/ml, between about 0.05 mg/ml and about 20 mg/ml, between about 0.1 mg/ml and about 20 mg/ml, between about 0.01 mg/ml and about 15 mg/ml, between about 0.05 mg/ml and about 15 mg/ml, between about 0.1 mg/ml and about 15 mg/ml, between about 0.01 mg/ml and about 10 mg/ml, between about 0.05 mg/ml and about 10 mg/ml, between about 0.1 mg/ml and about 10 mg/ml, between about 0.1 mg/ml and about 9 mg/ml, between about 0.1 mg/ml and about 8 mg/ml, between about 0.1 mg/ml and about 7 mg/ml, between about 0.1 mg/ml and about 6 mg/ml, or any combination, sub-combination, range, or sub-range thereof. In certain embodiments, for example, the EAA concentration is between about 0.2 mg/ml and about 6 mg/ml.

Additionally or alternatively, the biofilm inhibiting compounds may be incorporated in, positioned over, and/or embedded within a substrate. Suitable substrates include, but are not limited to, thermosetting polymers (e.g., polyester, polyurethane, silicone, etc.), thermoplastic polymers (e.g., acrylic, nylon, polycarbonate, polypropylene, polyvinyl-chloride, etc.), hydrogels (e.g., silicone hydrogels), or a combination thereof. In one embodiment, for example, the substrate includes polyurethane and/or silicone. In another embodiment, the polyurethane and/or silicone is infused with β-phenylethylamine (PEA) at a concentration of up to 25%, up to 20%, up to 15%, up to 10%, between 1% and 10%, between 2% and 8%, between 3% and 7%, between 4% and 6%, about 5%, or any combination, sub-combination, range, or sub-range thereof. Although described above with respect to PEA infusion, as will be appreciated by those skilled in the art, the disclosure is not so limited and may be devoid of any additional compounds or may include any other suitable nutrient/compound in addition to or in place thereof.

In some embodiments, the substrate and the biofilm inhibiting compound(s) form a device and/or article. The device/article may include any suitable device/article where bacterial contamination/growth is possible. In one embodiment, the device/article is a medical and/or clinical device/article. As used herein, the term medical and/or clinical means any device/article that is used in a health care setting, including devices/articles that contact or are inserted into a human or other animal for therapeutic or treatment purposes. Such devices/articles include, but are not limited to, catheters (e.g., urinary, heart), feeding tubes, other devices/articles that transport fluids (e.g., tubing), any other device/article used in a health care setting, or a combination thereof. In one embodiment, the device/article is a food processing device/article. As used herein, the term food processing device/article means any device/article involved in or located in an area where food items are processed, transported, and/or maintained. Such devices/articles include, but are not limited to, conveyor belts, tubing for transporting liquids or other flowable food items, brewing devices/articles, beverage devices/articles, or a combination thereof. In one embodiment, the device/article is a plumbing or sewage device/article, such as, but not limited to, tubing or piping that transports water to and/or waste from one location to another.

The at least one biofilm inhibiting compound may be incorporated in and/or on the substrate/device/article in any suitable concentration. As will be appreciated by those skilled in the art, the concentration will vary depending upon the substrate/article/device being formed as well as the particular biofilm inhibiting compound being incorporated. For example, due to the increased efficacy discussed above, EAA may be incorporated at decreased concentrations as compared to AAA. In some embodiments, the decreased amounts of EAA as compared to AAA provide increased biofilm inhibition without decreasing or negatively impacting the mechanical properties of the substrate in which the EAA is being incorporated. Additionally or alternatively, as compared to catheter tubes and other devices/articles that are inserted or implanted within the body, conveyer belts and other devices/articles that are not inserted or implanted within the body may include increased concentrations of the biofilm inhibiting compound. In one embodiment, the increased concentration of biofilm inhibiting compound provides a longer duration of effectiveness. In another embodiment, this increased duration of effectiveness is desired for devices/articles that are not implanted or inserted within the body where, unlike implanted or inserted devices/articles, there is no immune system to adequately clear the infection after a period of time.

Without wishing to be bound by theory, it is believed that chemicals which are both biofilm inhibiting and recognized by bacteria as a nutrient decrease the risk of bacterial resistance and/or increase the amount of time required to develop such resistance. Additionally, the biofilm inhibiting compounds disclosed herein provide biofilm inhibition for a wide range of bacteria. For example, in certain embodiments, the biofilm inhibiting compounds reduce or prevent biofilm formation by bacteria such as, but not limited to, *Staphylococcus aureus, Pseudomonas aeruginosa, E. coli, Cronobacter sakazakii, Serratia marcescens, Yersinia enterocolitica*, other species from the genus *Yersiniae*, other Enterobacteriaceae, other gram-negative bacteria, or a combination thereof. The biofilm inhibiting compounds disclosed herein also provide biofilm inhibition at reduced cost as compared to existing materials, such as silver. Furthermore, by reducing or preventing the formation of biofilms instead of removing biofilms once they are detected, the biofilm inhibiting compounds reduce both the costs associated with biofilm formation (e.g., reduced incidence of infection, reduced biocorrosion, reduced equipment damage, and reduced product contamination) as well as the direct and indirect (e.g., labor, equipment down time) costs of biofilm removal. Accordingly, the biofilm inhibiting compounds may be employed in a variety of different applications, including, but not limited to, food, clinical, and/or industrial applications.

Also provided herein are methods of reducing or inhibiting bacterial growth and/or biofilm formation. In some embodiments, the method includes contacting an article with one or more of the biofilm inhibiting compounds. The contacting may include integrating the biofilm inhibiting compound(s) as the article is formed, coating the article with the biofilm inhibiting compound(s), and/or applying a fluid containing the biofilm inhibiting compound(s) to the article. For example, in one embodiment, the method includes contacting a food item, such as raw meat, leafy greens, fruits, vegetables, or a combination thereof, with a liquid containing the biofilm inhibiting compound(s). In another embodiment, mixing ground beef with EAA at a concentration of at least 0.5% w/w inhibits natural microflora and bacteria, including *E. coli*, when stored at elevated temperatures for extended periods of time, thus preventing spoilage of the ground beef. Although described above with respect to an EAA concentration of at least 0.5% w/w, as will be appreciated by those skilled in the art the disclosure is not so limited and may include any other suitable concentration.

In another example, the biofilm inhibiting compounds may be dissolved or dispersed in a liquid to form a wash solution for rinsing/cleaning tubing or other components that are subject to biofilm formation in the clinical, food processing, and/or industrial fields. For example, the biofilm inhibiting compound(s) may be incorporated into an antibiotic solution that is used as a flush and/or in antibiotic-lock therapy (ALT), where the solution including the biofilm inhibiting compound(s) is left to dwell within the interior space of a tubing that transports fluid and/or where bacterial contamination/growth is possible. The biofilm inhibiting compounds may also be incorporated into a spray for cleaning countertops, surfaces of food processing equipment, medical equipment, or any other suitable surface.

In still another example, the biofilm inhibiting compounds may be embedded within and/or form a coating over a surface of an article where bacterial contamination/growth are possible. In some embodiments, the article includes tubing used to transport fluids where bacterial contamination/growth are possible. In one embodiment, the article includes tubing used in health care, such as a catheter. In one embodiment, the article includes tubing used in the food industry, such as tubing for brewing, beverage production/dispensing, or other food related tubing. In one embodiment, the article is tubing used in plumbing or sewage lines.

Further provided herein, is a method of forming a biofilm inhibiting article/device. In some embodiments, the method includes mixing one or more of the biofilm inhibiting compounds disclosed herein with a substrate material, and heat extruding the mixture to form the article/device. In one embodiment, for example, the method includes mixing EAA, AAA, and/or any other suitable biofilm inhibiting compound with a polyurethane material and then forming a catheter tube or other tubing through heat extrusion of the mixture. In another embodiment, the method includes mixing any one or more of the biofilm inhibiting compounds with polyurethane or silicone, and then forming a flat sheet for use as a conveyor belt through heat extrusion. In a further embodiment, the polyurethane material is infused with 5% w/w PEA (PU-PEA).

The presently-disclosed subject matter is further illustrated by the following specific but non-limiting examples. The following examples may include compilations of data that are representative of data gathered at various times during the course of development and experimentation related to the presently-disclosed subject matter.

EXAMPLES

Example 1

This Example is directed to a novel technique for reducing biofilm amounts of bacterial pathogens that are i) not on the top 10 list for food or hospitalizations, are ii) consequently understudied with respect to the development of novel prevention techniques, but are iii) nevertheless of increasing concern. To accomplish this, the instant inventors stepped away from the primary goal of killing the bacteria and instead focused on nutrients that provide an inhibitory effect on growth and biofilm. More specifically, 95 carbon and 95 nitrogen sources were screened for their inhibitory effect on growth and biofilm amounts of *E. coli* O157 H7, grown at 10° C. in liquid beef broth. The carbon and nitrogen sources were narrowed down to the 8 most effective, of which β-phenylethylamine (PEA) and acetoacetate (AAA) were the best. AAA and ethyl acetoacetate (EAA)

were then tested on *Cronobacter sakazakii*, *Serratia marcescens*, and *Yersinia enterocolitica*.

*Cronobacter sakazakii* is a member of the Enterobacteriaceae which exhibits an unusually high resistance towards stresses, such as dessication, osmotic pressure, and heat. This enables it to persist in varied locations, including food, households, plants, and insects. As a health concern, *C. sakazakii* has been found in powdered infant formula, where it forms a biofilm and has been associated with neonatal meningitis and necrotizing enterocolitis. *Serratia marcescens* has increasingly gained recognition as a pathogen to animals, plants, and humans. It has been associated with neonatal feeding tubes, catheter associated blood stream infections, and the question has been raised whether it may play a role in male infertility. The bacteria are highly resistant towards a variety of antibiotics. As one example, only supratherapeutic doses of chloramphenicol were effective against *S. marcescens* biofilm.

The third bacterial pathogen of this Example is *Yersinia enterocolitica*, which was also used to determine the transcription of virulence factors in response to AAA. Together with other species from the genus *Yersiniae*, *Y. enterocolitica* was proposed as a model organism for the evolution of a successful pathogen. It is transmitted via the fecal-oral route and causes yersiniosis. The virulence factors that contribute to pathogenicity of *Y. enterocolitica* have been investigated intensively. The pYV virulence plasmid contains a group of genes that encode components of the type III secretion system and are designated yop (*Yersinia* outer protein). Yop effector proteins destabilize the actin cytoskeleton and disable phagocytic cells. The yadA gene is also located on the pYV virulence plasmid. YadA is an adhesion and type V autotransporter, its absence renders the bacteria avirulent. Chromosomally encoded virulence genes include the inv gene that encodes invasin (required for the early invasion of Peyer's patches) and multiple genes encoding flagellin, a potent activator of the innate immune response. Flagellar genes and inv are activated by the flagellar master regulator FlhD/FlhC. Although researchers isolated *Y. enterocolitica* biofilm from infected children and determined that antibiotic resistance was enhanced in the biofilm, the formation of biofilm by *Y. enterocolitica* has been studied sparsely.

As discussed in detail below, it was determined that AAA reduced growth and biofilm amounts of the three pathogens, albeit at rather high concentrations of 10 to 30 mg/ml. AAA at a concentration of 5 mg/ml reduced *Y. enterocolitica* mRNA transcripts of the flagellar master regulator operon flhD, the invasion gene inv, and the adhesion gene yadA under some of the conditions tested. Transcription of the regulator of plasmid encoded virulence genes virF, the plasmid encoded virulence gene yopQ, and ymoA were largely unaffected by AAA. Importantly, AAA did not appear to cause an increase in transcription of any of the virulence genes tested.

Additionally, as a more cost effective alternative to AAA, the effect of ethyl acetoacetate (EAA) was tested on biofilm amounts of the three pathogens. EAA reduced growth and biofilm amounts up to 3 logs. In most experiments, the $IC_{50}$ was in the single digit mg/ml range. In summary, both AAA and EAA inhibit biofilm, but EAA appears to be more effective.

Materials and Methods

Bacterial Strains, Plasmids, and Growth Conditions:

*C. sakazakii* BAA-894 was isolated from powdered infant formula after a fatal neonatal case of *C. sakazakii* infection in 2001. *S. marcescens* BAA-632 was isolated from the urine of an asymptomatic adult and obtained from the American Type Culture Collection (ATCC). *Y. enterocolitica* 8081 is of the American serotypes 0:8 and causes gastroenteritis and systemic infections in humans and mice. A distinction is being made between the 8081v strain that contains the pYV virulence plasmid and the 8081c strain that has been cured of pYV. Both strains were kindly provided by Dr. Scott A. Minnich (University of Idaho, Moscow, Id.).

All bacterial stock cultures were kept at −80° C. in dimethyl sulfoxide. Prior to each experiment, the freezer stock was struck out on to Luria Bertani (LB, 10 g $l^{-1}$ tryptone, 5 g $l^{-1}$ yeast extract, 10 g $l^{-1}$ NaCl, pH 7.0) agar plates and incubated until colonies were visible. Single colonies were picked from the plates and inoculated into 10 ml of tryptic soy broth (TSB, 37.0 g $l^{-1}$ pancreatic digest of casein, 3.0 g $l^{-1}$ papaic digest of soybean, 2.5 g $l^{-1}$ dextrose, 5.0 g $l^{-1}$ sodium chloride, 2.5 g $l^{-1}$ dipotassium phosphate, pH 7.3). Cultures were incubated aerobically while shaking at 150 rpm overnight. Bacteria were pelleted from the cultures by centrifugation at 4,700 rpm at 4° C. for 10 min. Bacterial pellets were resuspended in phosphate buffered saline (PBS) to an optical density at 600 nm ($OD_{600}$) of 1.00±0.02.

The pYV virulence plasmid of *Y. enterocolitica* 8081v is prone to being lost when grown in the absence of selective pressure. Polymerase chain reaction (PCR) was performed as part of each of the experiments to detect the plasmid-encoded virF gene. PCR was performed with GoTaq Flexi DNA Polymerase (Promega, Madison, Wis.), 2 mmol $l^{-1}$ $MgCl_2$, 10 mmol $l^{-1}$ forward and reverse primers, and 10 mmol $l^{-1}$ dNTP's. PCR amplicons were separated by gel electrophoresis on a 2% agarose gel and bands were visualized with UV light.

Effect of AAA and EAA on Planktonic Growth and Biofilm Amounts:

AAA was supplemented as lithium salt (TCI America, Portland Oreg.) at concentrations between 0 and 40 mg $ml^{-1}$ in TSB. EAA (Alfa Aesar, Ward Hill Mass.) supplemented growth media were prepared at concentrations between 0 and 20 mg $ml^{-1}$ in TSB.

AAA or EAA solutions at the indicated concentrations were produced in individual wells of a 24-well polystyrene plate in 4 (EAA experiment; 2 biological replicates at 2 technical replications) or 6 replicates (AAA experiment; 3 biological replicates at 2 technical replications) per bacterial strain and growth temperature. The bacterial growth media were inoculated with bacteria, using the PBS cultures in a 1:100 dilution. The 24-well plates were sealed with sterile film and incubated statically in a Synergy H1 Hybrid Reader (Biotek Instruments, Inc., Winooski, Vt.). Growth temperatures were 37° C. for *C. sakazakii*, 30° C. for *S. marcescens* which does not grow at 37° C., and 25 as well as 37° C. for *Y. enterocolitica* because of the multiple published genotypic and phenotypic differences at these two temperatures that are relevant for the qPCR experiment.

To determine bacterial growth, an $OD_{600}$ reading was taken every 2 h for the duration of the incubation, which was 16 h for the 37° C. experiments and 24 h for the lower temperatures. Growth data were expressed as maximal velocity in mOD/min and calculated as averages with standard deviations across the replicates. The $IC_{50}$ values were calculated using Masterplex software (Hitachi Solutions, San Bruno, Calif.). Masterplex's best fit feature was used for the calculations, which selects the best equation and algorithm for the data (4-parameter or 5-parameter). In addition to the $IC_{50}$ values, the software also calculated a corresponding $R^2$ value to evaluate the goodness of fit for the calculated curve.

To quantify biofilm, plates were removed from the plate reader at the end of the incubation period. Biofilm was determined with the CV assay to determine biomass and the ATP assay to determine the energy load of the bacteria. For the effect of EAA on *Y. enterocolitica*, the number of viable bacteria within the biofilm was determined. For all three assays, the planktonic bacteria were removed from the wells with a pipette and biofilms were rinsed three times with 1 ml of PBS. To remove excess liquid between rinses, plates were inverted and tapped on absorbent paper.

For the CV assay, washed plates were allowed to dry for 1 h at room temperature. 1 ml of 0.1% CV was added to each well and allowed to incubate at room temperature for 15 minutes. The CV was pipetted off and the wells were rinsed three times with PBS, again with inverted tapping between each rinse to remove excess liquid. The plates were allowed to dry for 1 h at room temperature. CV was resolubilized using 0.5 ml of an 80% ethanol/20% acetone mixture. 150 µl from each of the 24 wells was pipetted onto a 96-well polystyrene plate and the $OD_{600}$ was read with the Synergy plate reader. Data were expressed as $OD_{600}$. Averages, standard deviations, and $IC_{50}$ values were calculated as described for planktonic growth.

For the ATP assay, biofilms were re-suspended with 1 ml of $ddH_2O$ and 100 µl from each well were transferred to a white 96-well polystyrene plate. 100 µl of BacTiter-Glo™ (a thermostable luciferase and buffer formulation for supporting bacterial cell lysis and generation of a luminescent signal; Promega, Madison, Wis.)) was added to each well and the plate reader was used to determine relative luminosity (RLU). Averages, standard deviations, and $IC_{50}$ values were calculated as described for planktonic growth.

Analysis of Gene Expression in Response to AAA:

The expression of *Y. enterocolitica* 8081v flhD, inv, yadA, yomA, virF, and yopQ in response to AAA was determined by qPCR. Bacteria were grown in TSB at 25 or 37° C. for 24 h in the absence or presence of 5 mg ml$^{-1}$ AAA. Planktonic bacteria and biofilm bound bacteria were harvested, stop solution (5% PheOH in EtOH) was added, bacteria were pelleted by centrifugation, and stored at −80° C. To extract RNA, samples were defrosted on ice and suspended in 480 µl hot lysis buffer (2% SDS, 200 mmol l$^{-1}$ NaOAc, 20 mmol l$^{-1}$ EDTA). RNA was isolated with the hot phenol-sodium dodecyl sulfate method as described, using one phenol and three phenol:chloroform extractions with increasing ratios of chloroform. RNA was precipitated by isoproponal centrifugation at 10,000 g, and 4° C. for 90 min, washed in 70% ethanol, and cleaned up as described.

RNA was reverse transcribed with random hexamer primers and Superscript® II Reverse Transcriptase (Invitrogen™), following the protocol of the manufacturer. The solution was neutralized with 1 mol l$^{-1}$ Tris, pH 7.4. Cleanup and sample concentration was done with 30 kDa EMD Millipore Amicon™ Ultra-0.5 centrifugal filter units (Fisher Scientific). The resultant cDNA was stored at −20° C. The qPCR was performed using the iCycler iQ5 Real Time PCR Detection System (BioRad, Hercules, Calif.) and iQ™ SYBR Green Supermix (BioRad) for detection. The reaction mixture contained 1×iQ™ SYBR Green Supermix, 2 ng l$^{-1}$ of cDNA, and 0.05 um of each primer (TABLE 1). The reaction was performed with 50 cycles of 30 s at 94° C., 30 s at 55° C., and 1 min at 72° C. Melting curves were obtained after each reaction and generally yielded single peaks. A total of nine replicates were performed for each condition (three biological replicates from independently grown cultures and three technical replicates).

TABLE 1

Forward and reverse *Y. enterocolitica* primers for qPCR.

| Gene | Forward primer | Reverse primer |
|------|----------------|----------------|
| invF | 5'-CATCATCTGGTGCAT CAAGG-3' | 5'-TTACACAGCATCAC GTTAGC-3' |
| fleB | 5'-CGCAGCAGAGACAAT ACAGTT-3' | 5'-TGAACAATACCGTG AACAACCT-3' |
| ymoA | 5'-ACGAACTTTCTGACG ATGAGCTGGA-3' | 5'-TGTGAGTTCAGCTA AGCGGTGGTCT-3' |
| yopQ | 5'-AGTTGGTGTCAATGT CGCTG-3' | 5'-ACTGCGCTACTGCT CATTTAC-3' |
| yadA | 5'-GCCGAATCTCCCAAT GCCTTAC-3' | 5'-CGGTTGGTGCTAGT GCTGAAG-3' |
| flhD | 5'-CGTCTTTTAACGATA GCTCGTG-3' | 5'-AACGATGAGAAAGC CTCAGC-3' |
| virF | 5'-CTACAAGGGTGGAAA CTAAGC-3' | 5'-ATTGGTGAGCATAG AGAATACG-3' |
| cysG | 5'-GATCGCGGCGAAGTA GTATTAG-3' | 5'-GCTTGCTGAATCTG CTGTAAAC-3' |

The qPCR data were normalized by means of housekeeping genes, using the cysG gene that was used as a reference gene to quantify differences in *E. coli* mRNA transcripts. qPCR with the cysG gene was performed as described for the test genes. Differences in threshold cycles (Tc) between two samples were subtracted from the difference in threshold cycles for the respective test gene in the same two samples and expression ratios were determined as $2^{-\Delta\Delta Tc}$. Differences in cysG transcript between any two samples were never higher than 0.9 threshold cycles.

Motility Assay:

Motility plates consisting of 1% tryptone, 0.5% NaCl, and 0.3% agar were used to determine the motility of *Y. enterocolitica* at 25° C. and 37° C., both with and without 10 mg ml$^{-1}$ of AAA. Bacteria were picked from agar plate and inoculated into the center of a motility plate. Plates were incubated in a humid environment and the diameter of the ring was followed for 10 h. Data were expressed as mm h$^{-1}$ and average and standard deviations were calculated across 6 replicates.

Results and Discussion

AAA Reduced Planktonic Growth and Biofilm Amounts of Three Pathogens:

In order to determine the effect of AAA on planktonic growth and biofilm amounts of different pathogens, growth and biofilm assays were performed on *C. sakazakii* at 37° C., *S. marcescens* at 30° C., and *Y. enterocolitica* at 25° C. and 37° C. AAA reduced planktonic growth, as well as biofilm amounts determined with both assays for all three bacterial pathogens at all growth temperatures tested (FIGS. 1A-H). As shown in TABLE 2, $IC_{50}$ values for *C. sakazakii* ranged from 20 to 24 mg ml$^{-1}$, $IC_{50}$ values for *S. marcescens* were even larger at 24 to 35 mg ml$^{-1}$, while the lowest $IC_{50}$ values were obtained for *Y. enterocolitica* at 37° C., ranging from 11 to 14 mg ml$^{-1}$. Altogether, these tests show that AAA appears to have an inhibitory effect on growth and biofilm of these three pathogens.

TABLE 2

Inhibitory concentration for AAA that reduces growth and biofilm to 50%.

| Organism | Temperature | Assay | IC$_{50}$ | R$^2$ |
|---|---|---|---|---|
| C. sakazakii | 37° C. | Planktonic growth | 20 mg/ml | 0.963 |
|  |  | Biofilm (CV) | 22 mg/ml | 0.957 |
|  |  | Biofilm (ATP) | 24 mg/ml | 0.761 |
| S. marcescens | 30° C. | Planktonic growth | 29 mg/ml | 0.948 |
|  |  | Biofilm (CV) | 35 mg/ml | 0.7337 |
|  |  | Biofilm (ATP) | 24 mg/ml | 0.987 |
| Y. enterocolitica | 25° C. | Planktonic growth | NA | NA |
|  |  | Biofilm (CV) | 26 mg/ml | 0.9534 |
|  |  | Biofilm (ATP) | 18 mg/ml | 0.9534 |
| Y. enterocolitica | 37° C. | Planktonic growth | 11 mg/ml | 0.645 |
|  |  | Biofilm (CV) | 14 mg/ml | 0.779 |
|  |  | Biofilm (ATP) | 12 mg/ml | 0.8332 |

Figure 1B:
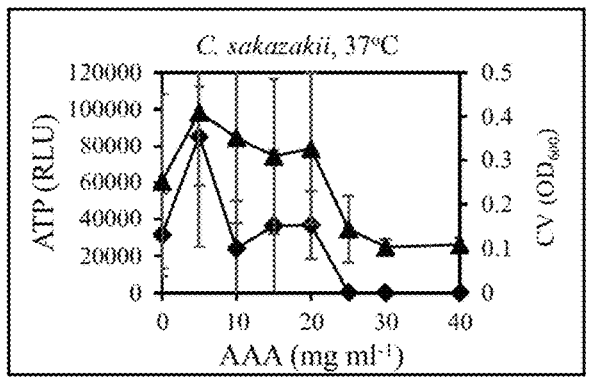
Figure 1C:
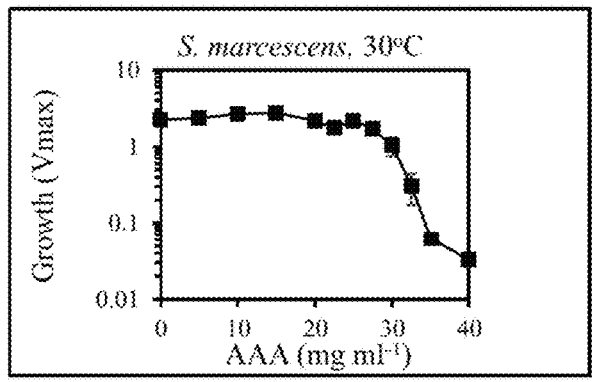
Figure 1D:
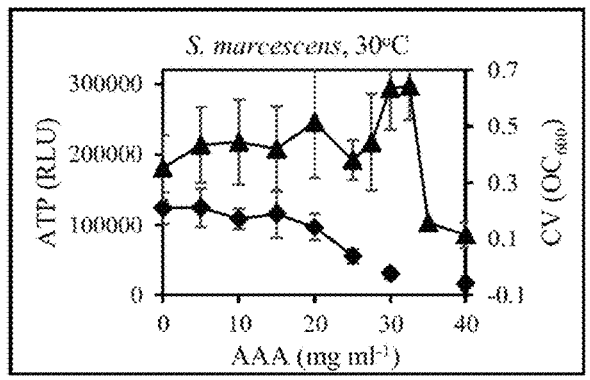

More specifically, with respect to *C. sakazakii*, planktonic growth decreased with increasing concentrations of AAA with an IC$_{50}$ of 20 mg/ml (FIG. 1A). At concentrations higher than 22 mg ml$^{-1}$, *C. sakazakii* exhibited a negative growth rate after background subtraction. These data points are omitted because the growth data were plotted on a logarithmic scale (FIG. 1A). The IC$_{50}$ value for *C. sakazakii* biofilm was 22 mg/ml as determined with the CV assay (FIG. 1B, triangles) and 24 mg/ml as determined with the ATP assay (FIG. 1B, diamonds). Turning to *S. marcescens*, planktonic growth decreased drastically around 35 mg/ml with an IC$_{50}$ of 29 mg/ml (FIG. 1C). The quantification of the biofilm biomass with the CV assay (FIG. 1D, triangles) also exhibited a sizeable decrease at 35 mg/ml of AAA, after an increase in biofilm amounts around 30 mg/ml. The IC$_{50}$ value for *S. marcescens* biofilm amounts was 35 mg/ml as determined with the CV assay (FIG. 1D, triangles) and 24 mg/ml as determined with the ATP assay (FIG. 1D, diamonds).

Figure 1E:
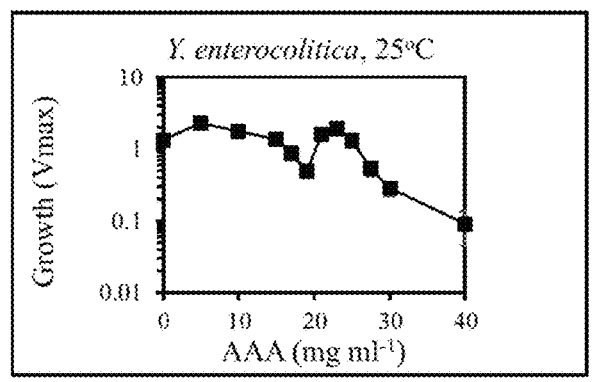
Figure 1F:
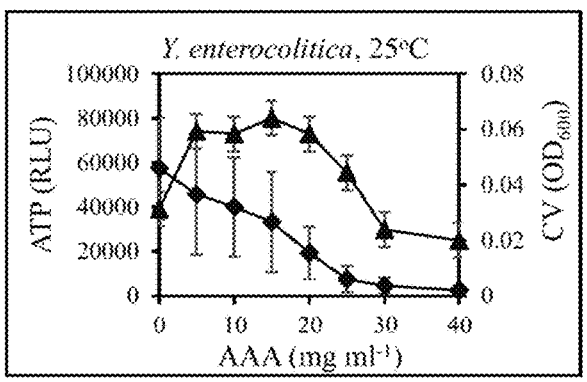

As for *Y. enterocolitica*, at 25° C. planktonic growth increased slightly towards 5 mg/ml, then decreased towards 20 mg/ml before showing another increase in growth towards 25 mg/ml followed by a final steady decrease (FIG. 1E). The IC$_{50}$ value for growth could not be calculated. The IC$_{50}$ value for biofilm was 26 mg/ml as determined with the CV assay (FIG. 1F, triangles) and 18 mg/ml as determined with the ATP assay (FIG. 1F, diamonds). At 37° C., *Y. enterocolitica* growth (FIG. 1G) and biofilm (FIG. 1H) showed an increase towards 5 mg/ml (10 mg/ml for the CV assay) before exhibiting a pronounced decrease. The IC$_{50}$ value for growth was 11 mg/ml and the IC$_{50}$ values for biofilm were 14 mg/ml as determined with the CV assay (FIG. 1H, triangles) and 12 mg/ml as determined with the ATP assay (FIG. 1H, diamonds).

The increase in growth or biofilm amounts at a low to moderate concentration of AAA and decrease at the highest AAA concentrations was an intriguing phenomenon observed in some of the experiments (e.g., the crystal violet (CV) assays for *S. marcescens* (FIG. 1D, triangles), planktonic growth of *Y. enterocolitica* at 25° C. (FIG. 1E), and biofilm amounts determined by CV and ATP assays for *Y. enterocolitica* grown at 37° C. (FIG. 1H)). Although the reason for this phenomenon is unclear, AAA was identified as an inhibitor of *E. coli* growth and biofilm in a nutrient screen. It is possible that the bacteria metabolize AAA as a carbon source at non-toxic concentrations. In *E. coli*, it has been known for a long time that growth is inhibited by ketone bodies. However, AAA can also be degraded by the combined action of an acetate CoA-transferase and a thiolase which are encoded by the atoDAB operon under the control of the AtoS/AtoC two-component system. Intriguingly, AtoSC is also an activator of motility and chemotaxis in *E. coli* through transcription regulation of flhD. While little seems to be known about AAA metabolism in *C. sakazakii* (which did not show the up-tick), *S. marcescens* and several species of the *Yersiniae* possess atoD and atoA (www.uniprot.org).

AAA Reduced mRNA Transcripts of *Y. enterocolitica* flhD, Inv, and yadA:

To determine the effect of AAA on gene expression in *Y. enterocolitica*, quantitative PCR (qPCR) was performed. A low concentration of 5 mg/ml AAA was used because this concentration had not exerted an inhibitory effect on biofilm or planktonic growth in the previous experiment. Genes were selected as follows: FlhD/FlhC is the flagellar master regulator and a global regulator that affects many metabolic genes, plasmid encoded virulence genes that are involved in the late stages of infection, and biofilm. The five virulence genes cover early and late stages of infection and include chromosomally and plasmid encoded genes.

Figure 2A:
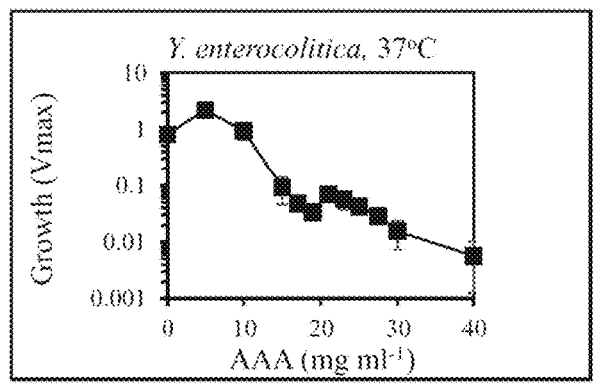
FIGS. 2A-F show graphs illustrating mRNA transcript for (A) flhD, (B) inv, (C) virF, (D) yopQ, (E) ymoA, and (F) yadA in the absence or presence of 5 mg/ml of AAA. Four comparisons were calculated: B025/B525, mRNA transcript was compared between biofilm associated bacteria (B) grown in the absence (0) or presence (5) of AAA at 25° C. (25); P025/P525, mRNA transcript was compared between planktonic bacteria (P) grown in the absence (0) or presence (5) of AAA at 25° C. (25); B037/B537, mRNA transcript was compared between biofilm associated bacteria (B) grown in the absence (0) or presence (5) of AAA at 37° C. (37); P037/P537, mRNA transcript was compared between planktonic bacteria (B) grown in the absence (0) or presence (5) of AAA at 37° C. (37). Averages were calculated across nine replicates for each comparison, the errors bars indicate one standard deviation.
Figure 2A:
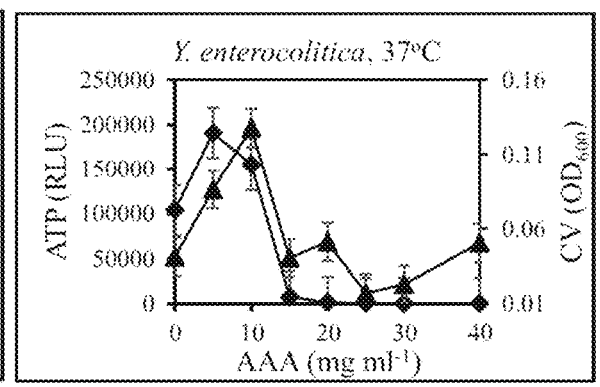
Figure 2A:
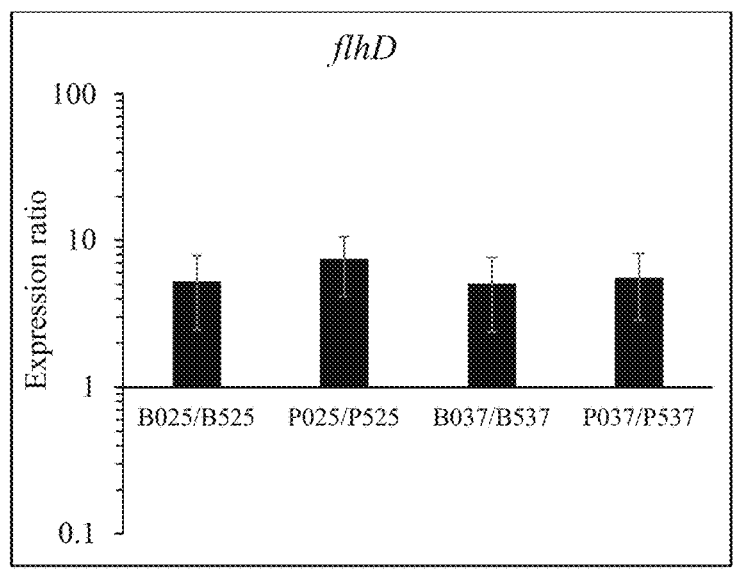
Figure 2B:
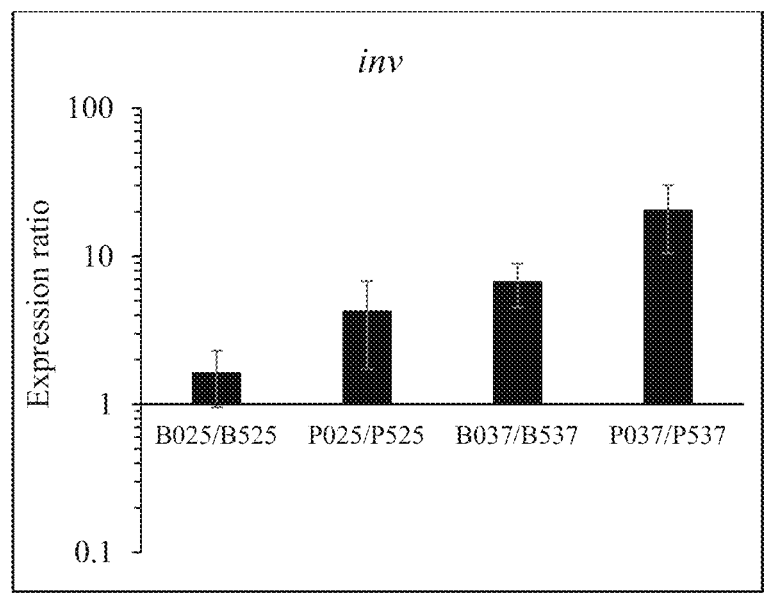
Figure 2C:
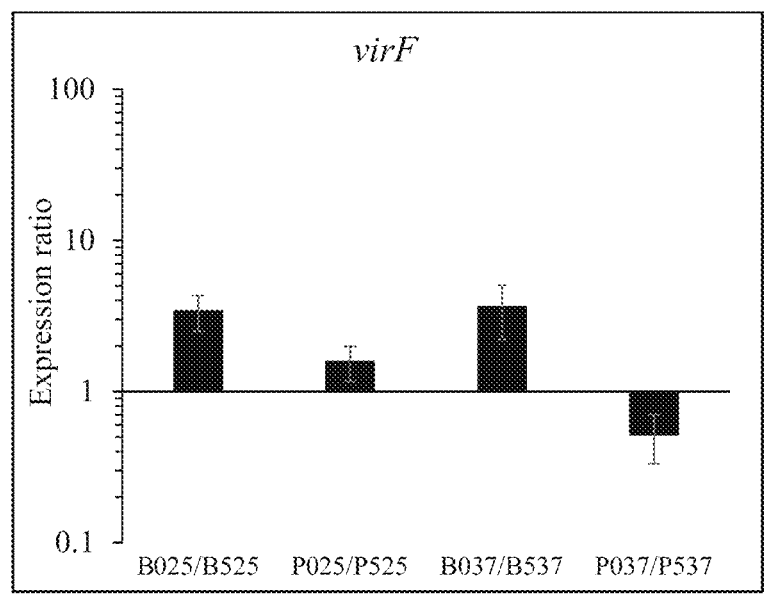
Figure 2D:
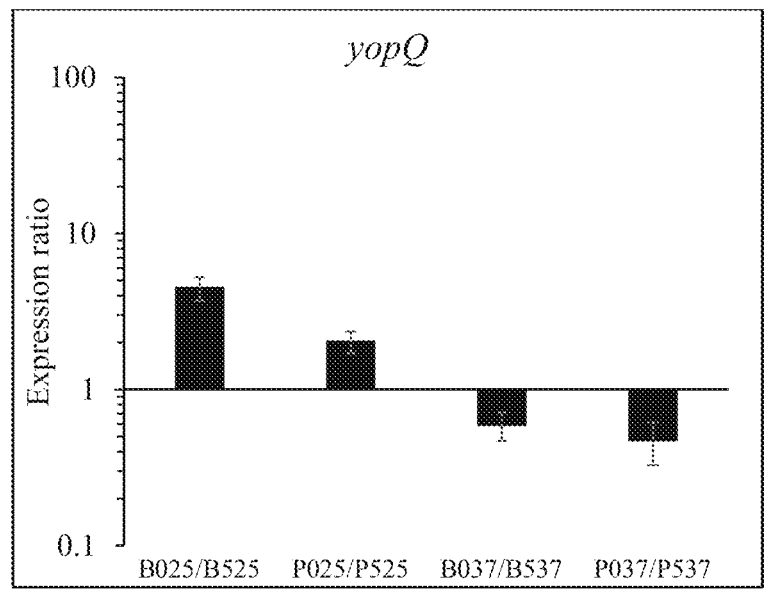
Figure 2E:
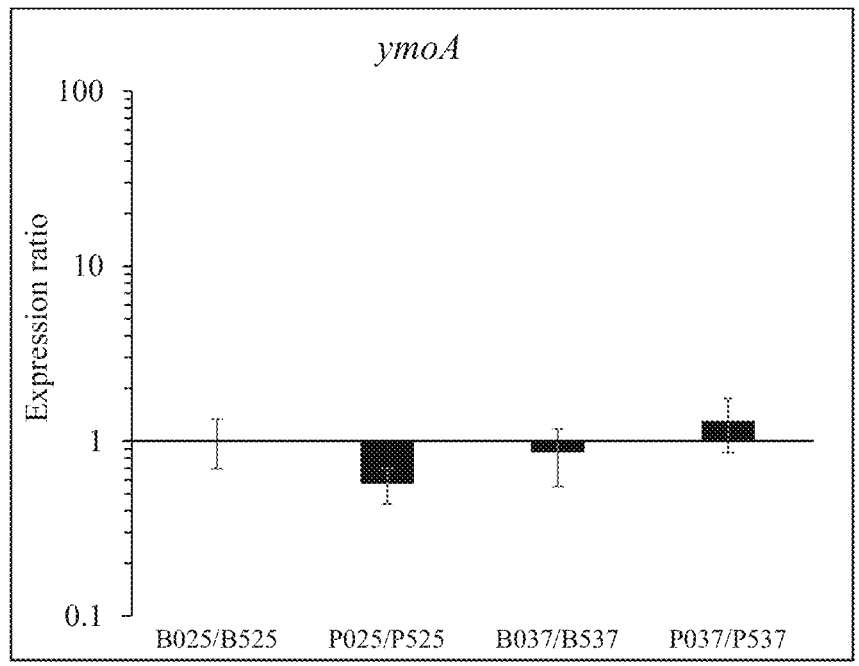
Figure 2F:
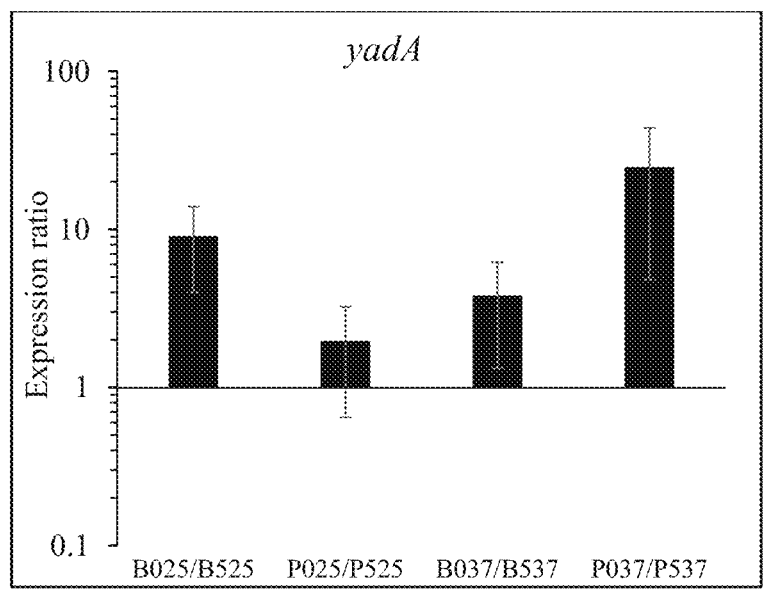

The primary outcome of this experiment is that AAA did indeed impact transcription of some of the tested genes (FIGS. 2A-F). In particular, mRNA levels of flhD were reduced approximately 5 fold by AAA in all four comparisons (FIG. 2A). The effect of gene transcription on phenotype was confirmed by motility assays. A concentration of 5 mg/ml of AAA was able to reduce motility of *Y. enterocolitica* from approximately 3.6 mm/h on semi solid tryptone broth agar plates to about 0.25 mm/h. This was done at 25° C. At 37° C., motility in the absence of AAA was already low. Motility is the first phase of biofilm formation in many bacteria. In *Y. enterocolitica*, motility is often co-regulated with biofilm, so the inhibiting effect of AAA on motility might contribute to the effect on biofilm amounts.

Figure 3:
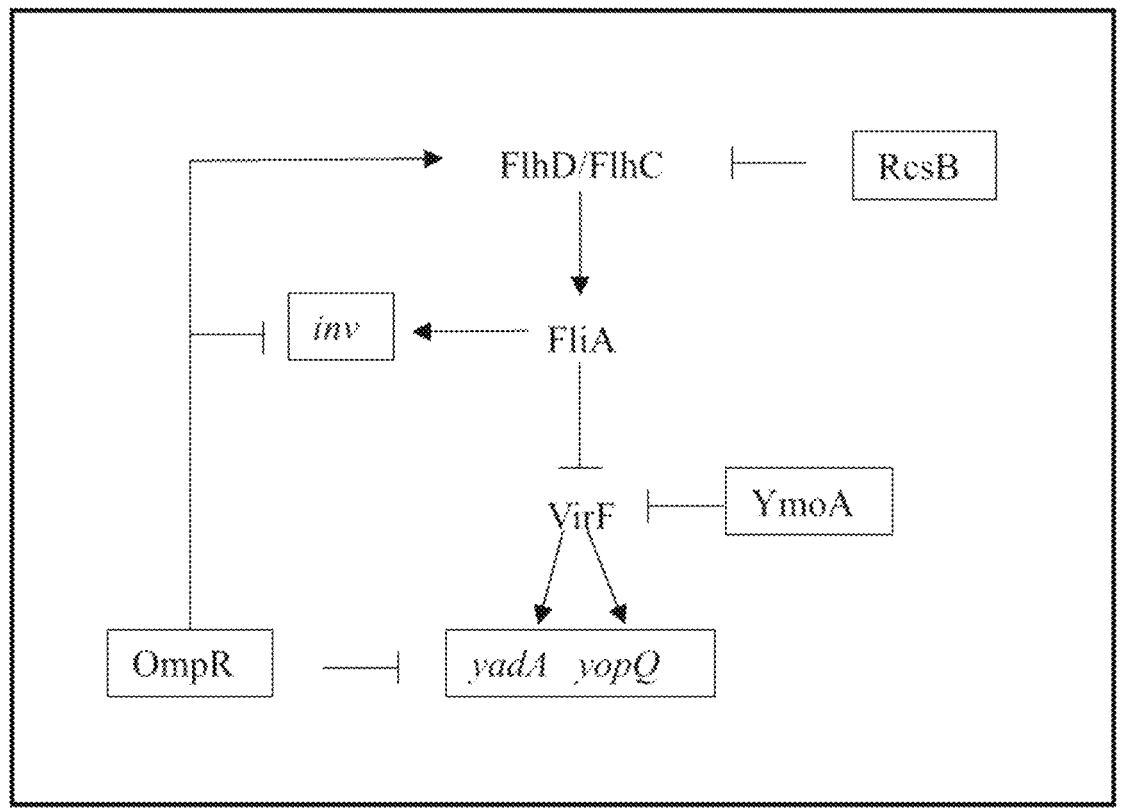
FIG. 3 shows a schematic of known regulatory relationships between *Y. enterocolitica* virulence genes.
Figure 4A:
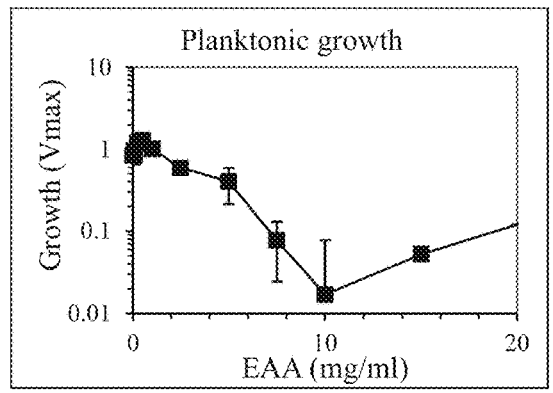
FIGS. 4A-F show graphs illustrating the effect of EAA on *Y. enterocolitica*. (A) planktonic growth, (B) biofilm amounts, and (C) bacterial cell counts of *Y. enterocolitica* at 25° C. (D) planktonic growth, (E) biofilm amounts, and (F) bacterial cell counts of *Y. enterocolitica* at 37° C. Squares represent planktonic growth, expressed as maximal velocity of $OD_{600}$. Triangles are used for the biofilm amounts determined by CV and expressed as $OD_{600}$ at the end of the incubation period. Diamonds represent biofilm amounts determined by the ATP assay and expressed as RLU. Cell counts are documented as black bars. Averages were calculated over four replicates for each experiment. Errors indicate one standard deviation.
Figure 4B:
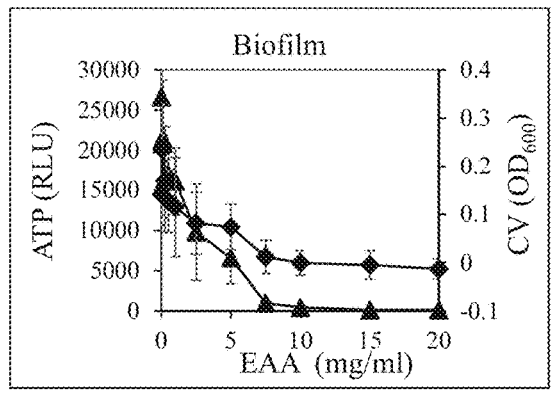
Figure 4C:
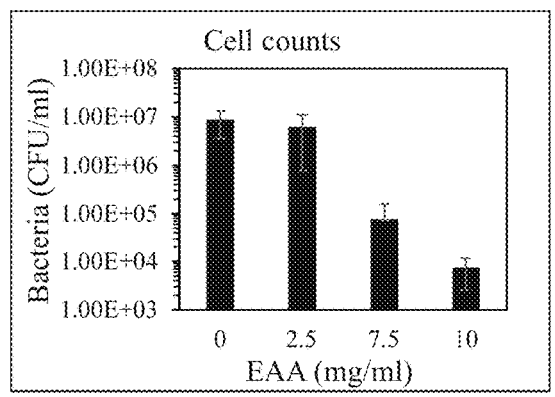
Figure 4D:
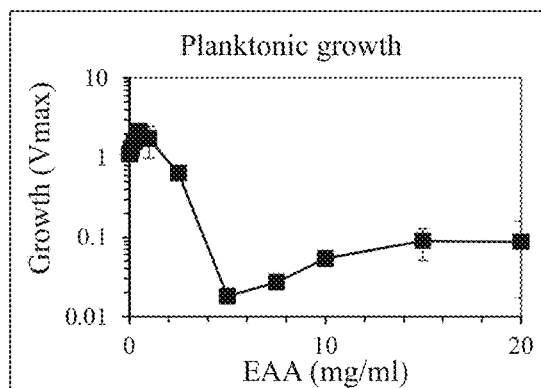
Figure 4E:
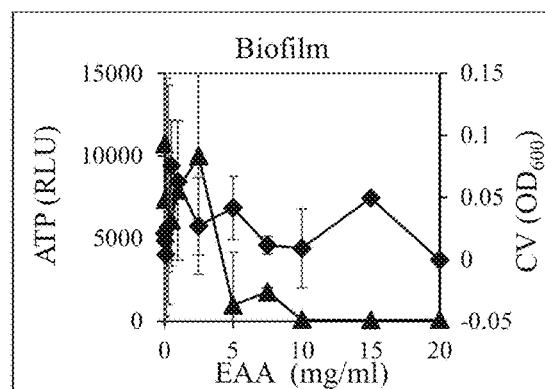
Figure 4F:
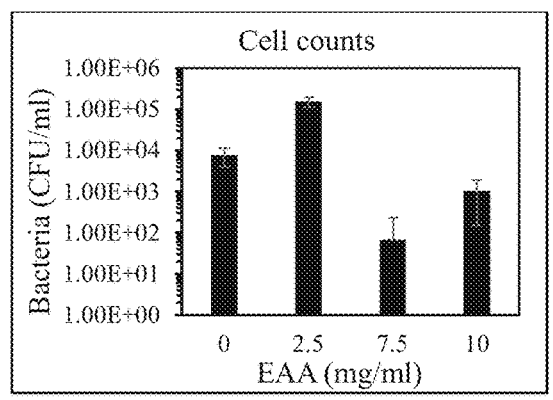
Figure 5A:
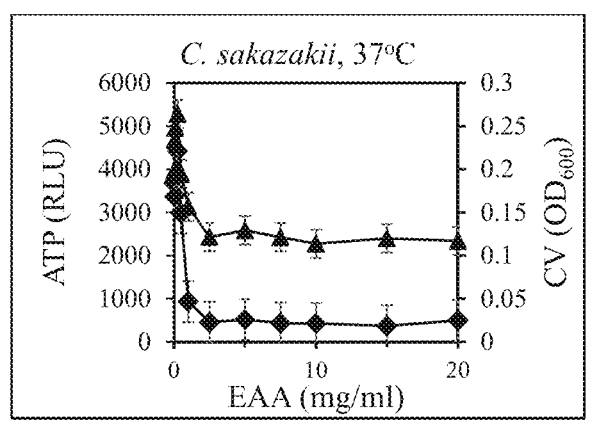
FIGS. 5A-B show graphs illustrating the effect of EAA on biofilm amounts (A) *C. sakazakii* at 37° C. and (B) *S. marcescens* at 30° C. Triangles are used for the biofilm amounts determined by CV and expressed as $OD_{600}$ at the end of the incubation period. Diamonds represent biofilm amounts determined by the ATP assay and expressed as RLU. Averages were calculated over four replicates for each experiment. Errors indicate one standard deviation.
Figure 5B:
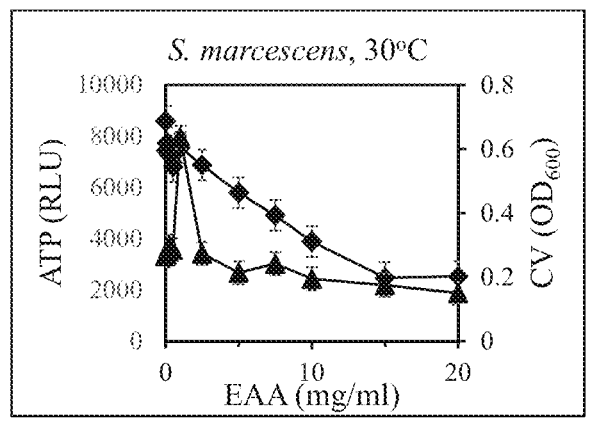

As the next outcome, AAA did not increase transcription in any of the tested genes (FIGS. 2A-F). This is important because it is not desirable to reduce planktonic growth and/or biofilm amounts at the expense of an increase in virulence gene transcription. mRNA levels of flhD (FIG. 2A) were reduced approximately 5 fold in biofilm associated and planktonic bacteria at both growth temperatures of 25 and 37° C. mRNA levels of the inv gene (FIG. 2B) that is positively regulated by FlhD/FlhC and also expressed higher at 25° C. than at 37° C. showed a similar pattern of reduction, except the inhibitory effect was stronger at 37° C. than at 25° C. The inv gene also showed a larger reduction in mRNA transcript in planktonic bacteria than in biofilm. A slight reduction in mRNA levels of inv was seen at 25° C. in biofilm bound bacteria. mRNA levels of virF (FIG. 2C), which encodes the activator of plasmid encoded yop genes and the chromosomally encoded yadA gene, showed very little reduction by AAA. At best, virF transcript in biofilm was reduced by about 3 fold at both temperatures. In agreement with this, mRNA levels of yopQ (FIG. 2D) looked very similar to that of virF, with the exception of biofilm bound bacteria at 37° C. which did not show the AAA reduction. Absolutely no effect of AAA was seen for ymoA (FIG. 2E), which encodes a negative regulator of virF. mRNA levels for yadA (FIG. 2F) were reduced by AAA almost 10 fold in biofilm bound bacteria at 25° C. and approximately 20 fold in planktonic bacteria at 37° C. Correlation between the qPCR profiles of the tested genes and known transcriptional regulatory relationships is illustrated in FIG. 3.

Altogether, previously published regulation between the investigated genes can explain similarities in qPCR profiles for some, but not all of the genes and/or comparisons.

Without wishing to be bound by theory, it is believed that the moderate similarity in the flhD and inv profiles may be due to the positive regulatory effect of FlhD/FlhC on inv transcription. Likewise, the similarity in the virF and yopQ profiles may be due to the activating effect of VirF on yopQ transcription. However, yadA is activated by virF as well and shows a completely different pattern of reduction by AAA. Most likely, AAA impacts transcription of genes through multiple dependent and independent pathways.

The Reduction in Planktonic Growth and Biofilm Amounts of *Y. enterocolitica* is More Pronounced for EAA:

Since AAA is expensive and also only effective at inhibiting planktonic growth and biofilm at rather high concentrations, more cost efficient homologs of AAA were investigated to determine if they would exert their inhibitory effect at lower concentrations. EAA is the ethyl ester of AAA and used as flavoring ingredient for food (Flavis No 9.402). According to the MSDS by Science Lab, the $LD_{50}$ for the toxicity in rats after oral application is 3.98 g/kg of body weight.

The effect of EAA on planktonic growth and biofilm amounts of the three pathogens was determined. For *Y. enterocolitica* (FIGS. 4A-F; TABLES 3-4), bacteria were grown at 25 and 37° C., and planktonic growth, biofilm biomass by CV and ATP assays, and bacterial cell counts within the biofilm were determined. At 25° C., planktonic growth of *Y. enterocolitica* (FIG. 4A; TABLE 3) decreased between 0 and 10 mg/ml and increased slightly towards higher concentrations of EAA. The log reduction at 10 mg/ml was 1.7 log, which is the equivalent to 50 fold. Biofilm amounts quantified by both ATP and CV assays (FIG. 4B) decreased between 0 and 7.5 mg/ml of EAA. Biofilm by the ATP assay was reduced with a 2.3 log ratio (200 fold) at 15 mg/ml of EAA. For the CV assay, biofilm biomass even reached negative values, which may be due to background subtraction. Bacterial cell counts in the biofilm (FIG. 4C) were reduced by 2.06 logs at 7.5 mg/ml and 3.07 logs at 10 mg/ml. $IC_{50}$ values for the inhibitory effect of EAA were 3.2 mg/ml for planktonic growth, 2.1 mg/ml for the ATP content of the biofilm, 1 mg/ml for biofilm biomass determined with the CV assay, and 3 mg/ml for live bacteria. Since log reductions as well as $IC_{50}$ values were similar throughout the four phenotypes (growth, biofilm by CV, biofilm by ATP, bacteria in the biofilm), it was concluded that EAA acts upon the 25° C. biofilm primarily by reducing the number of bacteria in the biofilm.

TABLE 3

Inhibitory concentration for EAA that reduces growth and biofilm of *Y. enterocolitica* to 50% at 25° C.

| Organism | Temperature | Assay | $IC_{50}$ | $R^2$ |
|---|---|---|---|---|
| *Y. enterocolitica* | 25° C. | Planktonic growth | 3.2 mg/ml | 0.777 |
| | | Biofilm (ATP) | 2.1 mg/ml | 0.865 |
| | | Biofilm (CV) | 1 mg/ml | 0.584 |
| | | Live cells | 3 mg/ml | 0.495 |

At 37° C., planktonic growth of *Y. enterocolitica* (FIG. 4D; TABLE 4) decreased between 0 and 5 mg/ml and increased slightly towards higher concentrations of EAA. At 5 mg/ml, the log reduction was 1.78, which is the equivalent of 61 fold. Biofilm amounts quantified by the ATP and CV assays (FIG. 4E) decreased between 0 and 10 mg/ml of EAA and were abolished at 10 mg/ml. Bacterial cell counts in the biofilm (FIG. 4F) did not show a reduction at 2.5 mg/ml. However, at 7.5 mg/ml, a log reduction of 2.06 logs was observed, yet, cell counts increased again when the EAA concentration was increased to 10 mg/ml. Biofilm amounts determined by all three assays were reduced at 37° C., relative to 25° C.

TABLE 4

Inhibitory concentration for EAA that reduces growth and biofilm of *Y. enterocolitica* to 50% at 37° C.

| Organism | Temperature | Assay | $IC_{50}$ | $R^2$ |
|---|---|---|---|---|
| *Y. enterocolitica* | 37° C. | Planktonic growth | 2.48 mg/ml | 0.771 |
| | | Biofilm (ATP) | 4.29 mg/ml | 0.706 |
| | | Biofilm (CV) | NA | NA |
| | | Live cells | NA | NA |

Interestingly, the log reduction in biofilm amount as determined with the ATP assay was 2.04 (110 fold) at 10 mg/ml of EAA, while the log reduction in live bacteria within the biofilm was only 0.92 (8.3 fold). It is possible that EAA acts upon the 37° C. biofilm by reducing the energy content of the bacteria within the biofilm more so than the number of recoverable bacteria.

For *C. sakazakii* (FIG. 5A; TABLE 5), EAA was more effective than AAA at reducing biofilm amounts as well, with $IC_{50}$ values of 0.31 mg/ml and 0.7 mg/ml for the ATP and CV assays, respectively. For *S. marcescens* (FIG. 5B; TABLE 6), the EAA effect was less pronounced than for *Y. enterocolitica* and *C. sakazakii* with $IC_{50}$ values of 5.5 mg/ml for the ATP assay and 5.6 mg/ml for the CV assay.

TABLE 5

Inhibitory concentration for EAA that reduces biofilm of *C. sakazakii* to 50% at 37° C.

| Organism | Temperature | Assay | $IC_{50}$ | $R^2$ |
|---|---|---|---|---|
| *C. sakazakii* | 37° C. | Biofilm (ATP) | 0.31 mg/ml | 0.973 |
| | | Biofilm (CV) | 0.7 mg/ml | 0.900 |

TABLE 6

Inhibitory concentration for EAA that reduces biofilm of *S. marcescens* to 50% at 30° C.

| Organism | Temperature | Assay | $IC_{50}$ | $R^2$ |
|---|---|---|---|---|
| *S. marcescens* | 30° C. | Biofilm (ATP) | 5.5 mg/ml | 0.980 |
| | | Biofilm (CV) | 5.6 mg/ml | 0.793 |

In summary, AAA at a concentration of 5 mg $ml^{-1}$ reduced *Y. enterocolitica* mRNA transcripts of the flagellar master regulator operon flhD, the invasion gene inv, and the adhesion gene yadA. Transcription of the regulator of plasmid encoded virulence genes virF, the plasmid encoded virulence gene yopQ, and ymoA were largely unaffected by AAA. Importantly, AAA did not cause an increase in transcription of any of the tested virulence genes. As a more cost efficient homolog of AAA, the effect of ethyl acetoacetate (EAA) was tested. EAA reduced growth, biofilm amounts, and live bacterial cell counts up to 3 logs. $IC_{50}$ values ranged from 0.31 mg $ml^{-1}$ to 5.6 mg $ml^{-1}$. Accordingly, in conclusion, i) AAA was confirmed as a weak biofilm inhibitor, ii) it was determined that AAA did not increase mRNA levels of six major virulence genes, and iii) EAA was demonstrated as a novel biofilm inhibitor that is more effective than AAA. Using two different assays to quantify biofilm amounts, it was determined that EAA was able to reduce biofilm amounts of three bacterial pathogens with a maximal log reduction of 3 logs and $IC_{50}$ values around 1 mg/ml.

Example 2

Overall, chemicals serving as anti-microbials in food are being applied routinely throughout the food production chain. However, despite all efforts to prevent bacteria in beef meat, outbreaks of *E. coli* O157:H7 and other shiga toxin producing *E. coli* due to the consumption of beef meat still happen across the world and in the U.S. Accordingly, there remains a continued need for the development of novel and innovative microbial inhibitors.

This Example is directed to determining the effect of ethyl acetoacetate (EAA) on spoilage and pathogenic bacteria on ground beef. Meat harbors two different types of microbiota; spoilage organisms that effect the sensory attributes of the meat and pathogens that cause consumer illness. The bacteria that contribute to spoilage during aerobic cold storage are predominantly *pseudomonads*, while the bacterial counts of *Brocothrix thermospacta* and Enterobacteriaceae are typically lower. *Lactobacilli* are present, but not always considered spoilage bacteria. Under some circumstances, *lactobacilli* are capable of reducing the number of spoilage and pathogenic bacteria.

The Food Safety and Inspection Service (FSIS) from the United States Department of Agriculture (USDA) recommends a storage temperature of 4.4° C. for ground beef, to be consumed within 2 days (www.fsis.usda.gov). This is because bacterial growth is considerably higher at 10° C. than at 5° C. In fact, a designation of 'abusive temperature' has been established, which refers to the storage of ground beef at 10° C. This Example determines the reduction of spoilage and pathogenic bacteria on ground beef stored at abusive temperature by the addition of ethyl acetoacetate (EAA).

EAA is the ethyl ester of acetoacetate, approved as a food additive by the FDA under 21CFR172.515, and used as flavoring ingredient (Flavis No 9.402). According to the MSDS by Science Lab, the $LD_{50}$ for the toxicity in rats after oral application is 3.98 g/kg of body weight (sciencelab.com). As shown in Example 1 above, EAA reduced growth, biofilm amounts, and live bacterial cell counts of three bacterial pathogens up to 3 logs. The inhibitory concentration that was needed to achieve a 50% reduction ($IC_{50}$) ranged from 0.31 mg ml- to 5.6 mg ml$^{-1}$. This Example describes an application for EAA that is relevant in food processing. More specifically, the use of EAA is proposed to reduce the live bacterial counts on ground beef for several common food spoilage bacteria and *E. coli* and as an example of a pathogenic bacteria.

Materials and Methods

Meat Processing

Figure 6:
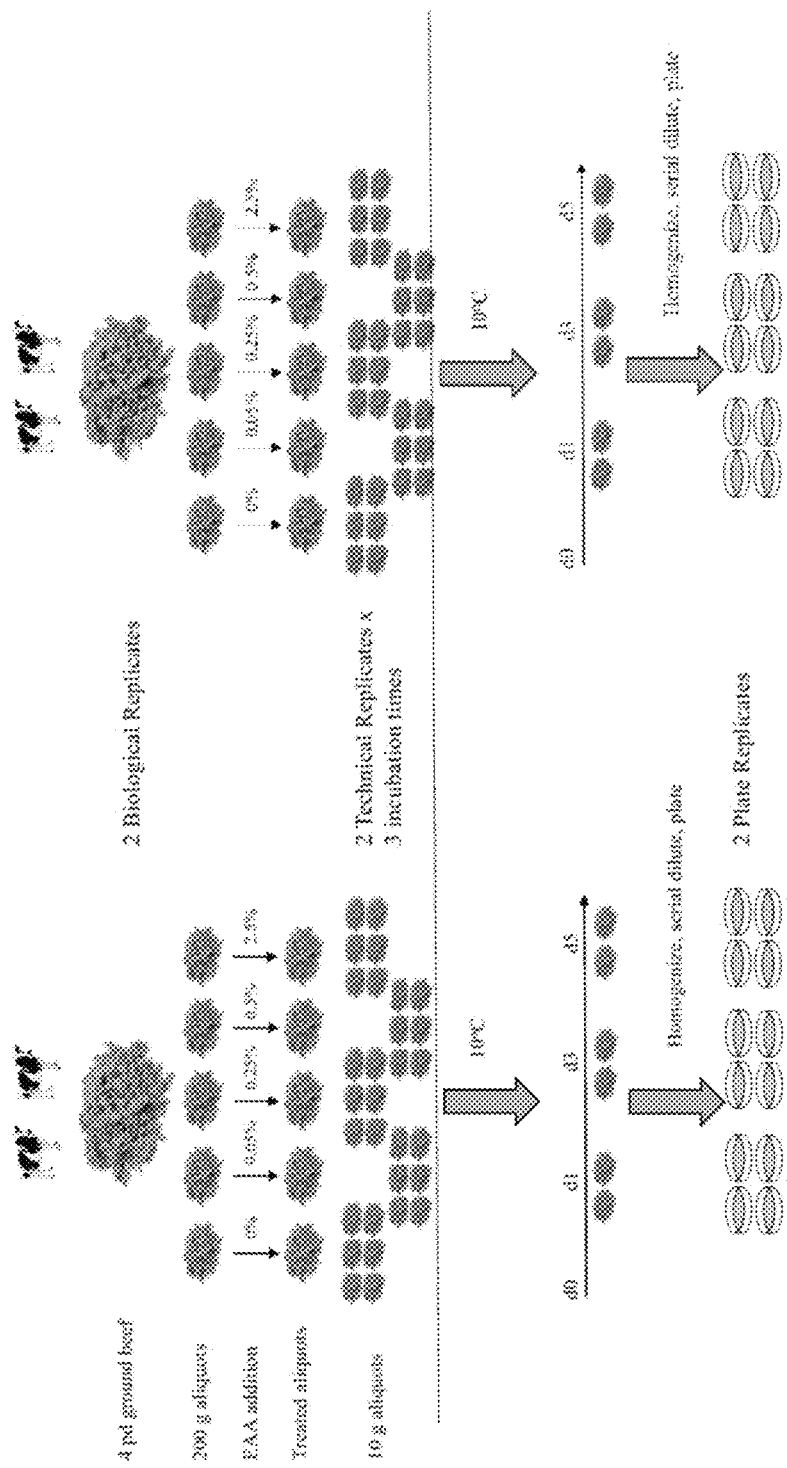
FIG. 6 shows a schematic illustrating workflow for the meat processing and enumeration of the bacteria. The top half of the figure demonstrates the meat processing and the production of the biological and technical replicates. The bottom half explains the 10° C. incubation, sampling of the meat pieces, homogenizing, and the serial diluting and plating of the homogenates. The dotted lines that separates the halves of the figure resembles the freezing of the 10 g aliquots.

Ground beef was obtained from the NDSU Meat Lab (ag.ndsu.edu/ansc/facilities/shepperd-arena). Precautionary steps that the slaughter facility undertakes to prevent microbial contamination of muscle meat include rinses of the hot carcass with hot water and 2.5% lactic acid (Birko Corp., Henderson, Colo.). Prior to cutting the meat, cattle halves are incubated for two weeks at a temperature between 0 and 2.2° C. For this Example, meat from two animals was ground within the NDSU Meat Lab and consecutively transferred on ice to the research lab where this Experiment was conducted. Approximately 4 pound of ground meat was obtained from two independent slaughter events (FIG. 6). These two original meat samples are referred to as biological replicates throughout this study. Each biological replicate was weighed into five aliquots of 200 g that were supplemented with 0 g, 0.1 g, 0.5 g, 1 g, or 5 g of liquid EAA (Alfa Aesar, Ward Hill Mass.). A total of six aliquots of 10 g were produced from each 200 g aliquot to allow for two technical replicates and determination of bacterial counts at three different time points during the incubation period. Aliquots were stored in Ziploc bags at −20° C.

Determination of the Effect of EAA on Meat Spoilage Bacteria

Meat samples were removed from the freezer and incubated at 10° C. for five days; bacterial counts were determined on days 1, 3, and 5. For one initial experiment, samples were removed after 1 h of incubation at 10° C. This aliquot is not included in FIG. 6.

The content of each bag was transferred into a stomacher bag and Maximum Recovery Diluent (MRD) was added to a total of 50 ml. Meat was homogenized in a Seward Stomacher 400 Circulator (Cole Parmer, Vernon Hills, Ill.). The total bacterial count of each homogenate was determined by plating serial dilutions on Plate Count Agar (PCA). *Pseudomonads* were determined with *Pseudomonas* Selective Agar (PSA), *lactobacilli* with All Purpose Tween agar (APT), *B. thermospacta* with Streptomycin sulphate, Thallous Acetate and Actidione agar (STAA), and Enterobacteriaceae with Violet Red Bile Glucose agar (VRBG). For the composition of these media, see TABLE 7 (BD: Becton Dickinson). Each serial dilution was plated onto two separate agar plates to allow for two plate replicates (FIG. 6).

TABLE 7

Composition of the bacterial growth media

| Name | Abbreviation | Composition | Brand |
|---|---|---|---|
| Plate count agar | PCA | 5 g/l tryptone, 2.5 g/l yeast extract, 1 g/l glucose, 15 g/l agar, pH 7.0 | Difco BD |
| *Pseudomonas* agar | PSA | 16 g/l gelatin peptone, 10 g/l casein hydrolysate, 10 g/l $K_2SO_4$, 1.4 g/l $MgCl_2$, 0.5 mg/ml cetrimide, 0.5 mg/ml fucidin, 2.5 mg/ml cephalosporin, 11 g/l agar, pH 7.1 | Oxoid |
| All purpose tween agar | APT | 7.5 g/l yeast extract, 12.5 g/l pancreatic digest of casein, 10 g/l dextrose, 5 g/l sodium citrate, 0.001 g/l thiamine HCl, 5 g/l NaCl, 5 g/l $K_2HPO_4$, 0.14 g/l $MnSO_4 \cdot H_2O$, 0.8 g/l $MgSO_4 \cdot 7H_2O$, 0.04 g/l $FeSO_4$, 0.2 g/l polysorbate, 15 g/l agar, pH 6.7 | Difco BD |
| Streptomycin sulphate, thallous acetate, actidione agar | STAA | 20 g/l peptone, 2 g/l yeast extract, 1 g/l $K_2HPO_4$, 1 g/l $MgSO_4 \cdot 7H_2O$, 500 µg/ml streptomycin sulphate, 50 mg/ml thallous acetate, 50 mg/ml cycloheximide, 13 g/l agar, pH 7.0 | Oxoid BD |

TABLE 7-continued

Composition of the bacterial growth media

| Name | Abbreviation | Composition | Brand |
|---|---|---|---|
| Violet red bile glucose agar | VRGB | 7 g/l peptone, 3 g/l yeast extract, 1.5 g/l bile salts No. 3, 5 g/l NaCl, 0.03 g/l neutral red, 0.002 g/l crystal violet, 10 g/l glucose, 12 g/l agar, pH 7.4 | Oxoid |
| Luria Bertani broth | LB | 10 g/l tryptone, 5 g/l yeast extract, 5 g/l NaCl | Difco BD |
| Brain heart infusion | BHI | 7.7 g/l calf brain infusion solids, 9.8 g/l beef heart infusion solids, 10 g/l proteose peptone, 5 g/l NaCl, 2 g/l glucose, 2.5 g/l $Na_2HPO_4$, pH 7.4 | Difco BD |
| Tryptic soy broth | TSB | 17 g/l pancreatic digest of casein, 3 g/l papaic digest of soy bean, 5 g/l NaCl, 2.5 g/l $K_2HPO_4$, 2.5 g/l glucose, pH 7.3 | Difco BD |
| Maximum recovery diluent | MRD | 1 g/l peptone, 8.5 g/l NaCl, pH 7.0 | |
| Sorbitol McConkey agar | SMAC | 15.5 g/l peptone, 3 g/l proteose peptone, 10 g/l D-sorbitol, 1.5 g/l bile salts, 5 g/l NaCl, 0.03 g/l neutral red, 0.001 g/l crystal violet, 15 g/l agar, pH 7.1 | Difco BD |
| Tryptic soy agar | TSA | 15 g/l pancreatic digest of casein, 5 g/l papaic digest of soy bean, 5 g/l NaCl, 15 g/l agar, pH 7.3 | Difco BD |

Each experiment was performed in a total of 8 replicates (2 biological replicates×2 technical replicates×2 plate replicates). To prepare for analysis, the data sets were preprocessed by determining the averages for the 2 plate replicates. Data were analyzed for each EAA concentration and selective media and expressed as CFU/g of meat or $\log_{10}$ CFU/g of meat. The lower limit of detection was 49 CFU, which is the equivalent of 1.69 $\log_{10}$. This number was used for all experiments that yielded zero colonies from the undiluted homogenate. To determine log reductions, the $\log_{10}$ CFU/g of meat at a given concentration of EAA was subtracted from that obtained for the untreated control piece of meat. Average and standard errors were calculated across the two biological and two technical replicates. Statistical analysis was started with an Analysis of Variance (ANOVA) test that compared the means of the $\log_{10}$ CFU/g data across concentrations, days, and biological replicates to determine the main effects. For comparisons that determined statistically significant differences between the means (p-value below 0.05), Fisher's Least Significant Difference (LSD) test and a pairwise Student's t-test were performed as post hoc test to determine which of the groups were different from the others.

Determination of the Effect of EAA on *E. coli* O157:H7 and *S. enterica*

The *E. coli* O157:H7 strain used for this experiment was ATCC 43894, previously made resistant to streptomycin sulphate. The *S. enterica* strain was a clinical isolate of *S. enterica* Typhimurium, designated FSL R6-0207 and provided by Dr. T. Bergholz (NDSU). *S. enterica* was adapted to 50 μg/ml of nalidixic acid as described previously. Bacterial strains were stored at −80° C. in their original growth medium, supplemented with 10% dimethyl sulfoxide. Bacteria were plated onto Luria Bertani agar (LB) prior to each experiment.

Bacterial inocula were prepared from *E. coli* O157: H7 grown in liquid Brain Heart Infusion broth (BHI, TABLE 7), supplemented with 1,000 μg/ml of streptomycin sulphate and *S. enterica* grown in Tryptic Soy Broth (TSB, TABLE 7), supplemented with 50 μg/ml of nalidixic acid. Cultures were incubated at 37° C. overnight on a rotary shaker at 150 rpm. 2 ml from each overnight culture was added to 18 ml of fresh broth and incubated at 37° C. for 2 h. Cultures were diluted with Maximum Recovery Diluent (MRD, TABLE 7) to a bacterial count of 4×10⁴ CFU/ml, determined by plating serial dilutions onto LB agar plates. 10 g meat portions that were treated with 0.5% EAA were removed from the freezer, thawed, inoculated with 1 ml of the respective inoculum and mixed within the Ziploc bag. Meat bags were incubated at 10° C. for 5 days and treated as described under 2.2. *E. coli* O157:H7 were enumerated on Sorbitol MacConkey agar (SMAC, TABLE 7), supplemented with 1,000 μg/ml streptomycin sulphate. Bacterial counts for *S. enterica* were determined on Tryptic Soy Agar (TSA, TABLE 7), supplemented with 50 μg/ml nalidixic acid. Data processing was performed as described under 2.2. Statistical analysis was done with Student's t-test to determine the statistical significance of the difference between bacterial counts obtained at each concentration of EAA and the untreated meat sample. A p-value less than 0.05 indicated that the difference between the data obtained from treated and untreated meat pieces was statistically significant.

Results

EAA Reduced Spoilage Bacteria on Ground Beef

Figure 7:
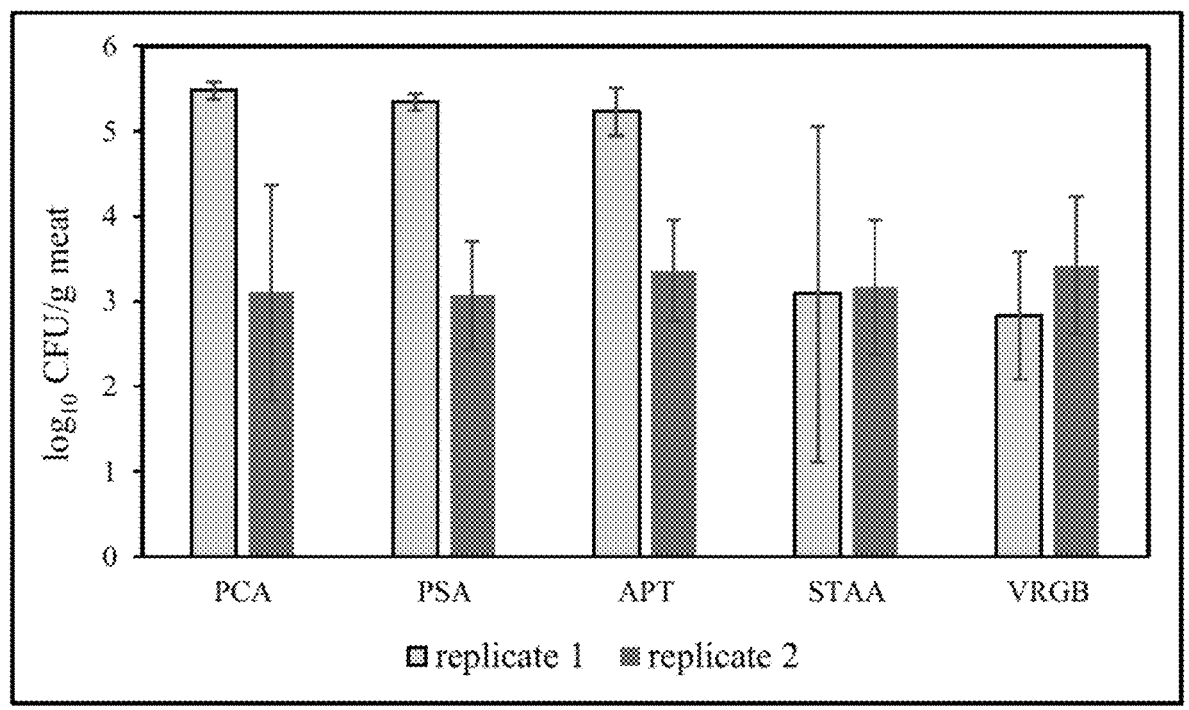
FIG. 7 shows a graph comparing two biological replicates. Meat pieces were removed from the freezer and incubated at 10° C. for one hour. The total bacterial counts from the homogenate of the first replicate are indicated in light grey bars, the dark grey bars resemble the counts for the second replicate. Each biological replicate was tested in two technical and two plate replicates. The average and standard error across the four replicates is shown.

In an initial experiment, the total bacterial load and common meat spoilage bacteria on untreated meat pieces were compared between the two biological replicates. For this experiment, meat samples were removed from the 10° C. incubator after 1 h and bacteria were enumerated on the various plates (FIG. 7). For the total plate count from the PCA plates, the pseudomonad count from the PSA plates, and the *lactobacilli* count from the APT plates, there was a difference of approximately 2.5 logs between biological replicates 1 and 2 (light grey vs dark grey bars). For *B. thermospacta* and Enterobacteriaceae, the bacterial load prior to the 10° C. incubation was low in both biological replicates. These apparent differences between the biological replicates were considered during the statistical analysis of the data. An additional observation was made from this experiment; the counts for *pseudomonads* and *lactobacilli* (in replicate 1) were considerably higher than those for *B. thermospacta* and Enterobacteriaceae. This is in agreement with current literature.

To determine the effect of EAA on the total bacterial counts and beef spoilage bacteria, bacteria were enumerated on 10 g aliquots of ground beef, either left untreated or treated with increasing concentrations of EAA. The log reduction data are presented in FIG. 8. TABLE 8 lists the outcomes of the statistical analysis. For all media plates, the ANOVA provided evidence that there were statistically significant differences between the $\log_{10}$ CFU/g data from the 5 different concentrations of EAA (column 1) and the three different days of harvest (column 2). For the total plate count, pseudomonads, and lactobacilli, the two different biological replicates also yielded data that were different from one another with statistical significance (column 3). This is consistent with observations from FIG. 7. The interaction between concentrations and days yielded differences of statistical significance for the total plate count only with a p-value of 0.0106 (data not shown). This interaction was not further investigated because the lines in the profile plot did not intersect. The post hoc test that was performed on the means of the days calculated that data from all days were different from one other for all of the media plates (data not shown).

TABLE 8

Statistical analysis of the data from the EAA treatments (spoilage bacteria)

| Concentration (p-value)[1] | Day (p-value)[2] | Biol. Repl. (p-value)[3] | Different from 0%[4] | Different from one another[5] |
|---|---|---|---|---|
| PCA, total bacterial count | | | | |
| <0.0001 | <0.0001 | <0.0001 | 0.5 | 0.5 from 0.05 |
| | | | 2.5 | 2.5 from all others |
| PSA, Pseudomonas | | | | |
| <0.0001 | <0.0001 | <0.0001 | 0.5 | 0.5 from 0.05 |
| | | | 2.5 | 2.5 from all others |
| LPT, Lactobacilli | | | | |
| <0.0001 | <0.0001 | <0.0001 | 0.5 | 0.5 from 0.05 |
| | | | 2.5 | 2.5 from all others |
| STAA, B. thermospacta | | | | |
| 0.0010 | 0.0004 | NA | 0.5 | 0.5 from 0.05 and 0.25 |
| | | | 2.5 | 5 from 0.05 and 0.25 |
| VRGB, Enterobacteriaceae | | | | |
| 0.0009 | <0.0001 | NA | 0.5 | 0.5 from 0.05 |
| | | | 2.5 | 5 from all others |

[1] This is the p-value from the ANOVA, where the means of the $\log_{10}$ CFU/g values were compared across the five different concentrations.
[2] This is the p-value from the ANOVA, where the means of the $\log_{10}$ CFU/g values were compared across the three different days.
[3] This is the p-value from the ANOVA, where the means of the $\log_{10}$ CFU/g values were compared across the two different biological replicates.
[4] Concentrations are listed that resulted in a grouping that was different from the untreated (0% PEA) control meat pieces, as determined by Fisher's LSD test and Student's t-test.
[5] Concentrations are listed that resulted in a grouping that differed from any other concentration (except 0% PEA).

Figure 8A:
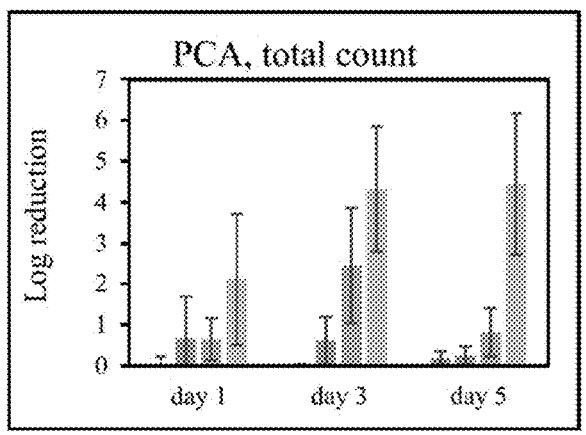
FIGS. 8A-E show graphs illustrating bacterial counts of spoilage bacteria upon treatment with EAA. (A) Shows the log reductions for the total bacterial count from the PCA plates after 1, 3, and 5 days of incubation at 10° C. (B) Shows the log reductions for *pseudomonads*. (C) Shows the log reductions for *lactobacilli*. (D) Shows the log reductions for *B. thermospacta*. (E) Shows the log reductions for Enterobacteriacea. Each experiment was performed in eight replicates. Averages and standard errors were calculated over the 2 biological and 2 technical replicates, after pre-averaging the plate replicates. Light blue, untreated control; orange, 0.05% of EAA; grey, 0.25% EAA; yellow, 0.5% EAA; dark blue, 2.5% EAA.
Figure 8B:
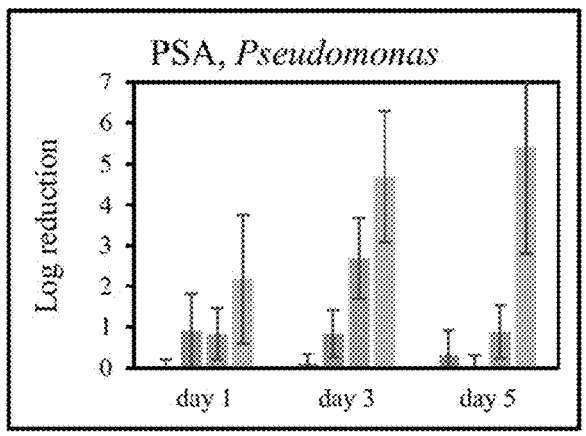
Figure 8C:
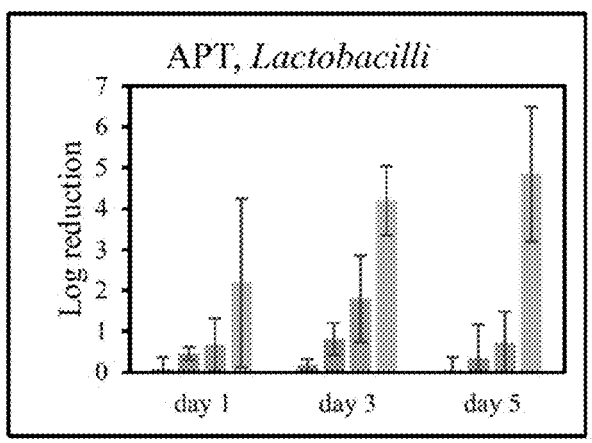
Figure 8D:
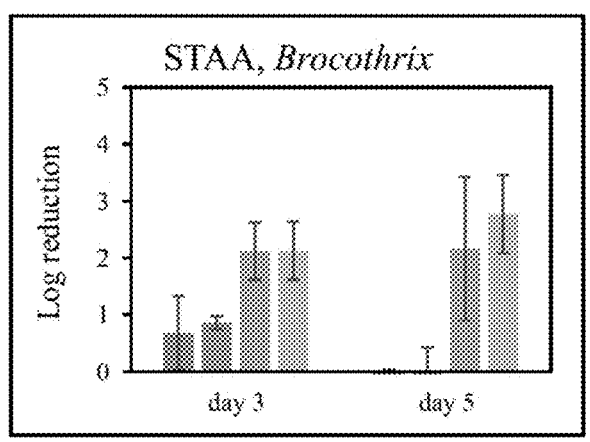
Figure 8E:
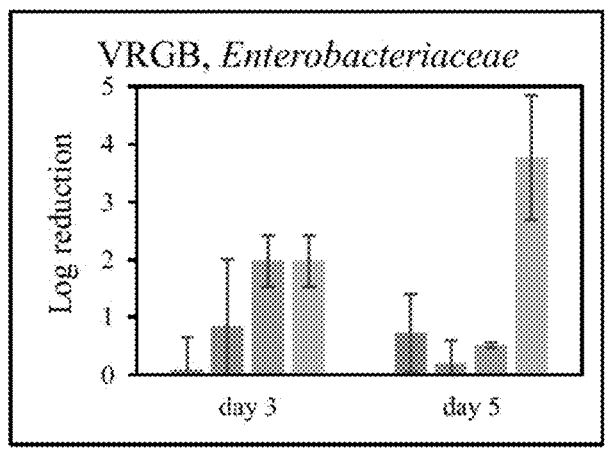

After 1 day of incubation at an abusive temperature of 10° C., the total bacterial count from the PCA plates decreased with increasing concentrations of EAA to a maximum log reduction of 2.1 at 2.5% of EAA (FIG. 8A). At the more practical concentration of 0.5% of EAA, a 0.65 log reduction was still observed. With increasing time of incubation, the effect of EEA increased for the two higher concentrations. 0.5% EAA caused a log reduction of 2.4 after 3 days of incubation, 2.5% EAA was most effective after 5 days of incubation, reducing the total bacterial count by 4.3 logs. Statistical analysis revealed that the 0.5% and 2.5% samples yielded data that were significantly different from those of the untreated controls (TABLE 8, column 4).

For pseudomonads and lactobacilli, log reductions between 1.8 and 4.6 were observed for the high concentrations of 0.5 and 2.5% of EAA after three days of incubation at 10° C. For B. thermospacta, the post hoc test determined that the meat pieces that had been treated with 0.5% and 2.5% EAA yielded $\log_{10}$ CFU/g meat data that differed from the untreated controls with a statistically significant difference. Log reductions for Enterobacteriaceae were up to 3.8 after 5 days of incubation with a concentration of 2.5% of EAA. Data from the 0.5% and 2.5% samples were determined as statistically significantly different from the untreated control. Therefore, it was concluded that EAA reduces viable counts for all spoilage bacteria tested.

EAA Reduced Bacterial Counts of E. coli O157:H7, but not S. enterica.

Figure 9:
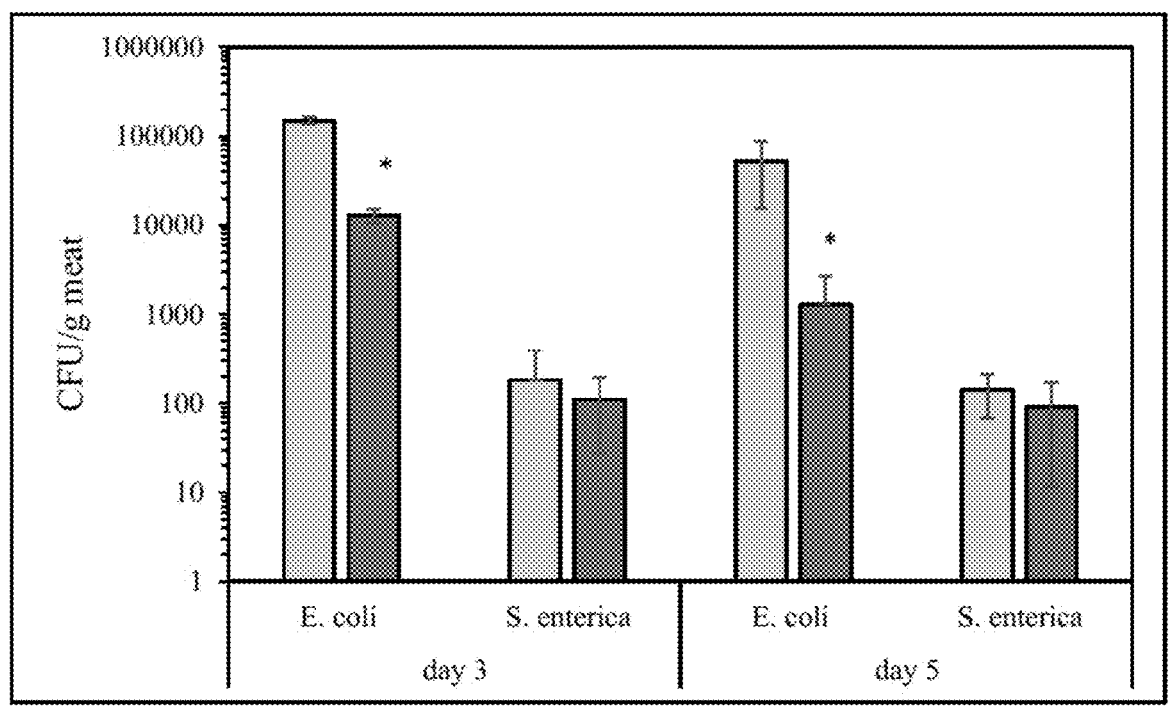
FIG. 9 shows a graph illustrating bacterial counts of pathogens upon treatment with EAA. The CFU/g of meat data for *E. coli* O157:H7 and *S. enterica* is shown after 3 and 5 days of incubation. Averages and standard errors were calculated over the 2 biological and 2 technical replicates, after pre-averaging the plate replicates. Light grey bars, *E. coli*; dark grey bars, *S. enterica*.

In a second experiment, whether a reduction in the natural flora of the meat might cause an increase in pathogens was tested. This was done at an EAA concentration of 0.5%. CFU/g meat data are presented in FIG. 9. At day 1, neither E. coli O157:H7 nor S. enterica yielded bacterial counts that were above the detection limit of 49 CFU/ml (data not shown). At day 3, EAA decreased the bacterial counts for E. coli O157:H7 by about 1 log. At day 5, the reduction in the E. coli count caused by EAA was 1.6 log. For S. enterica, although a reduction in the bacterial counts by the EAA treatment was not observed, the pathogen was also not increased. The t-test yielded p-values of 0.011 and 0.018 for E. coli at days 3 and 5, respectively. For S. enterica, the corresponding p-values were 0.19 and 0.33. Therefore, it was concluded that the EAA treatment reduced E. coli O157:H7 and did not increase S. enterica.

Summary of Results.

In this Example, EAA was mixed with 200 g of ground beef in a range of concentrations, 10 g aliquots of meat were incubated at 10° C. for 5 days and bacterial counts were determined at day 1, day 3, and day 5. Spoilage bacteria were enumerated by plating serial dilutions of the meat homogenates onto selective agar plates. For the detection of pathogenic bacteria, treated and untreated meat aliquots were inoculated with the respective bacteria prior to the 10° C. incubation. When EAA was mixed with ground beef in a concentration of 0.5% w/w, a 2.4 log reduction in total bacterial counts was observed after 3 days of incubation. Under the same conditions, log reductions for common beef spoilage bacteria were 2.6 for pseudomonads, 1.8 for lactobacilli, 2.1 for Brocothrix thermospecta, and 2 for Enterobacteriaceae. Log reductions for the pathogenic bacteria were 1 for Escherichia coli O157:H7 and 0.2 for Salmonella enterica serovar Typhimurium, also determined after 3 days of incubation. Importantly, the pathogens were not increased due to the reduction of competing flora.

Discussion

Altogether, EAA had a dramatic effect on the bacterial counts of the meat samples during the 5 days of the incubation. At day 1 of incubation at abusive temperature, the total bacterial count for the unsupplemented meat sample was 6.4 $\log_{10}$, which is below the 8 $\log_{10}$ that were defined as spoilage long time ago. At day 3, however, the total count had increased to 9 $\log_{10}$, but was reduced to 7.8 and 6.6 $\log_{10}$ in the presence of 0.5% and 2.5% of EAA, respectively. At the same time point, externally added E. coli was reduced from 5.2 $\log_{10}$ to 4.1 $\log_{10}$ in the presence of 0.5% EAA. For this reason, EAA is proposed herein as a novel inhibitor of the natural microflora and E. coli O157:H7 on ground beef at a concentration of 0.5% w/w with a maximum time of storage at an abusive temperature of 10° C. of 3 days.

Whether as agrochemical or food additive, chemicals in food have increased over the past 100 years and special care has to be taken when evaluating real and perceived risks. Although there is always the perceived risk by the customer, which is more difficulty to predict, there are several pieces of evidence that indicate toxicity of EAA should not be a problem at the 0.5% w/w concentration recommended herein. For one, a skin irritation study was done with albino rabbits that had 0.5 ml EAA applied under semi-occlusive cover to the intact skin. After 4 hours of exposure, no indications of irritation were detected. The irritating potential to the eye was also determined with isolated bovine corneas, which showed that EAA caused moderate eye irritation that was fully reversible after seven days. Additionally, genotoxicity was determined with S. enterica, E. coli, and B. subtilis. No mutagenicity was detected for S. enterica and B. subtilis. In E. coli, a mutagenic effect could be detected that exhibited a linear concentration dependence.

Furthermore, i) the FDA has approved EAA as a food additive under 21CFR172.515; ii) EAA is used as flavoring ingredient under Flavis No 9.402; iii) according to the MSDS by Science Lab, the $LD_{50}$ for the toxicity in rats after oral application is 3.98 g/kg of body weight; and iv) a toxicology study with rats demonstrated that feeding rats with up to 300 mg/kg body weight of EAA every day for 28 days did not result in any general health defects or changes in hematology, serum, urine, or renal function. The $LD_{50}$ in rats of 3.98 g/kg of body weight equates to 279 g for a 70 kg person. Meanwhile, at a concentration of 0.5% EAA, ground beef would only contain 1 g of EAA in 200 g of meat. Therefore, to meet the $LD_{50}$ level of 279 g of EAA, a person would have to eat 55 kg of meat on one single day.

In view thereof, this Example demonstrates that EAA can be used to reduce the beef meat spoilage bacteria and that EAA reduces at least the pathogenic E. coli O157:H7. Accordingly, EAA is shown herein to be a novel treatment to reduce the natural microbiota of ground beef.

Example 3

Currently in the United States, about 150 million intravascular catheters are used every year for critically ill patients, such as patients with chronic renal failure, cancer patients, ICU patients, and patients with long-term illness. An intravascular catheter or central line can be used for hemodynamic monitoring, renal replacement therapy, nutritional support, or medication administration. A central line catheter is a long, flexible tube usually made of polytetrafluoroethylene (Teflon), polyurethane, or silicone. This requires surgical implantation, where the catheter is threaded into the jugular vein and guided into the superior vena cava. This however is not ideal because the patient becomes more vulnerable to developing a blood clot or contracting a central line-associated bloodstream infection (CLABSI). CLABSIs can be caused by bacterial biofilms, which are a group of bacteria that can attach or adhere to a surface. The phenotypic changes that bacteria undergo as they form the biofilm community cause difficulties with standard chemical, physical, or biological removal techniques. In addition, CLABSIs are even harder to treat with the emergence of antibiotic resistant strains, causing an increase in morbidity and treatment costs. Last-resort antibiotics, such as methicillin and vancomycin, which were once very effective at treating CLABSIs are becoming insufficient due to overuse. CLABSIs caused by antibiotic resistant strains, such as methicillin resistant Staphylococcus aureus (MRSA) and vancomycin resistant S. aureus (VRSA) are becoming more prevalent.

Since the formation of bacterial biofilms on central venous catheters continues to cause problems, current research efforts have been aimed at mitigating this problem by incorporating traditional antibiotics and antimicrobials directly into the materials of biomedical devices. When CVCs were integrated with chlorhexidine-silver sulfadiazine or minocycline-rifampicin, bacterial colonization and CLABSI occurrence was shown to be reduced. However, recent studies have shown that the antimicrobial effect of chlorhexidine and silver sulfadiazine coated catheters only lasted 48 h and may not be sufficient for reducing catheter related infections. Another strategy has been to use metal nanoparticles to coat or embed into the catheter material. Both silver and copper nanoparticles have been used due to their anti-microbial properties. In vitro, Ag/Cu-coated catheters have been shown to prevent the attachment of methicillin-resistant Staphylococcus aureus (MRSA). The Ag/Cu coated catheter was also shown, using a rat animal model, to reduce the occurrence of catheter-related infections (though not significantly) and bacteremia in comparison to non-coated catheters. However, these materials are accompanied by high production costs, limited lifetimes, the emergence of resistant bacterial strains, and have even been shown to increase antibiotic resistance in some bacterial strains. In addition, high doses of silver can have toxic effects on the human body and have been shown to accelerate thrombin formation and platelet activation when catheters were coated with silver nanoparticles.

Another strategy to reduce catheter-related infections has been to use antibiotic-lock therapy (ALT), where high concentrations of antibiotic solutions are left to dwell in the catheter when the catheter is not in use. Traditional antibiotics like vancomycin, cefazolin, ceftazidime, ciprofloxacin, gentamicin, and ampicillin are typically used for ALT treatment. ALT treatment was shown to be effective at reducing CLABSI of cancer patients, however no significant conclusions could be drawn due to differences in administration and dwell time. Unfortunately, ALT contributes to the overuse of antibiotics and could increase the emergence of antibiotic resistant bacterial strains. Despite all these efforts, incidences of catheter-related infections continue to occur and an urgent need for novel approaches to inhibit biofilm is evident.

This Example is directed to development of a silicone based model, resembling an intravenous catheter with antibiotic-lock therapy, to test an application of EAA. The research presented in this Example constitutes a different approach towards the development of novel biofilm inhibiting antimicrobials. Instead of using traditional antibiotics to inhibit biofilm formation, this Example expands upon on the Examples above by testing the effect of EAA supplied in the liquid bacterial growth medium on a selection of pathogens relevant to the clinical setting. In a first step towards the goal of developing a novel biofilm inhibiting antimicrobial flush, hemodialysis fistula sets were inoculated to simulate a catheter and ALT was mimicked by leaving EAA solutions in the tubing to treat the bacterial biofilm. Although described herein with regard to catheters, this Example is equally applicable to other similar tubing used to transport liquids where bacterial contamination/growth are possible (e.g., food industry—brewing, beverage, etc.). The biofilms in the tubings were subsequently assessed for their ATP content by the ATP assay, their biofilm biomass by the crystal violet (CV) assay, and their viable cell count by plating serial dilutions on selective agar plates. The highest concentrated EAA flush at 100 mg/ml of EAA reduced the ATP content of the biofilm in the tubing by 100% for almost all of the tested bacterial pathogens. Thus, EAA is shown to be an alternative for treatment of bacterial biofilms and as an ALT.

Materials and Methods

Bacterial Strains.

Pathogenic bacterial strains used in this study include *Pseudomonas aeruginosa* (ATCC 15442), *Staphylococcus aureus* (ATCC 25923), the enterohemolytic *E. coli* (EHEC) EDL932, two uropathogenic *E. coli* (UPEC), UMN026 and CFT073, *Yersinia enterocolitica* 8081c (ATCC 9610), *Cronobacter sakazakii* (BAA-894), and *Serratia marcescens* (BAA-632). Bacterial strains were maintained as freezer stocks at −80° C. in 8% dimethyl sulfoxide (DMSO). Prior to each experiment, the *E. coli* strains were plated onto Luria Bertani (LB; 10 g/l tryptone, 5 g/l NaCl, 5 g/l yeast extract) agar plates. *P. aeruginosa* and *S. aureus* were plated onto tryptic soy agar (TSA; 15 g/l tryptone, 5 g/l soytone, 5 g/l NaCl, 15 g/l agar) plates. Plates were incubated over night at 37° C.

Formation of Biofilm in Silicone Tubing.

Figure 10A:
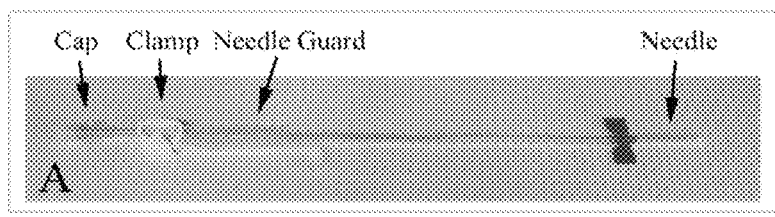
FIGS. 10A-D show images illustrating preparation of a hemodialysis fistula set to grow biofilm in silicone tubing. (A) Shows a fistula set as it was removed from the plastic protector. (B) Shows the needle guard pushed over the needle. (C) Shows the needle cut off, the cap removed, and a syringe inserted. (D) Shows the cap attached to the opposite end for incubation.
Figure 10B:
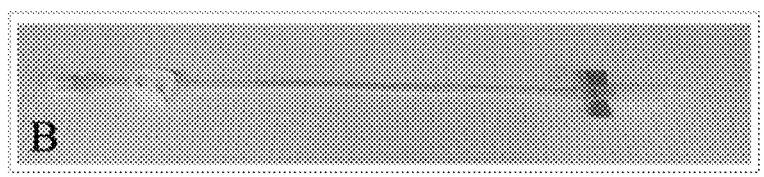
Figure 10C:
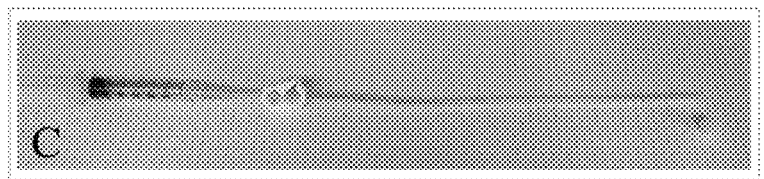
Figure 10D:
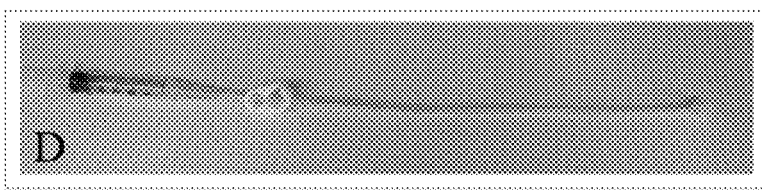

Liquid overnight cultures (10 ml) in TSB were centrifuged at 4,500 g for 10 min, bacteria were resuspended in TSB to an $OD_{600}$ of 0.05. An AV Fistula Needle 17 Ga. X 1¼" Single Pk FW with MasterGuard® anti-stick needle protector was purchased from Medisystems Corporation (Lawrence, Mass.). The key piece of this Hemodialysis Fistula Set is a 12 inch long piece of silicone tubing with an inner diameter of ⅛ inch and an outer diameter of ⅜ inch (FIG. 10A). Prior to inoculating with bacteria, the needle guard was pulled over the needle and cut off (FIG. 10B). An alcohol swab was used to remove the cap at the other end of the tubing to be used later as a cap on the end of the tubing where the needle was removed. Using a sterile syringe, the tubing was inoculated with 3 ml of inocula (FIG. 10C). The clamp on the tubing was then closed and the syringe was left attached to the tubing. Finally the cap that was saved earlier was attached to the end of the tubing (FIG. 10D).

Two pieces of tubing were inoculated for each bacterial strain, an additional tubing was incubated with TSB to serve as negative control. The three tubings were incubated on an absorbant pad at 37° C. for 4 days. On the fourth day, the two tubings that were inoculated with the bacteria either received 3 ml of TSB or 3 ml of EAA treatment. In four separate experiments, the concentration of EAA in the treatment was either 100 mg/ml, 10 mg/ml, 5 mg/ml, or 1 mg/ml in TSB. New sterile syringes were used, attached, and left on the tubings. No new media was pushed through the control tubing. EAA treatments were administered at days 4, 8, and 11. Incubation was continued until two weeks had elapsed.

Performance of the Biofilm Assays in Silicone Tubing.

At the end of the incubation, biofilms were characterized with the CV and ATP assays. All tubings were flushed with 3 ml of PBS using a new sterile syringe. The syringe was detached and 3 ml of air was pushed through the tubing to flush out any liquid. Starting at the end that originally had the syringe attached, a 4 inch section of tubing was cut off with a sterile razor blade. From the 4 inch piece of tubing, six sections of about 1 mm were cut for the biofilm assays. Three of these pieces of tubing were transferred to one microcentrifuge tube to be used for the CV assay. The other three sections of tubing were transferred into three separate microcentrifuge tubes, each filled with 1 ml of PBS to be used for the ATP assay and the determination of the viable cell counts. A new razor blade was used to cut each piece of tubing.

For the ATP assay, the three microcentrifuge tubes that contained one section of silicone tubing and 1 ml of PBS were vortexed thoroughly for a minute. Each individual tube was then vortexed for 10 seconds prior to transferring 100 µl to 1 well of a 96-well white plate. Then, 100 µl of BacTiter-Glo™ reagent was added to each well. The plates were covered with tinfoil, solutions were thoroughly mixed, and plates were placed on a rotating shaker for 5 min. After this incubation, luminescence was read using the Synergy H1 Hybrid Reader. Data are expressed as relative light units (RLU).

For the CV assay, 1.0 ml of 0.1% CV in $ddH_2O$ was added to the microcentrifuge tube. The tube was incubated for 15 min. The silicone tubings were rinsed 3 times by using sterile forceps and dipping for 10 s into 3 separate and consecutive microcentrifuge tubes filled with 1 ml of $ddH_2O$. The silicone tubings were then transferred into new individual microcentrifuge tubes, where they were allowed to dry at room temperature for at least 1 h. The CV was extracted by adding 500 µl of 80% ethanol/20% acetone to each microcentrifuge tube. The tubes were vortexed for 30 s and then incubated for 15 min. 0.15 ml of each extract was then transferred into one well of a 96 well polystyrene plate and the $OD_{600}$ values were determined with the Synergy H1 Hybrid Reader.

For the viable cell counts from the biofilms, 100 µl were obtained from the microcentrifuge tube that was used for the ATP assay, serially diluted in 1:10 steps and plated onto TSA plates. Plates were incubated for 24 h at 37° C. Viable cell counts were expressed as colony forming units (CFU) per ml. The lower limit of detection for this assay was 999 CFU/ml.

Data Analysis.

All assays were performed in six replicates, across which the averages and standard errors were calculated. The two inoculated tubings per strain and EAA concentration constituted the biological replicates and the three slices per tubing the technical ones. Percent reductions were calculated as $((a-b)/a) \times 100$, where a is the data (e.g. RLU, $OD_{600}$, CFU/ml) at the control condition (e.g. 0 mg/ml EAA) and b is the data at the experimental condition (e.g. specific concentration of EAA). Log reductions were calculated as $\log_{10} a - \log_{10} b$ for the CFU/ml data from the viable cell count experiment.

Statistical analysis of the data was done with Statistical Analysis Software (SAS) version 8.4. Student's t-test determined the statistical significance of the difference between the mean data for each experimental condition and the mean data at the control condition. Differences were considered significant when the p-value was below 0.05.

Results

Flushes of EAA Reduced the ATP Content and Total Biofilm Biomass in Silicone Tubing for Some Bacterial Pathogens.

Figure 12A:
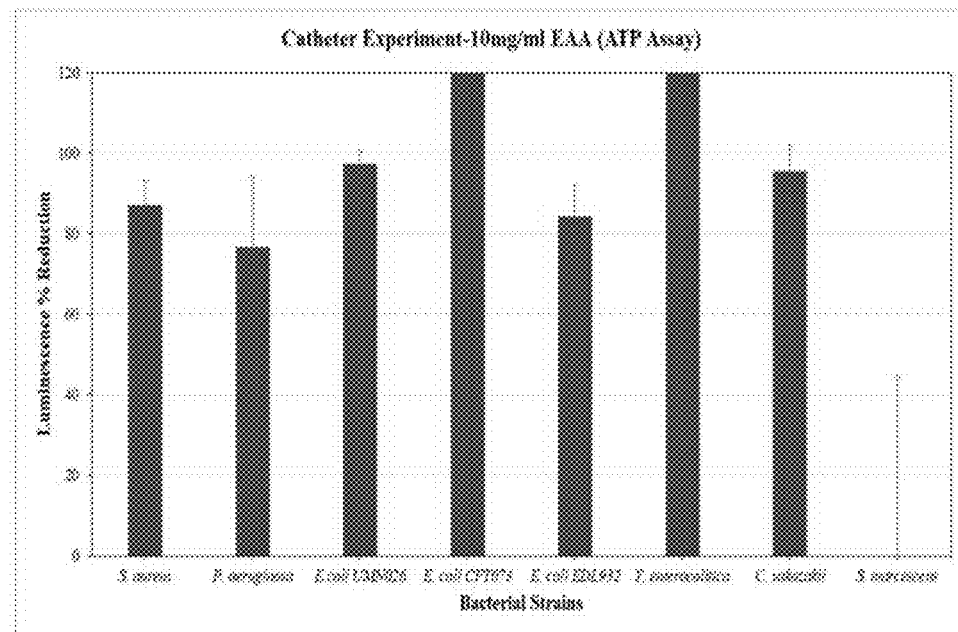
FIGS. 12A-B show graphs illustrating percent reduction of luminescence from the ATP and absorbance from the CV assay when biofilms were treated with 10 mg/ml EAA, compared to biofilms treated with 0 mg/ml of EAA. (A) Shows the ATP content of biofilm grown in the presence of 10 mg/ml, relative to 0 mg/ml of EAA. (B) Shows the absorbance data of the total biofilm biomass from the CV assay.
Figure 12B:
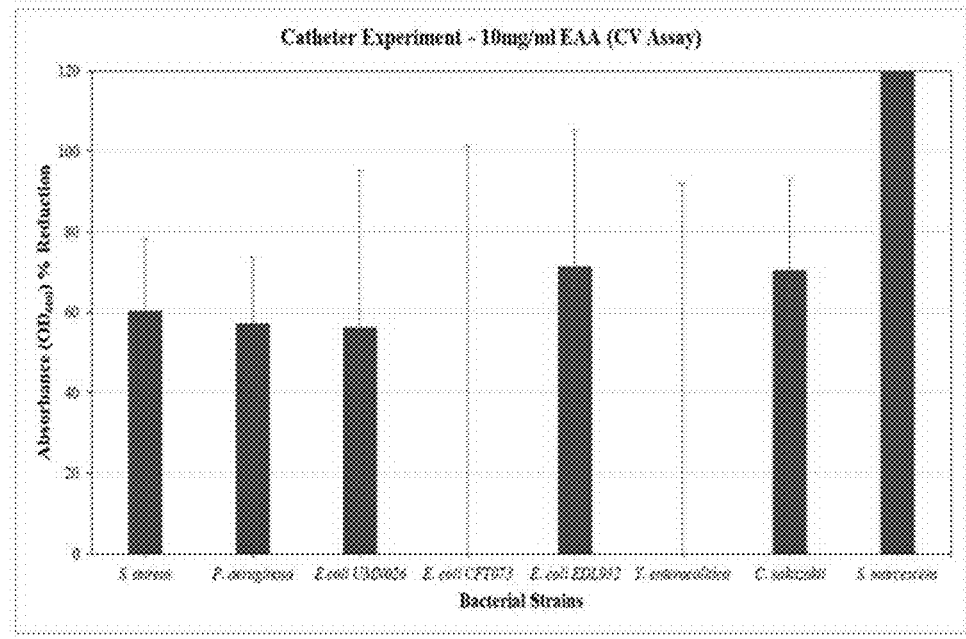
Figure 13A:
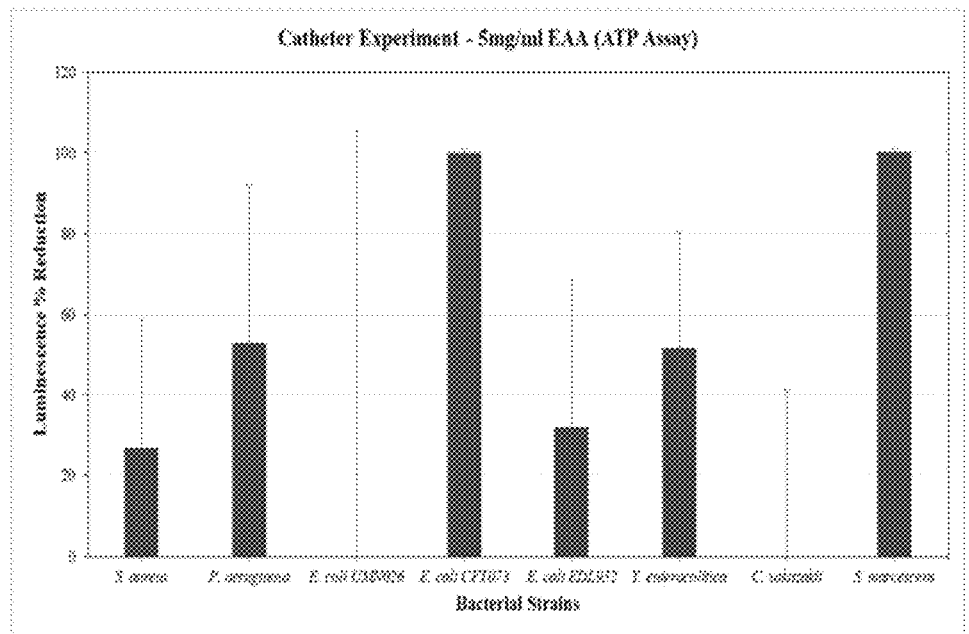
FIGS. 13A-B show graphs illustrating percent reduction of luminescence from the ATP and absorbance from the CV assay when biofilms were treated with 5 mg/ml EAA, compared to biofilms treated with 0 mg/ml of EAA. (A) Shows the ATP content of biofilm grown in the presence of 5 mg/ml, relative to 0 mg/ml of EAA. (B) shows the absorbance data of the total biofilm biomass from the CV assay.
Figure 13B:
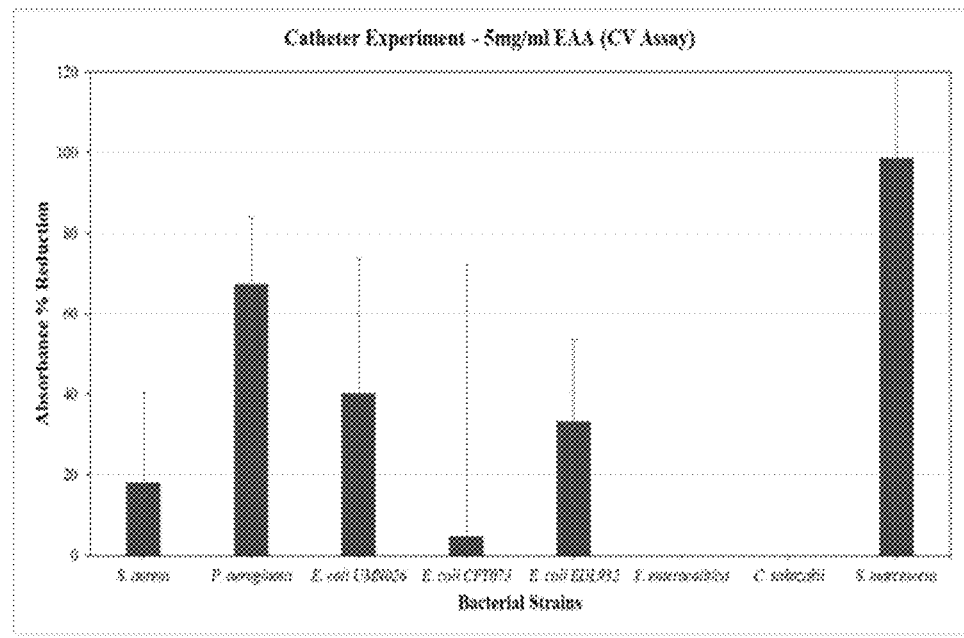
Figure 14A:
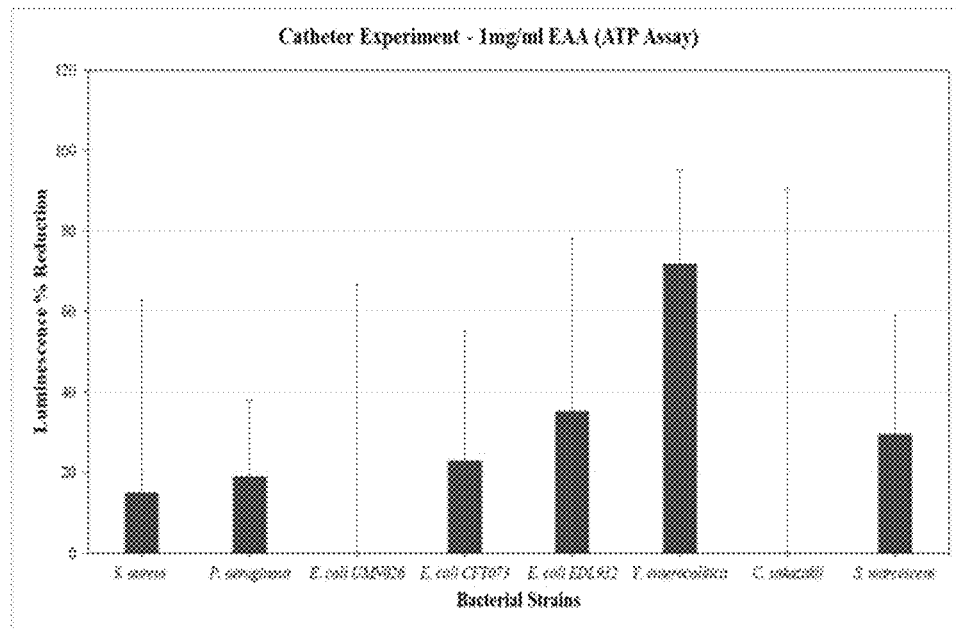
FIGS. 14A-B show graphs illustrating percent reduction of luminescence from the ATP and absorbance from the CV assay when of biofilms treated with a 1 mg/ml EAA flush compared to biofilms treated with 0 mg/ml of EAA. (A) Shows the ATP content of biofilm grown in the presence of 1 mg/ml. (B) Shows the absorbance data of the total biofilm biomass from the CV assay.
Figure 14B:
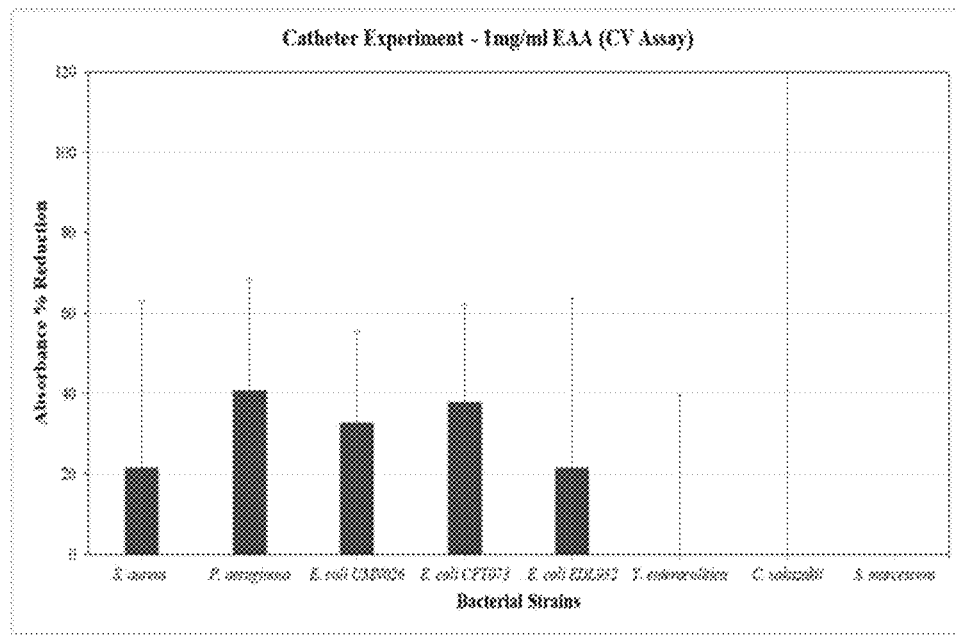

To test one application of EAA, a silicone based model was developed, resembling an intravenous catheter with antibiotic-lock therapy. *S. aureus, P. aeruginosa*, the two UPEC strains, the EHEC strain, *Y. enterocolitica, C. sakazakii*, and *S. marcescens* were grown in the tubings, which were flushed with EAA three times during the 2 week incubation period. In the four experiments, EAA concentrations of 100 (FIGS. 11A-B), 10 (FIGS. 12A-B), 5 (FIGS. 13A-B), and 1 mg/ml (FIGS. 14A-B) were tested.

When the EAA flush was used at a concentration of 100 mg/ml (FIGS. 10A-D), the ATP content of most of the bacterial strains was reduced drastically. *P. aeruginosa* biofilm was not affected by the EAA treatment. However, there was a large amount of variation in the data, which resulted in larger error bars. *S. aureus* biofilm had the second lowest reduction of ATP at 75%. The remaining percent reductions ranged from 98.5% for *E. coli* CFT073 to 105% for *Y. enterocolitica*. When EAA was used at a concentration of 100 mg/ml, the CV content of all biofilms varied across strains and replicates. Percent reductions ranged from 11% for S. aureus to >100% for E. coli EDL932. There was no reduction in biofilm biomass for P. aeruginosa. Student's t-test calculated a statistically significant difference between the ATP content of the biofilms in the absence and presence of EAA for all pathogens except P. aeruginosa. Significant differences between the biofilm biomasses were calculated for E. coli UMN026, E. coli EDL932, Y. enterocolitica, and S. marcescens.

When EAA was used at a concentration of 10 mg/ml (FIGS. 12A-B), reductions of ATP were still around 80% or higher, except for S. marcescens. P. aeruginosa biofilm was not reduced at 100 mg/ml of EAA, but it showed a 76% reduction of ATP when treated with 10 mg/ml of EAA. The CV data for total biomass shows that the effectiveness of EAA to reduce biofilm biomass again depends on the bacterial strain. No reduction in biofilm biomass was observed for E. coli CFT073 and Y. enterocolitica. Percent reductions ranged from 56% for E. coli UMN026 to 71% for E. coli EDL932. Student's t-test calculated a statistically significant difference between the ATP content of the biofilms in the absence and presence of EAA for all the pathogens except S. marcescens. There was a significant difference between the biofilm biomass for all athogens except E. coli CFT073 and Y. enterocolitica.

When the EAA flush was used at a concentration of 5 mg/ml (FIGS. 13A-B), the outcome changed for the ATP content of the biofilm. Most strains still showed some reduction in ATP, but the t-test calculated a statistically significant difference between the data from the treated and untreated samples only for E. coli CFT073 and S. marcescens. These two strains showed near 100% reduction in ATP content of the biofilm, while the rest of the strains either show no reduction in ATP content or produced large error bars due to variation within the data. At 5 mg/ml of EAA, very little reduction in total biofilm biomass was observed for most of the strains. S. marcescens had about 98% reduction and P. aeruginosa had about a 67% reduction in biofilm biomass. E. coli CFT073 had close to 100% reduction of ATP content, but almost no reduction in total biofilm biomass. Student's t-test calculated a statistically significant difference between the ATP content of the biofilms in the absence and presence of EAA for all the pathogens except E. coli UMN026, E. coli EDL932, and C. sakazakii. There was a significant difference in biomass between treated and untreated biofilms only for P. aeruginosa and E. coli UMN026.

When the EAA flush was used at a concentration of 1 mg/ml (FIGS. 14A-B), there was very little reduction in ATP content. None of the reductions in ATP content were significant, except for Y. enterocolitica which had a 71% reduction in ATP content in the biofilm in comparison to the non-treated biofilm. The absorbance data from the CV assay showed little reduction in total biofilm biomass for all strains. The highest reduction of biofilm biomass content was seen for P. aeruginosa at 40%, while S. aureus and the pathogenic E. coli strains had a reduction of biofilm biomass between 20% and 37%. Student's t-test calculated a statistically significant difference between the ATP content of the biofilms in the absence and presence of EAA only for Y. enterocolitica, the only significant difference between the biomass of the treated and untreated biofilms was for P. aeruginosa.

EAA Reduces Viable Bacterial Cell Numbers for S. aureus and P. aeruginosa.

Figure 15A:
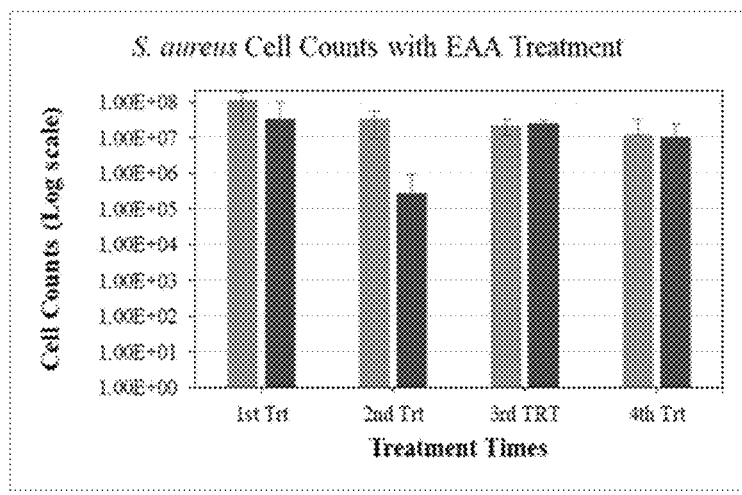
FIGS. 15A-B show graphs illustrating cell counts of *S. aureus* and *P. aeruginosa* from the collected liquid before each treatment with 100 mg/ml of EAA. (A) Shows *S. aureus* viable cell counts in the liquid collected before being flushed with media (orange bars) or 100 mg/ml of EAA (purple bars). (B) Shows *P. aeruginosa* viable cell counts in the liquid collected before being flushed with media (orange bars) or 100 mg/ml of EAA (purple bars).
Figure 15B:
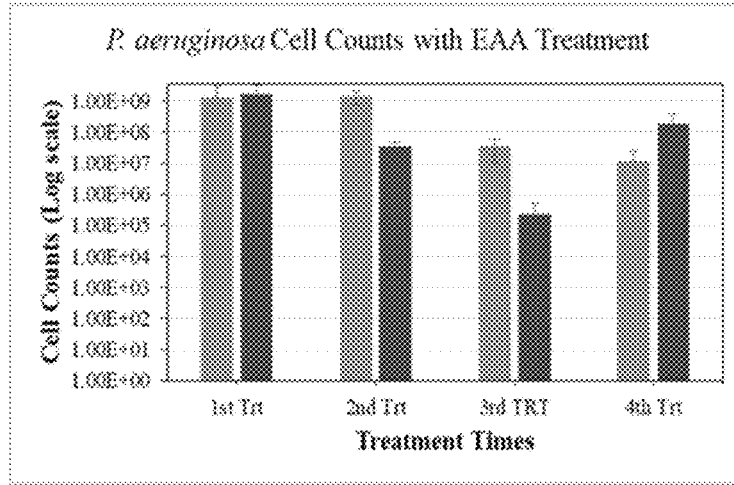

The previous experiments were repeated with S. aureus and P. aeruginosa to determine viable cell counts. FIGS. 15A-B show the cell counts of planktonic cells in the liquid collected before each treatment with 100 mg/ml of EAA for S. aureus (FIG. 15A) or P. aeruginosa (FIG. 15B).

The cell counts of S. aureus collected before the first treatment was administered ($1^{st}$ treatment) were around $10^8$. Right before the second treatment ($2^{nd}$ treatment), a 2-log difference was observed between the viable cells of S. aureus in the liquid of the tubing that had received 100 mg/ml treatment of EAA for the first treatment (purple bars) and the viable cells in the liquid of the tubing that had received only a media flush (orange bars). This difference was not sustainable over the consecutive treatments.

Cell counts of P. aeruginosa collected before the first treatment was administered ($1^{st}$ treatment) were around $10^9$ CFU/ml. Less than a 2-log difference was observed before the $2^{nd}$ treatment between the viable cells of P. aeruginosa in the liquid of the tubing that had received 100 mg/ml of EAA as the first treatment (purple bars) and the viable cells in the liquid of the tubing that had received a media flush (orange bars). Before the third treatment, the difference between the cells numbers of biofilms that had received two treatments of 100 mg/ml of EAA was approximately 2 logs when compared to biofilms that had received the media control.

Interestingly, there was about a 1-log increase between the viable cells in the liquid of the tubing that had received 3 treatments of 100 mg/ml of EAA in comparison to the viable cells in the liquid of the catheter receiving only a media flush after the before the $4^{th}$ treatment. Before the $2^{nd}$ and $3^{rd}$ treatment, there was a statistically significant difference in the viable cells of P. aeruginosa in the liquid of the tubing receiving 100 mg/ml treatments of EAA in comparison to the viable cells in the liquid of the tubing receiving only a media flushes (orange bars).

Figure 16A:
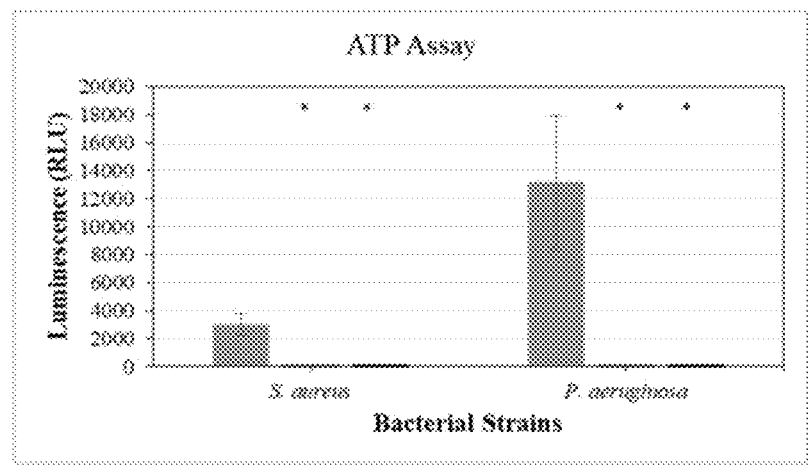
FIGS. 16A-C show graphs illustrating effectiveness of treatment flushes of 100 mg/ml of PEA and EAA in comparison to 0 mg/ml of EAA on ATP content, biofilm biomass, and cell counts of biofilms at the end of inoculation in silicone tubing. The graphs show (A) Biomass, (B) ATP content, and (C) viable cell counts of biofilm grown in the absence (orange bars) or presence of 100 mg/ml of 100 mg/ml of EAA (purple bars) in silicone tubing. Averages and standard errors were determined across 6 replicates.
Figure 16B:
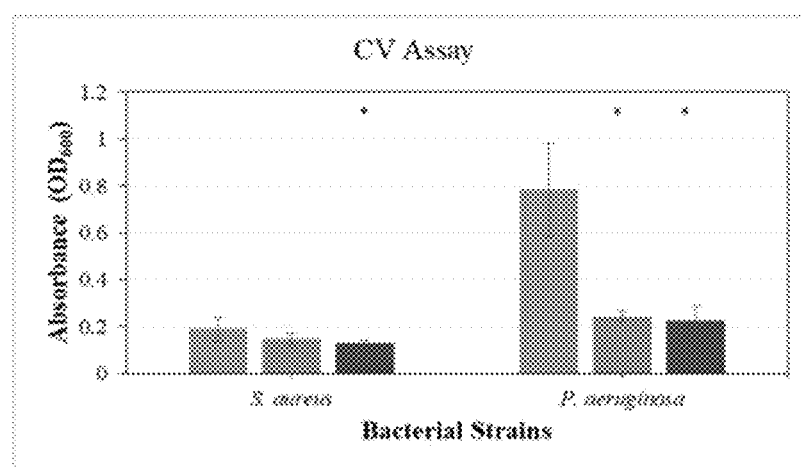
Figure 16C:
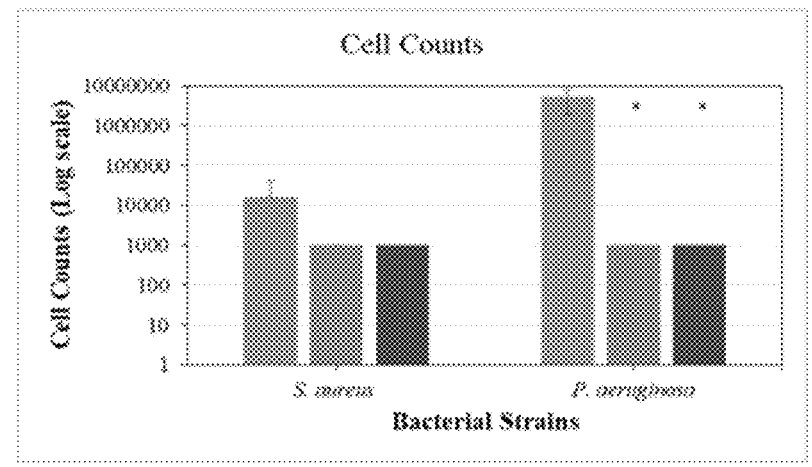

Finally, the viable cells within the biofilm of S. aureus and P. aeruginosa were determined at the end of the two week incubation (FIGS. 16A-C). From the ATP assay (FIG. 16A), it was concluded that treatments with 100 mg/ml of EAA just about abolished the biofilm for both S. aureus and P. aeruginosa. The difference in ATP in the presence and absence of EAA was statistically significant for both strains. Biofilm biomass from the CV assay (FIG. 16B) yielded a much smaller difference between the biofilm that was treated with EAA (purple bars) and the untreated control (orange bars) for S. aureus, but still showed a reduction by EAA from 0.78 to 0.24 $OD_{600}$ that was statistically significant for P. aeruginosa (FIG. 16B).

With the viable cell counts (FIG. 16C), S. aureus had a reduction of about 1-log in viable cells when the bacteria were treated with 100 mg/ml of EAA, while P. aeruginosa cell counts were reduced by EAA by about 3 logs. It is possible that the log reduction for S. aureus in the viable cell counts is an underestimate due to the low cell number in the untreated control and the fact that 999 CFU/ml was the lower limit of detection for the instant assay.

DISCUSSION

A major finding of this Example was that EAA was able to reduce ATP content, biofilm biomass, and cell counts of bacterial biofilms that had formed inside of silicone tubing. The Example was designed to mimic antibiotic-lock treatments in an intravenous catheter, which are surgically implanted into the heart. The bacteria for this study were selected for their relevance to CLABSI and other medical device infections. In a new report on the pathogen distribution among pediatric healthcare-associated infections to the National Healthcare Safety Network, S. aureus ranked first in overall incidences, second in the occurrence of CLABSI, and 12$^{th}$ for catheter related urinary tract infections. *E. coli* ranked first in urinary tract infections, third overall, and 5$^{th}$ in CLABSI. *P. aeruginosa* ranked second for urinary tract infections, and 7$^{th}$ each overall and for CLABSI. The most relevant pathogen for the instant catheter model is likely *S. aureus* which has been associated with CLABSI for a long time and catheter related urinary tract infections more recently.

The EAA flush was found to be effective at reducing the ATP content of biofilms grown in silicone tubing depending on the strain and concentration of EAA. In general, as the concentration of EAA was reduced, the percent reduction for ATP content and biofilm biomass decreased. However, some strains (e.g. *S. marcescens*) still had a statistically significant reduction in the ATP content of their biofilm at 5 mg/ml of EAA. EAA reduced growth and biofilm biomass of both Gram positive (*S. aureus*) and Gram negative bacteria (all else). Therefore, the addition of EAA to a liquid catheter flush may one day be uses as a broad spectrum prevention against both Gram positive and Gram negative bacteria.

Figure 11A:
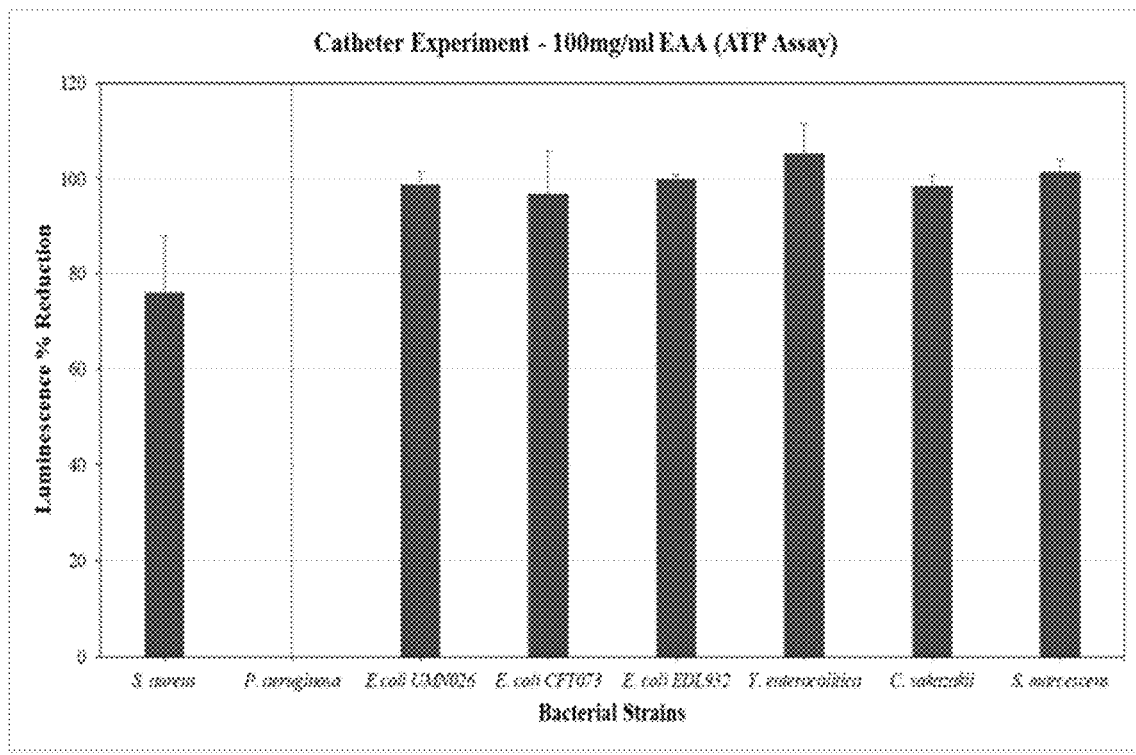
FIGS. 11A-B show graphs illustrating percent reduction of luminescence from the ATP and absorbance from the CV assay when biofilms were treated with 100 mg/ml EAA, compared to untreated biofilms. (A) Shows the percent reductions by 100 mg/ml of EAA in the ATP content of biofilm. (B) Shows the absorbance data of the total biofilm biomass from the CV assay.
Figure 11B:
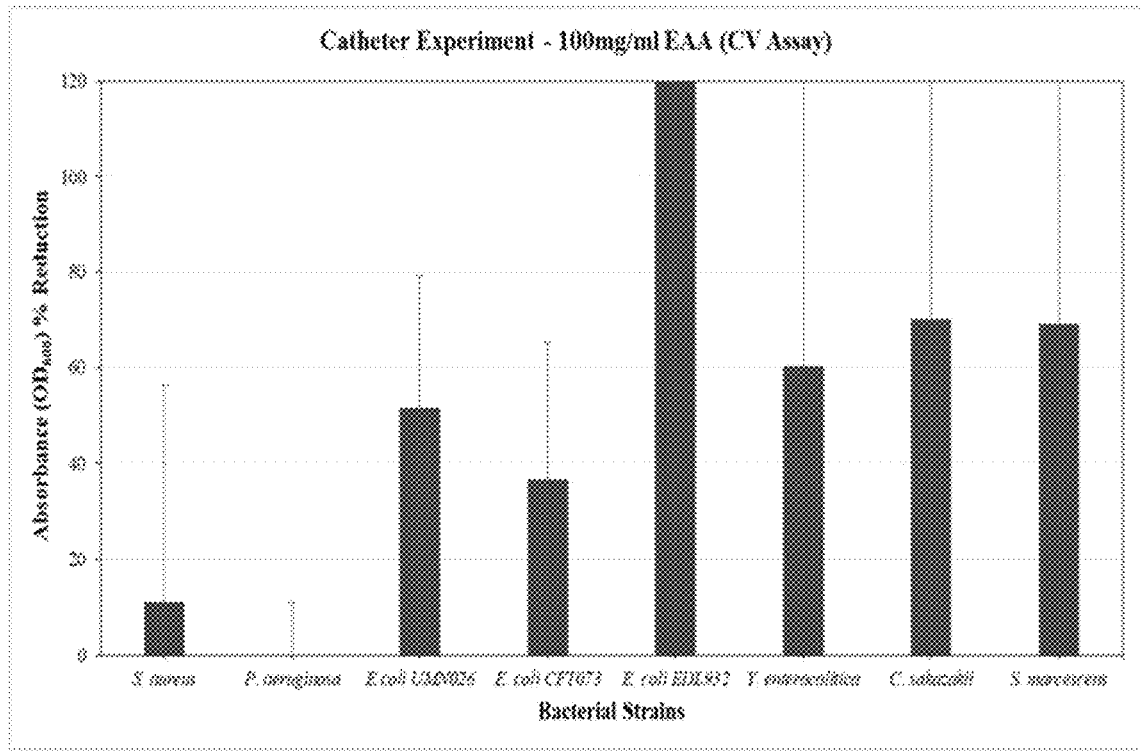

An important observation from this study is that EAA had a greater effect on ATP content of the biofilms than on biofilm biomass. Higher concentrations of EAA (10 and 100 mg/ml) were able to reduce ATP content around 90-99% depending on the strain. However, biofilm biomass reductions were significantly less pronounced. As one specific example, FIGS. 11A-B shows that the ATP content in the biofilm of *S. aureus* was reduced by 76% as a consequence of treatment with 100 mg/ml of EAA. Biofilm biomass quantified with the CV assay was reduced by only 10%.

The CV assay stains all negatively charged surface molecules, including live and dead bacteria, as well as the extrapolymeric matrix. Since the CV assay does not distinguish between live and dead bacteria, the ATP bioluminescence assay was used to quantify the metabolic activity of live cells. This assay relies on the conversion of luciferin and ATP to oxyluciferin and AMP by means of the enzyme luciferase with the concomitant emission of luminescence. In view of the discrepancy between the ATP and CV data, it is believed that EAA may be killing all the viable cells, but leaving behind dead cells and extrapolymeric matrix, both of which are stained and detected with the CF assay. FIGS. 16A-C shows that treatment with 100 mg/ml of EAA caused a statistically significant decrease in *S. aureus* ATP content of the biofilm, a small reduction in biofilm biomass that had no statistical significance, and a 1 log reduction in viable cells. At this point, it is not known whether the reduction in the viable cell counts can serve as the sole explanation for the reduction in the ATP content of the biofilm for this bacterium. However, the data presented herein is in agreement with the hypothesis that EAA reduces the number of viable cells. Therefore, it is recommended that viable cell counts be included in all assessments of the anti-microbial effects of chemicals.

In summary, *S. aureus*, *P. aeruginosa*, two uropathogenic *E. coli*, one enterohemorrhagic *E. coli*, *Y. enterocolitica*, *C. sakazakii*, and *S. marcescens* were grown in the tubings of a Hemodialysis Fistula Set, which were flushed with EAA three times during the 2 week incubation period. Concentrations of EAA of 100, 10, 5, and 1 mg/ml were tested in four experiments. Biofilms were characterized for their ATP content with the ATP assay and their biomass with the crystal violet assay. In an additional experiment, viable cells numbers were determined in biofilms of *S. aureus* and *P. aeruginosa* after treatment with 0 or 100 mg/ml of EAA. Three consecutive flushes of 100 mg/ml of EAA reduced ATP content, biofilm biomass, and viable cell counts of *S. aureus* and *P. aeruginosa*. ATP content and biofilm biomass were reduced for the majority of the other pathogens. The effect of EAA on ATP content and biomass of the biofilms varied with the strain and declined with decreasing concentrations of EAA. Accordingly, this Example shows that EAA may be used as an antibiotic lock therapy for catheters. This may help reduce the use of antibiotics and decrease the emergence of antibiotic resistant bacteria. As an additional benefit, EAA is a homolog to a bacterial nutrient, which may delay the occurrence of resistance towards EAA.

Example 4

This Example demonstrates the development of materials with biofilm inhibiting properties for multiple applications. More specifically, this example focuses on the production of polyurethane-based biomaterials, which are commonly used in clinical and food processing contexts, that contain a precise mixture of chemicals that the bacteria will consider nutrients or 'food' and that will inhibit the formation of bacterial biofilm. By preventing biofilms from forming in the first place, these materials avoid the need and expense of removing biofilms and prevent the economic loss caused by the biofilms between their formation and removal.

Figure 17:
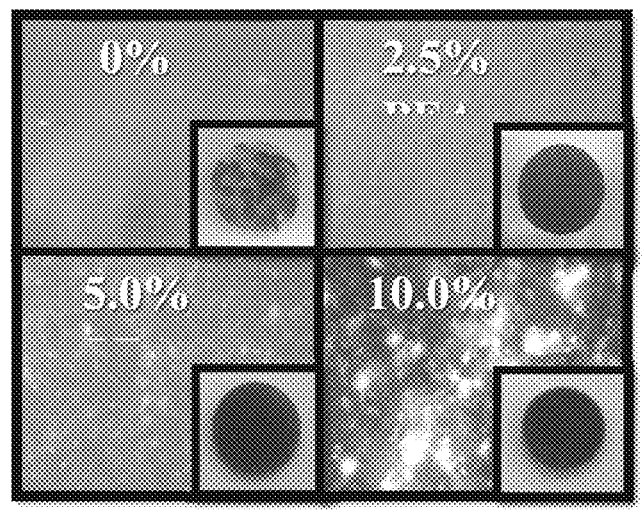
FIG. 17 shows images of polyurethane infused with different concentrations of PEA.

The instant inventors modified a material that is commonly used in clinical and food processing contexts, polyurethane, with β-phenylethylamine (PEA). To produce the PEA containing polyurethane (PU-PEA), food grade polyurethane (Zythane 7085A™) was impregnated with 0, 2.5, 5.0, and 10.0 weight percent PEA and a heat-melt extruded. At 10 wt. %, PEA formed aggregates and was not anymore uniformly distributed throughout the material (FIG. 17). Using a non-pathogenic *E. coli* strain, 5 wt. % PEA exhibited a larger reducing effect on biofilm amounts than 2.5% PEA.

Figure 18:
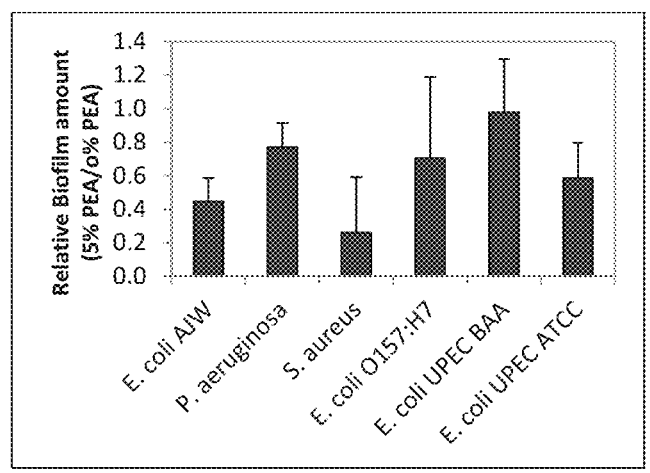
FIG. 18 shows a graph illustrating biofilm reduction by PEA. For each of the six bacterial pathogens, biofilm amounts at 5% PEA were divided by amounts at 0% PEA. As one example, 20% relative biofilm amount by *S. aureus* is equivalent to an 80% reduction of biofilm amounts by 5% PEA.

The biofilm inhibiting efficacy of 5 wt. % PEA was then tested against six bacterial strains (FIG. 18). *E. coli* AJW is non-pathogenic and was described as a good former of biofilm, *P. aeruginosa* is a pathogen that was described as a contaminant on conveyor belts, but also forms biofilm on urinary catheters. *S. aureus* causes staph infections and can form biofilm in intravenous catheters, *E. coli* O157:H7 has been studied in multiple foods and on numerous food processing surfaces, and the two *E. coli* UPEC strains are uropathogens that are commonly found on catheters. PU/PEA had reduced biofilm amounts relative to plain polyurethane for all strains tested. Reductions varied between 5 and 80% in depending on the bacterial pathogen. In particular, this initial PU-PEA material was able to reduce *Staphylococcus aureus* biofilm by 80% and biofilm of several other bacterial pathogens by 20 to 50%.

To determine whether the bacteria were being adversely affected by PEA, a live/dead assay was performed where the total bacterial population and the population of dead bacteria were stained with different fluorescence dyes. Preliminary data indicate that viability of the bacteria was not impacted by PEA. This supports the argument that the bacterial nutrients reduce biofilm amounts without killing the bacteria, therefore, reducing the likelihood of the development of resistance.

Next, one or more of the biofilm inhibiting compounds was added to the polyurethane material above. The biofilm inhibitors that are infused into polyurethane include PEA and up to five other bacterial nutrients. β-phenylethylamine (PEA), acetoacetic acid, L-lyxose, D-mannosamine, D,L-glycerol phosphate, thymine, D,L-α-aminocaprylic acid, and D-asparagine have been determined to inhibit bacterial cell counts and biofilm amounts when *E. coli* O157:H7 was grown in liquid beef broth at 10° C. Additional experiments were done with the non-pathogenic *E. coli* K-12 strain in a standard laboratory bacterial growth medium, designated TB. In these experiments, D-xylose and α-keto-butyric acid were identified as inhibitors of growth and biofilm amounts. A summary of six possible nutrients is shown in TABLE 9 below. Note that most of the nutrients were active in either one or the other of the two experiments that were performed under much different conditions (e.g. temperature, growth medium).

TABLE 9

Summary of inhibitory effects of six supplements and their biological and toxic properties

|  | PEA | D-asparagine | L-lyxose | D-xylose | α-keto-butyric acid | D,L-α-aminocaprylic acid |
|---|---|---|---|---|---|---|
| *E. coli* O157: H7, beef broth, 10° C. | | | | | | |
| $IC_{50}$ biofilm | 0.34 mg/ml | 0.2 mg/ml | 76 mg/ml | ND | ND | 1.84 mg/ml |
| $IC_{50}$ cell number | 0.32 mg/ml | 0.62 mg/ml | 72 mg/ml | ND | ND | 1.96 mg/ml |
| *E. coli* K-12, TB, 25° C. | | | | | | |
| Ratio, biofilm (supplement/control) | 1.1 | 1.07 | 0.71 | 0.59 | 0.62 | 0.85 |
| Ratio, flhD (supplement/control) | 1.3 | 1.2 | 0.68 | 0.56 | 0.57 | 0.55 |
| Ratio, growth (supplement/control) | 0.81 | 0.9 | 0.98 | 0.91 | 0.54 | 0.26 |
| Impact on humans | Neurotransmitter, similar to dopamine | Not investigated | Not degraded in humans | Needs to be obtained from diet | To propionyl-CoA | No hazard to humans (MSDS) |

A cost/benefit analysis was then conducted. L-Lyxose, D-Mannosamine, and D,L-α-aminocaprylic acid are not very feasible because of high cost/g. L-lyxose also has a very high $IC_{50}$. Likewise, D-Asparagine is ten times as expensive when compared to PEA, though it is also active at a low concentration. Thymine is twice as expensive as PEA and requires five times the amount. D-xylose is half the cost of PEA and but did not currently have an $IC_{50}$ value. D,L-α-glycero phosphate is twice as expensive as PEA and also did not have an $IC_{50}$. Accordingly, the instant inventors initially focused on D-asparagine because of the high activity, and D-xylose and D,L-α-glycerophosphate because of low cost.

One valuable aspect of the biofilm inhibitors discussed above, is that the bacteria consider them a 'food' source. Conventional anti-microbial agents are targeted at killing the bacteria, which puts selective pressure on the bacteria and leads to the emergence of antibiotic-resistant bacterial strains. However, it is believed that such resistance will be reduced or eliminated with the instant biomaterials since they do not attempt to kill the bacteria. Instead, the instant biomaterials modify or manipulate the regulatory networks of the bacteria to coax them into behaviors that will be less harmful to humans (i.e., lack of an ability to form biofilm).

Figure 19:
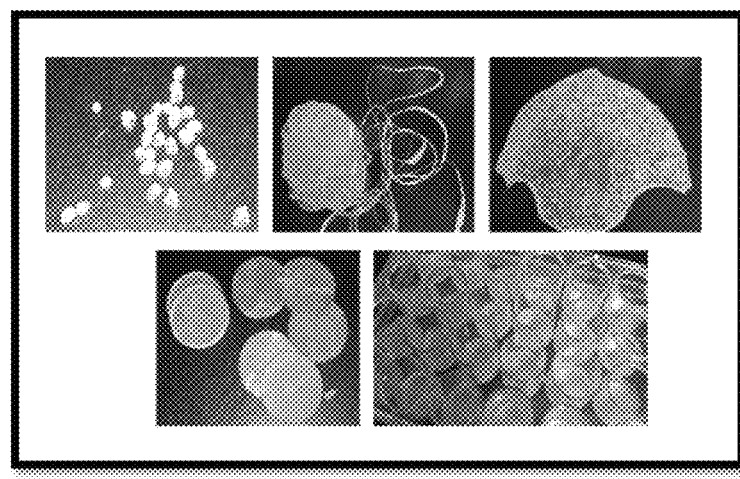
FIG. 19 shows images of PEA infused polyurethane formed through heat extrusion. The images are in order: food grade polyurethane beads, extrusion product, flat sheets, rubber pennies, 24 well plates.

To produce combination materials including the one or more biofilm inhibiting compounds (FIG. 19), the extruder (Thermo-Haake Polylab OS) will be heated to 210° C., the polyurethane beads (top row, left panel) will be fed until the system is purged and the desired mass flow is achieved. The feeding of the bacterial nutrient will cause a reduction of the melting point of the polyurethane. Therefore, temperature can be reduced to 190° C., which will minimize thermal degradation of the material. After 20 minutes of steady state feeding, collection of the molten extrusion product (top row, middle panel) will take place in small pans at 1 minute intervals directly from the outlet of the hot extruder. The panned samples are then hot pressed to yield a uniform, flat composite sheet (top row, right panel) for testing and punching out rubber pennies (bottom row, left panel) that fit into the 24 well plates (bottom row, right panel).

The combination material formed from the addition of the biofilm inhibiting compounds to the PU-PEA materials is believed to increase the inhibitory effect and expanded the range of bacterial pathogens against which the material is effective. The target biofilm reduction for food processing applications is 80% for all food pathogens to be tested under this example. For catheters, a 50% reduction in biofilm formation is believed to be clinically relevant, as the human host still has the aid of his/her immune system to help clear the underlying infection. The PU-PEA material alone has achieved an 80% biofilm reduction for *S. aureus*. A reduction of 50% reduction was attained for the non-pathogenic *E. coli* strain. By incorporating additional nutrients identified as biofilm inhibitors into PU-PEA it is possible to achieve higher, broad-spectrum reductions.

Using the rubber pennies in the 24-well plates, the anti-biofilm effectiveness of the new combination materials can be compared with pure polyurethane and PU-PEA. Effectiveness of the nutrient additive can be tested with the ATP assay that measures live bacteria and the crystal violet assay that stains live and dead biomass. The experiments can be performed with a range of clinical and food pathogens. The list of pathogens includes the six from FIG. 18, supplemented by various clinical and food pathogens, such as *E. coli* O157:H7, *S. enterica*, and *L. monocytogenes*. Clinically relevant bacteria include the two uropathenic *E. coli*, *C. sakazakii*, *S. marcescens*, and *Y. enterocolitica*. Bacterial pathogens such as *P. aeruginosa* and *S. aureus* are relevant in both the food and the clinical context. Percent reduction in biofilm amount for each modified biomaterial can be calculated by 1) dividing the average CV (or ATP) value for each combination material by the average CV (or ATP) value of plain polyurethane and PU/PEA, 2) multiplying this ratio by 100, and 3) subtracting the resulting product from 100.

All publications, patents, and patent applications mentioned in this specification are herein incorporated by reference to the same extent as if each individual publication, patent, or patent application was specifically and individually indicated to be incorporated by reference, including the references set forth in the following list:

REFERENCES (1) Al-Nabulsi, A. A., Osaili, T. M., Elabedeen, N. A., Jaradat, Z. W., Shaker, R. R., Kheirallah, K. A., Tarazi, Y. H. and Holley, R. A. (2011) Impact of environmental stress desiccation, acidity, alkalinity, heat or cold on antibiotic susceptibility of *Cronobacter sakazakii*. *Int J Food Microbiol* 146, 137-143.

(2) Badger, J. L., Young, B. M., Darwin, A. J. and Miller, V. L. (2000) *Yersinia enterocolitica* ClpB affects levels of invasin and motility. *J Bacteriol* 182, 5563-5571.

(3) Bleves, S., Marenne, M. N., Detry, G. and Cornelis, G. R. (2002) Up-regulation of the *Yersinia enterocolitica* yop regulon by deletion of the flagellum master operon flhDC. *J Bacteriol* 184, 3214-3223.

(4) Bradford, W. D., Noce, P. S. and Gutman, L. T. (1974) Pathologic features of enteric infection with *Yersinia enterocolitica*. *Arch Pathol* 98, 17-22.

(5) Breeuwer, P., Lardeau, A., Peterz, M. and Joosten, H. M. (2003) Desiccation and heat tolerance of *Enterobacter sakazakii*. *J Appl Microbiol* 95, 967-973.

(6) Brzostek, K., Skorek, K. and Raczkowska, A. (2012) OmpR, a central integrator of several cellular responses in *Yersinia enterocolitica*. *Adv Exp Med Biol* 954, 325-334.

(7) Butler, J. F., Garcia-Maruniak, A., Meek, F. and Maruniak, J. E. (2010) Wild Florida house flies (*Musca domestica*) as carriers of pathogenic bacteria. *Florida Entomologist* 93, 218-223.

(8) Carniel, E., Mazigh, D. and Mollaret, H. H. (1987) Expression of iron-regulated proteins in *Yersinia* species and their relation to virulence. *Infect Immun* 55, 277-280.

(9) Carter, P. B. (1975) Pathogenecity of *Yersinia enterocolitica* for mice. *Infect Immun* 11, 164-170.

(10) Chen, C. Y., Hogarth, L. A. and Shanley, M. S. (1991) Regulatory sequences controlling short chain fatty acid metabolism in *Escherichia coli*. *SAAS bulletin, biochemistry and biotechnology* 4, 22-26.

(11) Chuang, S. E., Daniels, D. L. and Blattner, F. R. (1993) Global regulation of gene expression in *Escherichia coli*. *J Bacteriol* 175, 2026-2036.

(12) Cornelis, G. R. (2002) The *Yersinia* Ysc-Yop virulence apparatus. *Int J Med Microbiol* 291, 455-462.

(13) Cornelis, G. R., Sluiters, C., Delor, I., Geib, D., Kaniga, K., Lambert de Rouvroit, C., Sory, M. P., Vanooteghem, J. C. and Michiels, T. (1991) ymoA, a *Yersinia enterocolitica* chromosomal gene modulating the expression of virulence functions. *Mol Microbiol* 5, 1023-1034.

(14) Dhar, M. S. and Virdi, J. S. (2014) Strategies used by *Yersinia enterocolitica* to evade killing by the host: thinking beyond Yops. *Microbes and infection* 16, 87-95.

(15) Farmer, J. J., 3rd (2015) My 40-year history with *Cronobacter/Enterobacter sakazakii*—lessons learned, myths debunked, and recommendations. *Frontiers in pediatrics* 3, 84.

(16) Friedemann, M. (2007) *Enterobacter sakazakii* in food and beverages (other than infant formula and milk powder). *Int J Food Microbiol* 116, 1-10.

(17) Gottschalk, P. G. and Dunn, J. R. (2005) The five-parameter logistic: a characterization and comparison with the four-parameter logistic. *Anal Biochem* 343, 54-65.

(18) Gupta, V., Gulati, P., Bhagat, N., Dhar, M. S. and Virdi, J. S. (2015) Detection of *Yersinia enterocolitica* in food: an overview. *European journal of clinical microbiology & infectious diseases: official publication of the European Society of Clinical Microbiology* 34, 641-650.

(19) Ham, Y. and Kim, T. J. (2016) Inhibitory activity of monoacylglycerols on biofilm formation in *Aeromonas hydrophila, Streptococcus mutans, Xanthomonas oryzae*, and *Yersinia enterocolitica*. *SpringerPlus* 5, 1526.

(20) Himelright, I. (2002) *Enterobacteri sakazakii* infections associated with the use of powdered infant formula—Tennessee 2001. *Morb Mortal Wkly Rep* 51, 298-300.

(21) Hinchliffe, S. J., Howard, S. L., Huang, Y. H., Clarke, D. J. and Wren, B. W. (2008) The importance of the Rcs phosphorelay in the survival and pathogenesis of the enteropathogenic *Yersiniae*. *Microbiology* 154, 1117-1131.

(22) Horne, S. M. and Prüß, B. M. (2006) Global gene regulation in *Yersinia enterocolitica*: effect of FliA on the expression levels of flagellar and plasmid-encoded virulence genes. *Arch Microbiol* 185, 115-126.

(23) Hurrell, E., Kucerova, E., Loughlin, M., Caubilla-Barron, J., Hilton, A., Armstrong, R., Smith, C., Grant, J., Shoo, S. and Forsythe, S. (2009) Neonatal enteral feeding tubes as loci for colonisation by members of the Enterobacteriaceae. *BMC infectious diseases* 9, 146.

(24) Ioannidis, A., Kyratsa, A., Ioannidou, V., Bersimis, S. and Chatzipanagiotou, S. (2014) Detection of biofilm production of *Yersinia enterocolitica* strains isolated from infected children and comparative antimicrobial susceptibility of biofilm versus planktonic forms. *Molecular diagnosis & therapy* 18, 309-314.

(25) Iversen, C., Lane, M. and Forsythe, S. J. (2004) The growth profile, thermotolerance and biofilm formation of *Enterobacter sakazakii* grown in infant formula milk. *Lett Appl Microbiol* 38, 378-382.

(26) Kalyantanda, G., Shumyak, L. and Archibald, L. K. (2015) *Cronobacter* species contamination of powdered infant formula and the implications for neonatal health. *Frontiers in pediatrics* 3, 56.

(27) Kandhai, M. C., Reij, M. W., Gorris, L. G., Guillaume-Gentil, O. and van Schothorst, M. (2004) Occurrence of *Enterobacter sakazakii* in food production environments and households. *Lancet* 363, 39-40.

(28) Kapatral, V., Campbell, J. W., Minnich, S. A., Thomson, N. R., Matsumura, P. and Prüß, B. M. (2004) Gene array analysis of *Yersinia enterocolitica* FlhD and FlhC: regulation of enzymes affecting synthesis and degradation of carbamoylphosphate. *Microbiology* 150, 2289-2300.

(29) Lambert de Rouvroit, C., Sluiters, C. and Cornelis, G. R. (1992) Role of the transcriptional activator, VirF, and temperature in the expression of the pYV plasmid genes of *Yersinia enterocolitica*. *Mol Microbiol* 6, 395-409.

(30) Larson, E. L., Cimiotti, J. P., Haas, J., Nesin, M., Allen, A., Della-Latta, P. and Saiman, L. (2005) Gram-negative bacilli associated with catheter-associated and non-catheter-associated bloodstream infections and hand carriage by healthcare workers in neonatal intensive care units. *Pediatric critical care medicine: a journal of the Society of Critical Care Medicine and the World Federation of Pediatric Intensive and Critical Care Societies* 6, 457-461.

(31) Lynnes, T., Horne, S. M. and Prüß, B. M. (2014) β-Phenylethylamine as a novel nutrient treatment to reduce bacterial contamination due to *Escherichia coli* O157:H7 on beef meat. *Meat Sci* 96, 165-171.

(32) Mahlen, S. D. (2011) *Serratia* infections: from military experiments to current practice. *Clinical microbiology reviews* 24, 755-791.

(33) McNally, A., La Ragione, R. M., Best, A., Manning, G. and Newell, D. G. (2007) An aflagellate mutant *Yersinia enterocolitica* biotype 1A strain displays altered invasion of epithelial cells, persistence in macrophages, and cytokine secretion profiles in vitro. *Microbiology* 153, 1339-1349.

(34) McNally, A., Thomson, N. R., Reuter, S. and Wren, B. W. (2016) 'Add, stir and reduce': *Yersinia* spp. as model bacteria for pathogen evolution. *Nat Rev Microbiol* 14, 177-190.

(35) Molla, A., Kagimoto, T. and Maeda, H. (1988) Cleavage of immunoglobulin G (IgG) and IgA around the hinge region by proteases from *Serratia marcescens*. *Infect Immun* 56, 916-920.

(36) O'Toole, G. A., Pratt, L. A., Watnick, P. I., Newman, D. K., Weaver, V. B. and Kolter, R. (1999) Genetic approaches to study of biofilms. *Methods Enzymol* 310, 91-109.

(37) Pepe, J. C. and Miller, V. L. (1993) *Yersinia enterocolitica* invasin: a primary role in the initiation of infection. *Proc Natl Acad Sci USA* 90, 6473-6477.

(38) Pepe, J. C., Wachtel, M. R., Wagar, E. and Miller, V. L. (1995) Pathogenesis of defined invasion mutants of *Yersinia enterocolitica* in a BALB/c mouse model of infection. *Infect Immun* 63, 4837-4848.

(39) Pfaffl, M. W. (2001) A new mathematical model for relative quantification in real-time RT-PCR. *Nucleic Acids Res* 29, e45.

(40) Portnoy, D. A. and Falkow, S. (1981) Virulence-associated plasmids from *Yersinia enterocolitica* and *Yersinia pestis*. *J Bacteriol* 148, 877-883.

(41) Portnoy, D. A., Moseley, S. L. and Falkow, S. (1981) Characterization of plasmids and plasmid-associated determinants of *Yersinia enterocolitica* pathogenesis. *Infect Immun* 31, 775-782.

(42) Potezny, N., Atkinson, E. R., Rofe, A. M. and Conyers, R. A. (1981) The inhibition of bacterial cell growth by ketone bodies. *The Australian journal of experimental biology and medical science* 59, 639-649.

(43) Rana, K., Thaper, D. and Prabha, V. (2017) Is there a role for *Serratia marcescens* in male infertility: An experimental study? *Microbial pathogenesis* 105, 13-18.

(44) Ray, C., Shenoy, A. T., Orihuela, C. J. and Gonzalez-Juarbe, N. (2017) Killing of *Serratia marcescens* biofilms with chloramphenicol. *Annals of clinical microbiology and antimicrobials* 16, 19.

(45) Ruckdeschel, K., Deuretzbacher, A. and Haase, R. (2008) Crosstalk of signalling processes of innate immunity with *Yersinia* Yop effector functions. *Immunobiology* 213, 261-269.

(46) Sauer, K., Camper, A. K., Ehrlich, G. D., Costerton, J. W. and Davies, D. G. (2002) *Pseudomonas aeruginosa* displays multiple phenotypes during development as a biofilm. *J Bacteriol* 184, 1140-1154.

(47) Schmid, M., Iversen, C., Gontia, I., Stephan, R., Hofmann, A., Hartmann, A., Jha, B., Eberl, L., Riedel, K. and Lehner, A. (2009) Evidence for a plant-associated natural habitat for *Cronobacter* spp. *Res Microbiol* 160, 608-614.

(48) Schneider, D. A. and Gourse, R. L. (2004) Relationship between growth rate and ATP concentration in *Escherichia coli*: a bioassay for available cellular ATP. *J Biol Chem* 279, 8262-8268.

(49) Skurnik, M. and Toivanen, P. (1992) LcrF is the temperature-regulated activator of the yadA gene of *Yersinia enterocolitica* and *Yersinia pseudotuberculosis*. *J Bacteriol* 174, 2047-2051.

(50) Theodorou, M. C., Theodorou, E. C. and Kyriakidis, D. A. (2012) Involvement of AtoSC two-component system in *Escherichia coli* flagellar regulon. *Amino Acids* 43, 833-844.

(51) Viboud, G. I. and Bliska, J. B. (2005) *Yersinia* outer proteins: role in modulation of host cell signaling responses and pathogenesis. *Annu Rev Microbiol* 59, 69-89.

(52) Young, G. M., Badger, J. L. and Miller, V. L. (2000) Motility is required to initiate host cell invasion by *Yersinia enterocolitica*. *Infect Immun* 68, 4323-4326.

(53) Young, G. M., Smith, M. J., Minnich, S. A. and Miller, V. L. (1999) The *Yersinia enterocolitica* motility master regulatory operon, flhDC, is required for flagellin production, swimming motility, and swarming motility. *J Bacteriol* 181, 2823-2833.

(54) Zhou, K., Zhou, L., Lim, Q., Zou, R., Stephanopoulos, G. and Too, H. P. (2011) Novel reference genes for quantifying transcriptional responses of *Escherichia coli* to protein overexpression by quantitative PCR. *BMC Mol Biol* 12, 18.

(55) Amrutha, B., Sundar, K., & Shetty, P. H. (2017). Effect of organic acids on biofilm formation and quorum signaling of pathogens from fresh fruits and vegetables. *Microb Pathog*, 111, 156-162.

(56) Brashears, M. M., & Chaves, B. D. (2017). The diversity of beef safety: A global reason to strengthen our current systems. *Meat Science*, 132, 59-71.

(57) Cook, W. M., Purchase, R., Ford, G. P., Creasy, D. M., Brantom, P. G., & Gangolli, S. D. (1992). A 28-day feeding study with ethyl acetoacetate in rats. *Food Chem Toxicol*, 30(7), 567-573.

(58) Gardner, G. A. (1966). A selective medium for the enumeration of *Microbacterium thermosphactum* in meat and meat products. *Journal of Applied Bacteriology*, 29(3), 455-460.

(59) Gautheron, P., Giroux, J., Cottin, M., Audegond, L., Morilla, A., Mayordomo-Blanco, L., . . . Spielmann, H. (1994). Interlaboratory assessment of the bovine corneal opacity and permeability (BCOP) assay. *Toxicol In Vitro*, 8(3), 381-392.

(60) Gill, A., & Huszczynski, G. (2016). Enumeration of *Escherichia coli* O157:H7 in outbreak-associated beef patties. *J Food Prot*, 79(7), 1266-1268. doi:10.4315/0362-028X.JFP-15-521

(61) Gill, C. O. (1976). Substrate limitation of bacterial growth at meat surfaces. *Journal of Applied Bacteriology*, 41(3), 401-410.

(62) Hoechst A G, P. T. (1983). Acetessigsaureethylester-Prufung auf akute dermale Reizwirkung/Atzwirkung am Kaninchen. *Unpublished report No.* 83.0409.

(63) Holzapfel, W. H. (1998). The Gram-positive bacteria associated with meat and meat products. In R. G. D. Board, A. R. (Ed.), *The microbiology of meat and poultry*. London, United Kingdom: Blackie Academic and Professional.

(64) Home, S. M., Schroeder, M., Murphy, J., & Prüβ, B. M. (2018). Acetoacetate and ethyl acetoacetate as novel inhibitors of bacterial biofilm. *Lett. Appl. Microbiol.*, 66, 329-339.

(65) Hoyle Parks, A. R., Brashears, M. M., Woerner, W. D., Martin, J. N., Thompson, L. D., & Brooks, J. C. (2012). Spoilage characteristics of traditionally packaged ground beef with added lactic acid bacteria displayed at abusive temperatures. *Journal Animal Sciences*, 90, 642-648.

(66) Ishidate, M., Jr., Sofuni, T., Yoshikawa, K., Hayashi, M., Nohmi, T., Sawada, M., & Matsuoka, A. (1984).

(67) Primary mutagenicity screening of food additives currently used in Japan. *Food Chem Toxicol,* 22(8), 623-636.
(67) Jackson, L. S. (2009). Chemical food safety issues in the United States: past, present, and future. *Journal Agricultural and Food Chemistry,* 57(18), 8161-8170.
(68) Koutsoumanis, K., Stamatiou, A., Skandamis, P., & Nychas, G. J. (2006). Development of a microbial model for the combined effect of temperature and pH on spoilage of ground meat, and validation of the model under dynamic temperature conditions. *Applied and Environmental Microbiology,* 72(1), 124-134.
(69) Li, Q., & Logue, C. M. (2005). The growth and survival of *Escherichia coli* O157:H7 on minced bison and pieces of bison meat stored at 5 and 10° C. *Food Microbiology,* 22, 415-421.
(70) Lynnes, T., Home, S. M., & Prüβ, B. M. (2014). β-Phenylethylamine as a novel nutrient treatment to reduce bacterial contamination due to *Escherichia coli* O157:H7 on beef meat. *Meat Science,* 96(1), 165-171.
(71) Marques, L. R., Moore, M. A., Wells, J. G., Wachsmuth, I. K., & O'Brien, A. D. (1986). Production of shiga-like toxin by *Escherichia coli. J. Infect. Dis.,* 154(2), 338-341.
(72) Mead, G. C., & Adams, B. W. (1977). A selective medium for the rapid isolation of *pseudomonads* associated with poultry meat spoilage. *British Poultry Science,* 18(6), 661-670.
(73) Mossel, D. A., Mengerink, W. H., & Scholts, H. H. (1962). Use of a modified MacConkey agar medium for the selective growth and enumeration of Enterobacteriaceae. *Journal of Bacteriology,* 84, 381.
(74) Nychas, G. J., Dillon, V. M., & Board, R. G. (1988). Glucose, the key substrate in the microbiological changes occurring in meat and certain meat products. *Biotechnology and Applied Biochemistry,* 10(3), 203-231.
(75) Oda, Y. H., Y.; Inoue, K.; Yamamoto, H.; Niihara, T.; Kunita, N. (1978). Mutagenicity of food flavours in bacteria (1 st report). *Osaka-Fu Koshu Eisei Hokoku, Shokuhin Eisei Hen,* 9, 177-181.
(76) Parks, A. R., Brashears, M. M., Woerner, W. D., Martin, J. N., Thompson, L. D., & Brooks, J. C. (2012). Spoilage characteristics of ground beef with added lactic acid bacteria and rosemary oleoresin packaged in a modified-atmosphere package and displayed at abusive temperatures. *Journal of Animal Sciences,* 90(6), 2054-2060.
(77) Radha krishnan, K., Babuskin, S., Azhagu Saravana Babu, P., Sasikala, M., Sabina, K., Archana, G., . . . Sukumar, M. (2014). Antimicrobial and antioxidant effects of spice extracts on the shelf life extension of raw chicken meat. *Int J Food Microbiol,* 171, 32-40. doi: 10.1016/j.ijfoodmicro.2013.11.011
(78) Reid, R., Fanning, S., Whyte, P., Kerry, J., & Bolton, D. (2017). Comparison of hot versus cold boning of beef carcasses on bacterial growth and the risk of blown pack spoilage. *Meat Sci,* 125, 46-52. doi: 10.1016/j.meatsci.2016.11.012
(79) Remenant, B., Jaffres, E., Dousset, X., Pilet, M. F., & Zagorec, M. (2015). Bacterial spoilers of food: behavior, fitness and functional properties. *Food Microbiology,* 45, 45-53.
(80) Rogers, H. B., Brooks, J. C., Martin, J. N., Tittor, A., Miller, M. F., & Brashears, M. M. (2014). The impact of packaging system and temperature abuse on the shelf life characteristics of ground beef. *Meat Sci,* 97(1), 1-10.
(81) Seys, S. A., Sampedro, F., & Hedberg, C. W. (2016). Factors associated with recovery of meat products following recalls due to Shiga toxin-producing *Escherichia coli. Epidemiol Infect,* 144(14), 2940-2947. doi:10.1017/S0950268816001266
(82) Stanbridge, L. H. D., A. R. (1998). The microbiology of chill-stored meat. In R. G. D. Board, A. R. (Ed.), *The microbiology of meat and poultry.* London, United Kingdom: Blackie Academic and Professional.
(83) Sule, P., Home, S. M., Logue, C. M., & Prüβ, B. M. (2011). Regulation of cell division, biofilm formation, and virulence by FlhC in *Escherichia coli* O157:H7 grown on meat. *Applied and Environmental Microbiology,* 77(11), 3653-3662.
(84) Tamminen, L. M., Fransson, H., Traven, M., Aspan, A., Alenius, S., Emanuelson, U., . . . Eriksson, E. (2018). Effect of on-farm interventions in the aftermath of an outbreak of hypervirulent verocytotoxin-producing *Escherichia coli* O157:H7 in Sweden. *Vet Rec,* 182(18), 516. doi:10.1136/vr.104223
(85) Taormina, P. J., & Beuchat, L. R. (1999). Comparison of chemical treatments to eliminate enterohemorrhagic *Escherichia coli* O157:H7 on alfalfa seeds. *Journal of Food Protection,* 62(4), 318-324.
(86) Torso, L. M., Voorhees, R. E., Forest, S. A., Gordon, A. Z., Silvestri, S. A., Kissler, B., . . . Harrison, L. H. (2015). *Escherichia coli* O157:H7 outbreak associated with restaurant beef grinding. *J Food Prot,* 78(7), 1272-1279. doi:10.4315/0362-028X.JFP-14-545
(87) Vangay, P., Fugett, E. B., Sun, Q., & Wiedmann, M. (2013). Food microbe tracker: a web-based tool for storage and comparison of food-associated microbes. *Journal of Food Protection,* 76(2), 283-294. doi: 10.
(88) Wameadesa, N., Sae-lim, A., Hayeebilan, F., Rattanachuay, P., & Sukhumungoon, P. (2017). Enteroaggregative *Escherichia coli* 0104 from thai and imported Malaysian raw beef. *Southeast Asian J Trop Med Public Health,* 48(2), 338-350.
(89) White, A., Cronquist, A., Bedrick, E. J., & Scallan, E. (2016). Food source prediction of shiga toxin-producing *Escherichia coli* outbreaks using demographic and outbreak characteristics, United States, 1998-2014. *Foodborne Pathog Dis,* 13(10), 527-534. doi: 10.1089/fpd.2016.2140
(90) Yoo, Y. S. (1986). Mutagenic and antimutagenic activities of flavoring agents used in foodstuffs. *J Osaka City Med Cent,* 34, 267-288
(91) Lynnes T, Horne S M, Prüβ B M: β-Phenylethylamine as a novel nutrient treatment to reduce bacterial contamination due to *Escherichia coli* O157:H7 on beef meat. Meat Science 2014, 96(1):165-171.
(92) Horne S M, Schroeder M, Murphy J, Prüβ B M: Acetoacetate and ethyl acetoacetate as novel inhibitors of bacterial biofilm. Lett Appl Microbiol 2018, 66:329-339.
(93) Mermel L A, Allon M, Bouza E, Craven D E, Flynn P, O'Grady N P, Raad, II, Rijnders B J, Sherertz R J, Warren D K: Clinical practice guidelines for the diagnosis and management of intravascular catheter-related infection: 2009 Update by the Infectious Diseases Society of America. Clin Infect Dis 2009, 49(1):1-45.
(94) Luppens S B, Reij M W, van der Heij den R W, Rombouts F M, Abee T: Development of a standard test to assess the resistance of *Staphylococcus aureus* biofilm cells to disinfectants. Applied and environmental microbiology 2002, 68(9):4194-4200.
(95) Spoering A L, Lewis K: Biofilms and planktonic cells of *Pseudomonas aeruginosa* have similar resistance to killing by antimicrobials. J Bacteriol 2001, 183(23):6746-6751.

(96) Stewart P S, Rayner J, Roe F, Rees W M: Biofilm penetration and disinfection efficacy of alkaline hypochlorite and chlorosulfamates. J Appl Microbiol 2001, 91(3):525-532.
(97) LeMaster C H, Schuur J D, Pandya D, Pallin D J, Silvia J, Yokoe D, Agrawal A, Hou P C: Infection and natural history of emergency department-placed central venous catheters. Ann Emerg Med 2010, 56(5):492-497.
(98) Tarai B D P, and Kumar D: Recurrent Challenges for Clinicians: Emergence of Methicillin-Resistant *Staphylococcus aureus*, Vancomycin Resistance, and Current Treatment Options. Journal of Laboratory Physicians 2013, 5(2): 71-78.
(99) Casey A L M L, Nightingale P, Elliott T S: Antimicrobial central venous catheters in adults: a systematic review and meta-analysis. The Lancet Infectious Diseases 2008, 8(12):763-776.
(100) Choi Y J, Lim J K, Park J J, Huh H, Kim D J, Gong C H, Yoon S Z: Chlorhexidine and silver sulfadiazine coating on central venous catheters is not sufficient for protection against catheter-related infection: Simulation-based laboratory research with clinical validation. The Journal of international medical research 2017, 45(3): 1042-1053.
(101) Chen Y-M, Dai A-P, Shi Y, Liu Z-J, Gong M-F, Yin X-B: Effectiveness of silver-impregnated central venous catheters for preventing catheter-related blood stream infections: a meta-analysis. International Journal of Infectious Diseases 2014, 29:279-286.
(102) Knetsch MLWaK, L. H.: New Strategies in the Development of Antimicrobial Coatings: The Example of Increasing Usage of Silver and Silver Nanoparticles. Polymers 2011, 3(1):340-366.
(103) Palza H: Antimicrobial Polymers with Metal Nanoparticles. International Journal of Molecular Science 2015, 16:2099-2116.
(104) Ballo M K, Rtimi S, Pulgarin C, Hopf N, Berthet A, Kiwi J, Moreillon P, Entenza J M, Bizzini A: In vitro and in vivo effectiveness of an innovative silver-copper nanoparticle coating of catheters to prevent methicillin-resistant *Staphylococcus aureus* Infection. Antimicrob Agents Chemother 2016, 60(9):5349-5356.
(105) Graves J L, Jr., Tajkarimi M, Cunningham Q, Campbell A, Nonga H, Harrison S H, Barrick J E: Rapid evolution of silver nanoparticle resistance in *Escherichia coli*. Front Genet 2015, 6:42.
(106) Mühling M, Bradford A, Readman J W, Somerfield P J, Handy R D: An investigation into the effects of silver nanoparticles on antibiotic resistance of naturally occurring bacteria in an estuarine sediment. Marine Environmental Research 2009, 68(5):278-283.
(107) Silver S, Phung, L. T. & Silver, G.: Silver as biocides in burn and wound dressings and bacterial resistance to silver compounds. Journal of Industrial Microbiology & Biotechnology 2006, 33(627).
(108) Jena P. M S, Mallick R., Jacob B., Sonawane A: Toxicity and antibacterial assessment of chitosan-coated silver nanoparticles on human pathogens and macrophage cells. International Journal of Nanomedicine 2012, 7:1805-1818.
(109) Stevens K. N. C-B O, van den Bosch E. E., Dias A. A., Knetsch M. L., Aldenhoff Y. B., van der Veen F. H., Maessen J. G., Stobberingh E. E., Koole L. H.: The relationship between the antimicrobial effect of catheter coatings containing silver nanoparticles and the coagulation of contacting blood. Biomaterials 2009, 30:3682-3690.
(110) Norris L B, Kablaoui F, Brilhart M K, Bookstaver P B: Systematic review of antimicrobial lock therapy for prevention of central-line-associated bloodstream infections in adult and pediatric cancer patients. International Journal of Antimicrobial Agents 2017, 50(3):308-317.
(111) Lynnes T H S, and Prüß M: ß-phenylethylamine as a novel nutrient treatment to reduce bacterial contamination due to *Escherichia coli* O157:H7 on beef meat. Meat Science 2014, 96(1):165-171.
(112) Marques L R, Moore M A, Wells J G, Wachsmuth I K, O'Brien A D: Production of Shiga-like toxin by *Escherichia coli*. The Journal of infectious diseases 1986, 154 (2):338-341.
(113) Manges A R, J. R. Johnson, B. Foxman, T. T. O'Bryan, K. E. Fullerton, & L. W. Riley: Widespread distribution of urinary tract infections caused by a multidrug-resistant *Escherichia coli* clonal group. New England Journal of Medicine 2001, 345:1007-1013.
(114) Mobley H L, D. M. Green, A. L. Trifillis, D. E. Johnson, G. R. Chippendale, C. V. Lockatell, B. D. Jones, and J. W. Warren: Pyelonephritogenic *Escherichia coli* and killing of cultured human renal proximal tubular epithelial cells: role of hemolysin in some strains. Infection and Immunity 1990, 58:1281-1289.
(115) Lake J G, Weiner L M, Milstone A M, Saiman L, Magill S S, See I: Pathogen distribution and antimicrobial resistance among pediatric healthcare-associated infections reported to the national healthcare safety network, 2011-2014. Infect Control Hosp Epidemiol 2018, 39(1): 1-11.
(116) Corkum K S, Jones R E, Reuter C H, Kociolek L K, Morgan E, Lautz T B: Central venous catheter salvage in children with *Staphylococcus aureus* central line-associated bloodstream infection. Pediatr Surg Int 2017, 33(11): 1201-1207.
(117) Moon H M, Kim S, Yun K W, Kim H Y, Jung S E, Choi E H, Lee H J: Clinical characteristics and risk factors of long-term central venous catheter-associated bloodstream infections in children. Pediatr Infect Dis J 2017.
(118) Looney A T, Redmond E J, Davey N M, Daly P J, Troy C, Carey B F, Cullen I M: Methicillin-resistant *Staphylococcus aureus* as a uropathogen in an Irish setting. Medicine (Baltimore) 2017, 96(14):e4635.
(119) Li X, Yan Z, Xu J: Quantitative variation of biofilms among strains in natural populations of *Candida albicans*. Microbiology 2003, 149(Pt 2):353-362.
(120) Pruss B M, Verma K, Samanta P, Sule P, Kumar S, Wu J, Christianson D, Horne S M, Stafslien S J, Wolfe A J et al: Environmental and genetic factors that contribute to *Escherichia coli* K-12 biofilm formation. Arch Microbiol 2010, 192(9):715-728.
(121) Horne S M, Schroeder M, Murphy J, Prubeta B M: Acetoacetate and ethyl acetoacetate as novel inhibitors of bacterial biofilm. Lett Appl Microbiol 2018.
(122) G. Gosheger et al., *Biomaterials* 25, 5547 (2004).
(123) K. Ivanova et al., *ACS Appl. Mater. Interfaces.* 7, 27066 (2015).
(124) C. Y. Loo et al., *J. Agric. Food Chem.* (2015).
(125) M. Moscoso, E. Garcia, R. Lopez, *Int. Microbiol.* 12, 77 (2009).
(126) T. J. Pritchard, K. J. Flanders, C. W. Donnelly, *Int. J. Food Microbiol.* 26, 375 (1995).
(127) G. Brightwell, J. Boerema, J. Mills, E. Mowat, D. Pulford, *Int. J. Food Microbiol.* 109, 47 (2006).
(128) R. Girard et al., *J. Hosp. Infect.* 90, 240 (2015).
(129) E. C. Murray, A. Marek, P. C. Thomson, J. E. Coia, *Nephrol. Dial. Transplant.* 30, 1202 (2015).

(130) R. Djeribi, W. Bouchloukh, T. Jouenne, B. Menaa, *Am. J Infect Control* 40, 854 (2012).
(131) L. Cerqueira, J. A. Oliveira, A. Nicolau, N. F. Azevedo, M. J. Vieira, *Biofouling* 29, 829 (2013).
(132) H. S. Choe et al., *Int. Urol. Nephrol.* 45, 743 (2013).
(133) S. Chatterjee, P. Maiti, R. Dey, A. Kundu, R. Dey, *Ann. Med. Health Sci. Res.* 4, 100 (2014).
(134) R. Zhou et al., *Invest Ophthalmol. Vis. Sci* 53, 7382 (2012).
(135) A. Pinna, D. Usai, L. A. Sechi, A. Carta, S. Zanetti, *Acta Ophthalmol.* 89, 382 (2011).
(136) E. Hurrell et al., *BMC Infect Dis* 9, 146 (2009).
(137) E. Hurrell, E. Kucerova, M. Loughlin, J. Caubilla-Barron, S. J. Forsythe, *Int. J Food Microbiol* 136, 227 (2009).
(138) U. Hagg, P. Kaveewatcharanont, Y. H. Samaranayake, L. P. Samaranayake, *Eur. J. Orthodont.* 26, 623 (2004).
(139) R. Gundelley, G. W. Youm, Y. M. Kwon, *J. Rapid Meth. Automat. Microbiol.* 15, 259 (2007).
(140) L. S. Casarin et al., *Int. J. Food Microbiol.* 191, 103 (2014).
(141) D. C. De Oliveira et al., *Foodborne. Pathog. Dis.* 11, 478 (2014).
(142) R. A. Multari, D. A. Cremers, J. A. Dupre, J. E. Gustafson, *J. Agric. Food Chem.* 61, 8687 (2013).
(143) D. M. Staskel, M. E. Briley, L. H. Field, S. S. Barth, *J. Am. Diet. Assoc.* 107, 854 (2007).
(144) K. S. Venkitanarayanan, G. O. Ezeike, Y. C. Hung, M. P. Doyle, *J. Food Prot.* 62, 857 (1999).
(145) N. Marouani-Gadri, G. Augier, B. Carpentier, *Int. J. Food Microbiol.* 133, 62 (2009).
(146) L. Axelsson et al., *J. Food Prot.* 76, 1401 (2013).
(147) G. A. Veluz, S. Pitchiah, C. Z. Alvarado, *Poult. Sci.* 91, 2004 (2012).
(148) M. Rivera-Betancourt et al., *J. Food Prot.* 67, 295 (2004).
(149) S. Silver, *FEMS Microbiol. Rev.* 27, 341 (2003).
(150) N. Fong, L. A. Poole-Warren, A. Simmons, *J. Biomed. Mater. Res. B Appl. Biomater.* 101, 310 (2013).
(151) J. Kwiecinski et al., *Appl. Environ. Microbiol.* 82, 394 (2015).
(152) T. Lynnes, S. M. Home, B. M. Prüβ, *Meat Sci* 96, 165 (2014).
(153) S. Kumari et al., *J. Bacteriol.* 182, 4173 (2000).
(154) M. Kaur, V. Gupta, S. Gombar, J. Chander, T. Sahoo, *Indian J. Med Microbiol.* 33, 248 (2015).
(155) S. J. Stafslien et al., *J. Comb. Chem.* 8, 156 (2006).
(156) P. Sule et al., *Lett. Appl. Microbiol.* 49, 299 (2009).
(157) G. A. O'Toole et al., *Methods Enzymol.* 310, 91 (1999).
(158) S. J. Pamp, C. Sternberg, T. Tolker-Nielsen, *Cytometry A* 75, 90 (2009).
(159) B. M. Prüβ et al., *Arch. Microbiol.* 192, 715 (2010).
(160) M. Irsfeld, B. M. Pruss, S. J. Stafslien, *J. Basic Microbiol.* 54, 1403 (2014).

What is claimed is:

1. A method of reducing planktonic bacterial growth or biofilm formation, the method comprising:

providing a single biofilm inhibiting compound; and contacting an article with the biofilm inhibiting compound;

wherein the biofilm inhibiting compound is selected from the group consisting of acetoacetate (AAA) and ethyl acetoacetate (EAA); and wherein the method does not include any other biofilm inhibiting compounds.

2. The method of claim 1, wherein the biofilm inhibiting compound is dissolved or dispersed in a fluid to form a biofilm inhibiting solution.

3. The method of claim 2, wherein the article is a food item.

4. The method of claim 3, wherein contacting the article with the biofilm inhibiting compound comprises mixing the food item with the biofilm inhibiting solution.

5. The method of claim 3, wherein the food item comprises raw meat.

6. The method of claim 2, wherein the article comprises tubing.

7. The method of claim 6, wherein contacting the article with the biofilm inhibiting compound comprises flushing the tubing with the biofilm inhibiting solution.

8. The method of claim 7, wherein the article comprises a catheter.

* * * * *